US008399618B2

(12) United States Patent
Lazar et al.

(10) Patent No.: US 8,399,618 B2
(45) Date of Patent: Mar. 19, 2013

(54) IMMUNOGLOBULIN INSERTIONS, DELETIONS, AND SUBSTITUTIONS

(75) Inventors: Gregory Alan Lazar, Los Angeles, CA (US); Bassil I. Dahiyat, Altadena, CA (US); Wei Dang, Pasadena, CA (US); Sher Bahadur Karki, Pomona, CA (US); Omid Vafa, Monrovia, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 13/336,907

(22) Filed: Dec. 23, 2011

(65) Prior Publication Data

US 2012/0225058 A1  Sep. 6, 2012

Related U.S. Application Data

(63) Continuation of application No. 12/020,443, filed on Jan. 25, 2008, now Pat. No. 8,101,720, which is a continuation-in-part of application No. 11/396,495, filed on Mar. 31, 2006, now abandoned, and a continuation-in-part of application No. 11/256,060, filed on Oct. 21, 2005, now abandoned.

(Continued)

(51) Int. Cl.
| C07K 16/00 | (2006.01) |
|---|---|
| C07K 1/00 | (2006.01) |
| C12P 21/08 | (2006.01) |
| A61K 39/395 | (2006.01) |
| A61K 39/40 | (2006.01) |
| A61K 39/42 | (2006.01) |
| C07K 17/00 | (2006.01) |

(52) U.S. Cl. .......... 530/350; 530/387.1; 530/387.7; 530/388.1; 530/388.15; 530/388.22; 530/388.23; 530/388.7; 424/130.1; 424/132.1; 424/133.1; 424/134.1; 424/141.1; 424/142.1; 424/143.1; 424/144.1; 424/145.1; 424/152.1; 424/153.1; 424/156.1; 424/158.1

(58) Field of Classification Search .............. None
See application file for complete search history.

(56) References Cited

U.S. PATENT DOCUMENTS

| 3,691,016 A | 9/1972 | Patel |
|---|---|---|
| 3,969,287 A | 7/1976 | Jaworek et al. |
| 4,179,337 A | 12/1979 | Davis et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,301,144 A | 11/1981 | Iwashita et al. |
| 4,330,440 A | 5/1982 | Ayers et al. |
| 4,496,689 A | 1/1985 | Mitra et al. |
| 4,640,835 A | 2/1987 | Shimizu et al. |
| 4,670,417 A | 6/1987 | Iwasaki et al. |
| 4,791,192 A | 12/1988 | Nakagawa et al. |
| 5,292,658 A | 3/1994 | Cormier et al. |
| 5,418,155 A | 5/1995 | Cormier et al. |
| 5,530,101 A | 6/1996 | Queen et al. |
| 5,585,089 A | 12/1996 | Queen et al. |
| 5,683,888 A | 11/1997 | Campbell |
| 5,693,761 A | 12/1997 | Queen et al. |
| 5,693,762 A | 12/1997 | Queen et al. |
| 5,723,323 A | 3/1998 | Kauffman et al. |
| 5,736,137 A | 4/1998 | Anderson et al. |
| 5,741,668 A | 4/1998 | Ward et al. |
| 5,763,192 A | 6/1998 | Kauffman et al. |
| 5,777,079 A | 7/1998 | Tsien et al. |
| 5,804,387 A | 9/1998 | Cormack et al. |
| 5,814,476 A | 9/1998 | Kauffman et al. |
| 5,817,483 A | 10/1998 | Kauffman et al. |
| 5,821,337 A | 10/1998 | Carter et al. |
| 5,824,514 A | 10/1998 | Kauffman et al. |
| 5,859,205 A | 1/1999 | Adair et al. |
| 5,874,304 A | 2/1999 | Zolotukhin et al. |
| 5,876,995 A | 3/1999 | Bryan et al. |
| 5,925,558 A | 7/1999 | Tsien et al. |
| 6,054,297 A | 4/2000 | Carter et al. |
| 6,180,370 B1 | 1/2001 | Queen et al. |
| 6,352,842 B1 | 3/2002 | Short et al. |
| 6,358,709 B1 | 3/2002 | Short et al. |
| 6,361,974 B1 | 3/2002 | Short et al. |
| 6,365,377 B1 | 4/2002 | Patten et al. |
| 6,376,246 B1 | 4/2002 | Crameri et al. |
| 6,407,213 B1 | 6/2002 | Carter et al. |
| 6,602,684 B1 | 8/2003 | Umana et al. |
| 6,797,492 B2 | 9/2004 | Daugherty et al. |
| 7,317,091 B2 | 1/2008 | Lazar et al. |
| 2001/0044003 A1 | 11/2001 | Gallucci et al. |
| 2002/0119492 A1 | 8/2002 | Chirino et al. |
| 2002/0168640 A1 | 11/2002 | Li et al. |
| 2002/0172968 A1 | 11/2002 | Liu et al. |
| 2003/0003097 A1 | 1/2003 | Reff et al. |
| 2003/0022285 A1 | 1/2003 | Chirino et al. |

(Continued)

FOREIGN PATENT DOCUMENTS

| WO | WO8705330 | 9/1987 |
|---|---|---|
| WO | WO9211018 | 7/1992 |

(Continued)

OTHER PUBLICATIONS

Amit et al. "Three-dimensional structure of an antigen-antibody complex @ 2.8 Å resolution" *Science* (1986) 233:747-753.
Amstutz et al., 2001, *Curr Opin Biotechnol* 12:400-405.
Ashkenazi et al., "Immunoadhesins as research tools and therapeutic agents"1997, Curr Opin Immunol 9:195-200.
Baca et al., "Antibody Humanization Using Monovalent Phage Display"1997, J. Biol. Chem. 272(16):10678-10684.
Benhar et al., "Highly Efficient Selection of Phage Antibodies Mediated by Display of Antigen as Lpp-OmpA0 Fusions on Live Bacteria"2000, *J Mol Biol* 301:893-904.
Bird et al., "Single-Chain Antigen-Binding Proteins"1988, Science 242:423-426.

(Continued)

*Primary Examiner* — Chun Dahle
(74) *Attorney, Agent, or Firm* — Morgan, Lewis & Bockius LLP

(57) ABSTRACT

An Fc variant of a parent Fc polypeptide, wherein said Fc variant exhibits altered binding to one or more FcγRs, wherein said Fc variant comprises at least one amino acid insertion in the Fc region of said parent Fc polypeptide.

9 Claims, 23 Drawing Sheets

Related U.S. Application Data

(60) Provisional application No. 60/886,635, filed on Jan. 25, 2007, provisional application No. 60/659,004, filed on Mar. 3, 2005, provisional application No. 60/652,968, filed on Feb. 14, 2005, provisional application No. 60/629,068, filed on Nov. 18, 2004, provisional application No. 60/621,387, filed on Oct. 21, 2004.

(56) References Cited

U.S. PATENT DOCUMENTS

| | | |
|---|---|---|
| 2003/0036643 A1 | 2/2003 | Jin et al. |
| 2003/0049647 A1 | 3/2003 | Dahiyat et al. |
| 2003/0050331 A1 | 3/2003 | Ng et al. |
| 2003/0068649 A1 | 4/2003 | Doberstein et al. |
| 2003/0124537 A1 | 7/2003 | Liu et al. |
| 2003/0157108 A1 | 8/2003 | Presta et al. |
| 2004/0132101 A1 | 7/2004 | Lazar et al. |
| 2004/0230380 A1 | 11/2004 | Chirino et al. |
| 2005/0114037 A1 | 5/2005 | Desjarlais et al. |
| 2006/0008883 A1 | 1/2006 | Lazar et al. |
| 2006/0235208 A1 | 10/2006 | Lazar et al. |
| 2006/0275283 A1 | 12/2006 | van Vlijmen et al. |
| 2007/0148171 A1 | 6/2007 | Lazar et al. |
| 2007/0166309 A1 | 7/2007 | Lazar et al. |
| 2008/0206242 A1 | 8/2008 | Lawrence et al. |
| 2008/0240845 A1 | 10/2008 | Drelon et al. |

FOREIGN PATENT DOCUMENTS

| | | |
|---|---|---|
| WO | WO9215673 | 9/1992 |
| WO | WO9311161 | 6/1993 |
| WO | WO9413804 | 6/1994 |
| WO | WO9507463 | 3/1995 |
| WO | WO9814605 | 4/1998 |
| WO | WO9826277 | 6/1998 |
| WO | WO9852976 | 11/1998 |
| WO | WO9859244 | 12/1998 |
| WO | WO9949019 | 9/1999 |
| WO | WO0042561 | 7/2000 |
| WO | WO0061739 | 10/2000 |
| WO | WO0114539 | 3/2001 |
| WO | WO0129246 | 4/2001 |
| WO | WO0170947 | 9/2001 |
| WO | WO0205146 | 1/2002 |
| WO | WO0206469 | 1/2002 |
| WO | WO0222826 | 3/2002 |
| WO | WO0230954 | 4/2002 |
| WO | WO0231140 | 4/2002 |
| WO | WO02066653 | 8/2002 |
| WO | WO02068453 | 9/2002 |
| WO | WO02068698 | 9/2002 |
| WO | WO02069232 | 9/2002 |
| WO | WO02077187 | 10/2002 |
| WO | WO03000405 | 1/2003 |
| WO | WO03006154 | 1/2003 |
| WO | WO03025154 | 3/2003 |
| WO | WO2004029207 | 4/2004 |
| WO | WO2004056312 | 7/2004 |
| WO | WO2005056606 | 6/2005 |
| WO | WO2005056759 | 6/2005 |

OTHER PUBLICATIONS

Boder et al, "Yeast Surface Display for Directed Evolution of Protein Expression, Affinity, and Stability" 2000, Methods Enzymol 328:430-44.
Boder, et al., "Yeast surface display for screening combinatorial polypeptide libraries" 1997, Nat Biotechnol 15:553-557.
Boruchov et al., "Activating and inhibitory IgG Fc receptors on human DCs mediate opposing functions"2005, J Clin Invest, Sep. 15, 1-10.
Carter et al., "Humanization of an anti-p185HER2 antibody for human cancer therapy" 1992, Proc Natl Acad Sci USA 89:4285-9.
Cartron et al., "Therapeutic activity of humanized anti-CD20 monoclonal antibody and polymorphism in IgG Fc receptor Fc_RIIIa gene" 2002, Blood 99:754-758.
Chalfie et al., "Green Florescent Protein as a Marker for Gene Expression" 1994, Science 263:802-805.
Chamow et al., "Immunoadhesins: principles and applications" 1996, Trends Biotechnol 14:52-60.
Chappel et al., "Identification of a Secondary FcyRI Binding Site within a Genetically Engineered Human IgG Antibody"1993, Journal of Biological Chemistry 268:25124-25131.
Chappel et al., "Identification of the Fcy receptor class I binding site in human IgG through the use of recombinant IgG1/IgG2 hybrid and point-mutated antibodies"1991, Proc. Natl. Acad. Sci. USA 88(20):9036-9040.
Chen et al., "Isolation of high-affinity ligand-binding proteins by periplasmic expression with cytometric screening (PECS)"2001, Nat Biotechnol 19:537-542.
Clark, "Antibody humanization: a case of the 'Emperor's new clothes'?"2000, Immunol Today 21:397-402).
Clark, 1997, IgG effector mechanisms, Chem Immunol. 65:88-110.
Clynes et al., Fc receptors are required in passive and active immunity to melanoma 1998, Proc Natl Acad Sci U S A 95:652-656.
Clynes et al., "Inhibitory Fc receptors modulate in vivo cytoxicity against tumor targets"2000, Nat Med 6:443-446.
Cobleigh et al., "Multinational Study of the Efficacy and Safety of Humanized Anti-HER2 Monoclonal Antibody in Women Who Have HER2-Overexpressing Metastatic Breast Cancer That Has Progessed After Chemotherapy for Metastic Disease" 1999, J Clin Oncol 17:2639-2648.
Coco et al., "DNA shuffling method for generating highly recombined genes and evolved enzymes" 2001, Nat Biotechnol 19:354-359.
Cragg et al., "Signaling antibodies in cancer therapy"1999, Curr Opin Immunol 11:541-547;.
Crameri et al., "DNA shuffling of a family of genes from diverse species accelerates directed evolution"1998, Nature 391:288-291.
Davies et al., "Expression of GnTIII in a Recombinant Anti-CD20 CHO Production Cell Line: Expression of Antibodies with Altered Glycoforms Leads to an Increase in ADCC Through Higher Affinity for FcgRIII"2001, Biotechnol Bioeng 74:288-294.
Davis et al., "Fc receptor homologs: newest members of a remarkably diverse Fc receptor gene family." 2002, Immunological Reviews 190:123-136.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody"2002, J. Immunol. 169:3076-3084.
Deisenhofer, "Crystallographic Refinement and Atomic Models of a Human Fc Fragment and Its Complex with Fragment B of Protein A from Staphylococcus aureus at 2.9- and 2.8-A Resolution+"1981, Biochemistry 20:2361-2370.
DeLano et al., "Convergent Solutions to Binding at a Protein-Protein Interface"2000, Science 287:1279-1283.
Dhodapkar, "Recruiting dendritic cells to improve antibody therapy of cancer" 2005, Proc Natl Acad Sci USA, 102, 6243-6244.
Duskin et al., "Relationship of the Structure and Biological Activitoyf the Natural Homologues of Tunicamycin*"1982, J. Biol. Chem. 257:3105.
Edge et al., "Deglycosylation of Glycoproteins by Trifluoromethanesulfonic Acid" 1981, Anal. Biochem. 118:131.
Garman et al., "Structure of the Fc fragment of human IgE bound to its high-affinity receptor FceRla"2000, Nature 406:259-266.
Georgiou et al., "Display of heterologous proteins on the surface of microorganisms: From the screening of combinatorial libraries to live recombinant vaccines" 1997, Nat Biotechnol 15:29-34.
Georgiou et al., "Practical applications of engineering Gram-negative bacterial cell surfaces"1993, Trends Biotechnol 11:6-10.
Ghetie et al., "Multiple Roles for the Major Histocompatibility Complex Class I-Related Receptor FCRN" 2000, Annu Rev Immunol 18:739-766.
Glennie et al., "Clinical trials of antibody therapy"2000, Immunol Today 21:403-410.
Gorman et al., "Reshaping a Therapeutic CD4 Antibody"1991, Proc. Natl. Acad. Sci. USA 88:4181-4185.

Gorman, et al., "Humanisation of monoclonal antibodies for therapy" 1990, Semin Immunol 2(6):457-66.

Hakimuddin et al., "A Chemical Method for the Deglycosylation of Proteins" 1987, Arch. Biochem. Biophys. 259:52.

Hammer et al., "Precise Prediction of Major Histocompatibility Complex Class II-Peptide Interaction Based on Peptide Side Chain Scanning"1994, *J. Exp. Med*. 180: 2353-2358.

Hanes et al., "In vitro selection and evolution of functional proteins by using ribosome display"1997, Proc Natl Acad Sci USA 94:4937-4942.

Hayhurst, et al., "High-throughput antibody isolation" 2001, *Curr Opin Chem Biol* 5:683-689.

He et al., "Humanization and Pharmacokinetics of a Monoclonal Antibody with Specificity for Both E- and P-Selectin"1998, J. Immunol. 160: 1029-1035.

Heim et al., "Engineering green fluorescent protein for improved brightness, longer wavelengths and fluorescence resonance energy transfer"1996, Curr. Biol. 6:178-182.

Holliger et al., ""Diabodies": Small Bivalent and Bispecific Antibody Fragments"1993, Proc. Natl. Acad. Sci. U.S.A. 90:6444-6448.

Hu et al., "Minibody: A Novel Engineered Anti-Carcinoembryonic Antigen Antibody Fragment (Single-Chain Fv-CH3) Which Exhibits Rapid, High-Level Targeting of Xenografts1"1996, Cancer Res. 56:3055-3061.

Huston et al., "Protein Engineering of Antibody Binding Sites: Recovery of Specific Activity in an Anti-Digoxin Single-Chain Fv Analogue Produced in *Escherichia coli*"1988, Proc. Natl. Acad. Sci. U.S.A. 85:5879-5883).

Ichiki et al., "Regulation of the Expression of Human Cε Germline Transcript—"1993, J. Immunol. 150:5408-5417.

James et al., "1.9 Å Structure of the Therapeutic Antibody CAMPATH-1H Fab in Complex with a Synthetic Peptide Antigen"1999, *J Mol Biol* 289:293-301).

Jefferis et al., "Interaction sites on human IgG-Fc for FcgR: current models" 2002, *Immunol Lett* 82:57-65.

Johnson et al, "Kabat Database and its application: 30 years after the first variability plot" 2000, *Nucleic Acids Res*. 28:214-218).

Johnson et al., "Kabat Database and its application: future directions" 2001, *Nucleic Acids Res*. 29:205-206.

Johnsson et al, "Split ubiquitin as a sensor of protein interactions in vivo" 1994, *Proc Natl Acad Sci USA* 91:10340-10344.

Jones et al., "Replacing the complementarity-determining regions in a human antibody with those from a mouse"1986, *Nature* 321:522-525.

Jung et al., "Surface display of *Zymomonas mobilis* levansucrase by using the ice-nucleation protein of *Pseudomonas syringae*"1998, *Nat Biotechnol* 16:576-80).

Kikuchi et al., "An effective family shuffling method using single-stranded DNA"2000, *Gene* 243:133-137.

Kikuchi et al., "Novel family shuffling methods for the in vitro evolution of enzymes" 1999 *Gene* 236:159-167.

Kim et al., "Analysis of FcgRIII and IgG Fc Polymorphism Reveals Functional and Evolutionary Implications of Protein—Protein Interaction" 2001, J. Mol. Evol. 54:1-9.

Kolkman, et al., "Directed evolution of proteins by exon shuffling" 2001, *Nat Biotechnol* 19:423-428.

Krapp et al., "Structural Analysis of Human IgG-Fc Glycoforms Reveals a Correlation Between Glycosylation and Structural Integrity"2003, *J Mol Biol* 325:979-989).

Krauss et al., "Specificity grafting of human antibody frameworks selected from a phage display library: generation of a highly stable humanized anti-CD22 single-chain Fv fragment"2003, Protein Engineering 16(10):753-759.

Krebber et al., "Selectively-infective Phage (SIP): A Mechanistic Dissection of a Novel in vivo Selection for Protein-ligand Interactions"1997, *J Mol Biol* 268:619-630.

Lee et al., "Surface-displayed viral antigens on *Salmonella* carrier vaccine"2000, *Nat Biotechnol* 18:645-648.

Lefranc et al., "IMGT, the international ImMunoGeneTics database" 1999, *Nucleic Acids Res*. 27:209-212.

Lefranc et al., "IMGT, the international ImMunoGeneTics database" 2001, *Nucleic Acids Res*. 29:207-209.

Lefranc et al., "IMGT, the international ImMunoGeneTics database" 2003, *Nucleic Acids Res*. 31:307-310).

Lefranc, et al., The human IgG subclasses: molecular analysis of structure, function and regulation. Pergamon, Oxford, pp. 43-78 (1990).

Lefranc, G. et al., "Gm, Am and Km Immunoglobulin Allotypes of Two Populations in Tunisia" 1979, Hum. Genet.: 50, 199-211.

Lehrnbecher et al., "Variant Genotypes of the Low-Affinity Fcg Receptors in Two Control Populations and a Review of Low-Affinity Fcg Receptor Polymorphisms in Control and Disease Populations"1999, *Blood* 94:4220-4232.

Little et al., "Of mice and men: hybridoma and recombinant antibodies"2000, *Immunol Today* 21:364-370.

Lowman et al., "Selecting High-Affinity Binding by Monovalent Phage Display" 1991, *Biochemistry* 30:10832-10838.

Lutz et al., "Creating multiple-crossover DNA libraries independent of sequence identity"2001, *Proc Natl Acad Sci USA* 98:11248-11253.

Mallios, et al., "Class II MHC quantitative binding motifs derived from a large molecular database with a versatile iterative stepwise discriminant analysis meta-algorithm" 1999, *Bioinformatics* 15: 432-439.

Mallios, et al., "Predicting class II MHC/peptide multi-level binding with an iterative stepwise discriminant analysis meta-algorithm" 2001, *Bioinformatics* 17: 942-948.

Malmborg et al., "Selective Phage Infection Mediated by Epitope Expression on F Pilus"1997, J Mol Biol 273:544-551.

Marshall et al., "Prediction of Peptide Affinity to HLA DRB1*0401" 1995, *J. Immunol.* 154: 5927-5933.

Martin et al., "Crystal Structure at 2.8 Å of an FcRn/Heterodimeric Fc Complex: Mechanism of pH-Dependent Binding"2001, *Mol Cell* 7:867-877.

Mattheakis et al., "An in vitro polysome display system for identifying ligands from very large peptide libraries" 1994, *Proc Natl Acad Sci USA* 91:9022-9026.

Maxwell et al., "Crystal structure of the human leukocyte Fc receptor, Fc RIIa."1999, *Nat Struct Biol* 6:437-442.

Maynard, et al. "Antibody Engineering" 2000, *Annu Rev Biomed Eng* 2:339-76.

McLaughlin et al., "Rituximan Chimeric Anti-CD20 Monoclonal Antibody Therapy for Relapsed Indolent Lymphoma: Half of Patients Respond to a Four-Dose Treatment Program" 1998, *J Clin Oncol* 16:2825-2833.

Michaelsen et al., "Antibody Dependent Cell-Mediated Cytotoxicity Induced by Chimeric Mouse-Human $I_GG$ Subclasses and $I_G$3 Antibodies With Altered Hinge Region" 1992, Molecular Immunology, 29(3): 319-326.

Mimura et al., "Role of Oligosaccharide Residues of IgG1-Fc in Fc_RIIb Binding"2001, *J Biol Chem* 276:45539-45547.

Morea et al., "Antibody Modeling: Implications for Engineering and Design"2000, *Methods* 20:267-279.

Morea et al., "Antibody structure, prediction and redesign" 1997, *Biophys Chem* 68:9-16.

Nemoto et al., "In vitro virus" Bonding of mRNA bearing puromycin at the 3'-terminal end to the C-terminal end of its encoded protein on the ribosome in vitro 1997, *FEBS Lett* 414:405-408.

Nolan et al., "Fluorescence-Activated Cell Analysis and Sorting of Viable Mammalian Cells Based on β-D-galactosidase Activity after Transduction of *Escherichia coli* lacZ"1988, Proc. Natl. Acad. Sci. U.S.A. 85:2603-2607.

O'Connor et al., "Humanization of an antibody against human protein C and calcium-dependence involving framework residues"1998, *Protein Eng* 11:321-8.

Pelletier et al., "Oligomerization domain-directed reassembly of active dihydrofolate reductase from rationally designed fragments" 1998, *Proc Natl Aced Sci USA* 95:12141-12146.

Presta et al., "Humanization of an Anti-Vascular Endothelial Growth Factor Monoclonal Antibody for the Therapy of Solid Tumors and Other Disorders"1997, Cancer Res.57(20):4593-9.

Queen et al., "A Humanized Antibody that Binds to the Interleukin 2 Receptor" 1989, Proc Natl Acad Sci, USA 86:10029-33.

Radaev et al., "Recognition of IgG by Fcg Receptor"2001, *J Biol Chem* 276:16478-16483.

Radaev et al., "The Structure of a Human Type III Fcg Receptor in Complex with Fc*"2001, *J Biol Chem* 276:16469-16477.

Rader et al., "A phage display approach for rapid antibody humanization: Designed combinatorial V gene libraries"1998, Proc. Natl. Acad. Sci. USA 95: 8910-8915.

Raghavan et al., "Fc Receptors and Their Interactions With Immunoglobulins"1996, *Annu Rev Cell Dev Biol* 12:181-220.

Ravetch et al., "IGG FC Receptors"2001, *Annu Rev Immunol* 19:275-290.

Reiter et al., "Engineering antibody Fv fragments for cancer detection and therapy: Disulfide-stablized Fv fragments"1996, Nature Biotech. 14:1239-1245.

Riechmann et al., Reshaping human antibodies for therapy 1988; *Nature* 332:323-329.

Roberts, et al., "RNA-peptide fusions for the in vitro selection of peptides and proteins" 1997, *Proc Natl Acad Sci USA* 94:12297-12302.

Roguska et al., "Humanization of Murine Monoclonal Antibodies Through Variable Domain Resurfacing"1994, Proc. Natl. Acad. Sci. USA 91:969-973.

Roque et al., "Antibodies and Genetically Engineered Related Molecules: Production and Purification"2004, Biotechnol. Prog. 20:639-654.

Rosok et al., "A Combinatorial Library Strategy for the Rapid Humanization of Anticarcinoma BR96 Fab*" 1996, J. Biol. Chem. 271(37): 22611-22618.

Rudikoff et al. "Single amino acid subsititution altering antigen binding specificity" *PNAS* (1982) 79:1979-1983.

Ruiz et al., "IMGT, the international ImMunoGenTics database" 2000 *Nucleic Acids Res*. 28:219-221.

Sauer-Eriksson et al., "Crystal structure of the C2 fragment of streptococcal protein G in complex with the Fc domain of human IgG"1995, Structure 3:265-278.

Schmittel et. al., "Application of the IFN-g ELISPOT assay to quantify T cell responses against proteins"2000, *J. Immunol. Meth.*, 24: 17-24.

Score Search Results GenCore version 6.3 SEQ ID No. 15 alignment results. Jan. 27, 2010, pp. 1-55.

Shao et al., "Random-priming in vitro recombination: an effective tool for directed evolution"1998, *Nucleic Acids Res* 26:681-683.

Shields et al., "High Resolution Mapping of the Binding Site on Human IgG1 for FcgRI, FcgRII, FcgRIII, and FcRn and Design of IgG1 Variants with Improved Binding to the FcgR*"2001, *J Biol Chem* 276:6591-6604.

Shields et al., "Lack of Fucose on Human IgG1 N-Linked Oligosaccharide Improves Binding to Human Fc_RIII and Antibody-dependent Cellular Toxicity"2002, *J Biol Chem* 277:26733-26740.

Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity"2003, J Biol Chem 278:3466-3473.

Simmons et al., "Expression of full-length immunoglobulins in *Escherichia coli*: rapid and efficient production of aglycosylated antibodies"2002, *J Immunol Methods* 263:133-147.

Smith, et al., "Filamentous Fusion Phage: Novel Expression Vectors That Display Cloned Antigens on the Virion Surface"1985, *Science* 228:1315-1317.

Sondermann et al., "Molecular Basis for Immune Complex Recognition: A Comparison of Fc-Receptor Structures"2001, *J Mol Biol* 309:737-749.

Sondermann et al., "Crystal structure of the soluble form of the human Fcg-receptor IIb: a new member of the immunoglobulin superfamily at 1.7 Å resolution"1999, *Embo J* 18:1095-1103.

Sondermann et al., "The 3.2-Å crystal structure of the human IgG1 Fc fragment±FcgRIII complex"2000, *Nature* 406:267-273.

Stauber, 1998, Biotechniques 24:462-471.

Sturniolo et al., "Generation of tissue-specific and promiscuous HLA ligand databases using DNA microarrays and virtual HLA class II matrices" 1999, *Nature Biotech*. 17: 555-561.

Tan et al., ""Superhumanized" Antibodies: Reduction of Immunogenic Potential by Complementarity-Determining Region Grafting with Human Germline Sequences: Application to an Anti-CD281"2002, J. Immunol. 169:1119-1125.

Tashiro et al., "Structures of bacterial immunoglobulin-binding domains and their complexes with immunoglobulins"1995, *Curr Opin Struct Biol* 5:471-481.

Thotakura et al., "Enzymatic Deglycosylation of Glycoproteins"1987, Meth. Enzymol. 138:350.

Tomlinson et. al., "Methods for Generating Multivalent and Bispecific Antibody Fragments" 2000, Methods Enzymol. 326:461-479.

Tsurushita, et al., "Molecular Biology of B Cells" 2004, 533-545.

Umaña et al., "Engineered glycoforms of an antineuroblastoma IgG1 with optimized antibodydependent cellular cytotoxic activity"1999, *Nat Biotechnol* 17:176-180.

Vajdos et al. "Comprehensive functional mapping of the antigen binding site of an anti-ErbB2 antibody obtained with shotgun scanning mutagenesis" *Journal Molecular Biology* (2002) 320: 415-428.

Verhoeyen et al., "Reshaping Human Antibodies: Grafting an Antilysozyme Activity"1988, Science 239:1534-1536.

Visintin et al., "Selection of antibodies for intracellular function using a two-hybrid in vivo system"1999, *Proc Natl Acad Sci USA* 96:11723-11728.

Ward et al., "Binding activities of a repertoire of single immunoglobulin variable domains secreted from *Escherichia coli*" 1989, Nature 341:544-546.

Whitehorn et al., "A Generic Method for Expression and Use of "Tagged" Souble Versions of Cell Surface Receptors" 1995, *Bio/technology* 13:1215-1219.

WHO Review of the notation for the allotypic and related markers of human immunoglobulins. J Immunogen 1976, 3:357-362.

WHO Review of the notation for the allotypic and related markers of human immunoglobulins. 1976, Eur. J. Immunol. 6, 599-601.

Witrrup, "Protein engineering by cell-surface display"2001, *Curr Opin Biotechnol*, 12:395-399.

Wu et al., "Humanization of a Murine Monoclonal Antibody by Simultaneous Optimization of Framework and CDR Residues"1999, J. Mol. Biol. 294:151-162.

Zhao et al., "Molecular evolution by staggered extension process (StEP) in vitro recombination"1998, *Nat Biotechnol* 16:258-261.

Zhou et al., "A Novel Strategy by the Action of Ricin that Connects Phenotype and Genotype without Loss of the Diversity of Libraries"2002, *J Am Chem Soc* 124, 538-543.

Harada, et al., "Hinge Region of Human IgG2 Protein: Conformational Studies with Monoclonal Antibodies" Molecular Immunology, vol. 29, pp. 145-149 (1992).

Jassal, et al., "Sialylation of human IgG-Fc carbohydrate by transfected rat alpha2, 6-sialytrasnferase" Biochem &Biophysical Res. Comm. vol. 286, No. 2, pp. 243-249 (2001).

Lund et al., "Multiple interactions of IgG with its core oligosaccharide can modulate recognition by complement and human Fc gamma receptor I and influence the synthesis of its oligosaccharide chains", J. Imm. Am. Assoc. of Immuno. vol. 157, No. 11, ps. 4963-4969 (1996).

CH1

| EU index | 118 | 119 | 120 | 121 | 122 | 123 | 124 | 125 | 126 | 127 | 128 | 129 | 130 | 131 | 132 | 133 | 134 | 135 | 136 | 137 | 138 |
|---|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G | G |
| IgG2 | A | S | T | K | G | P | S | V | F | P | L | A | P | C | S | R | S | T | S | E | S |
| IgG3 | A | S | T | K | G | P | S | V | F | P | L | A | P | C | S | R | S | T | S | G | G |
| IgG4 | A | S | T | K | G | P | S | V | F | P | L | A | P | C | S | R | S | T | S | E | S |

| EU index | 139 | 140 | 141 | 142 | 143 | 144 | 145 | 146 | 147 | 148 | 149 | 150 | 151 | 152 | 153 | 154 | 155 | 156 | 157 | 158 | 159 |
|---|---|---|---|---|---|---|---|---|---|---|---|---|---|---|---|---|---|---|---|---|---|
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |

| EU index | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |

| EU index | 181 | 182 | 183 | 184 | 185 | 186 | 187 | 188 | 189 | 190 | 191 | 192 | 193 | 194 | 195 | 196 | 197 | 198 | 199 | 200 | 201 |
|---|---|---|---|---|---|---|---|---|---|---|---|---|---|---|---|---|---|---|---|---|---|
| IgG1 | S | L | S | S | V | V | T | V | P | S | S | S | L | G | T | Q | T | Y | I | C | N |
| IgG2 | S | L | S | S | V | V | T | V | P | S | S | N | F | G | T | Q | T | Y | T | C | N |
| IgG3 | S | L | S | S | V | V | T | V | P | S | S | S | L | G | T | Q | T | Y | T | C | N |
| IgG4 | S | L | S | S | V | V | T | V | P | S | S | S | L | G | T | K | T | Y | T | C | N |

| EU index | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|---|
| IgG1 | V | N | H | K | P | S | N | T | K | V | D | K | K | V | E | P | K | S | C |
| IgG2 | V | D | H | K | P | S | N | T | K | V | D | K | T | V | E | R | K | C | C |
| IgG3 | V | N | H | K | P | S | N | T | K | V | D | K | R | V | E | L | K | T | P |
| IgG4 | V | D | H | K | P | S | N | T | K | V | D | K | R | V | E | S | K | Y | G |

Hinge        Fc >

| EU index | 221 | 222 | 223 | 224 | 225 | 226 | 227 | 228 |
|---|---|---|---|---|---|---|---|---|
| IgG1 | D | | | K | T | H | T | C | P | P |
| IgG2 | | V | E | | | C | P | P |
| IgG3 | L | G | D | T | T | H | T | C | P | R C P E P K S C D T P P |
| IgG4 | | | | | P | P | C | P | S |

Fig. 1

```
EU Index
  IgG1
  IgG2
  IgG3   P C P R C P E P K S C D T P P P C P R C P
  IgG4

Fc >
EU Index                                        229 230 231 232 233 234 235 236
  IgG1                                           C   P   A   P   E   L   L   G
  IgG2                                           C   P   A   P   P   V   A
  IgG3   E P K S C D T P P P C P R              C   P   A   P   E   L   L   G
  IgG4                                           C   P   A   P   E   F   L   G CH2
EU Index 237 238 239 240 241 242 243 244 245 246 247 248 249 250 251 252 253 254 255 256 257
  IgG1    G   P   S   V   F   L   F   P   P   K   P   K   D   T   L   M   I   S   R   T   P
  IgG2    G   P   S   V   F   L   F   P   P   K   P   K   D   T   L   M   I   S   R   T   P
  IgG3    G   P   S   V   F   L   F   P   P   K   P   K   D   T   L   M   I   S   R   T   P
  IgG4    G   P   S   V   F   L   F   P   P   K   P   K   D   T   L   M   I   S   R   T   P EU Index 258 259 260 261 262 263 264 265 266 267 268 269 270 271 272 273 274 275 276 277 278
  IgG1    E   V   T   C   V   V   V   D   V   S   H   E   D   P   E   V   K   F   N   W   Y
  IgG2    E   V   T   C   V   V   V   D   V   S   H   E   D   P   E   V   Q   F   N   W   Y
  IgG3    E   V   T   C   V   V   V   D   V   S   H   E   D   P   E   V   Q   F   K   W   Y
  IgG4    E   V   T   C   V   V   V   D   V   S   Q   E   D   P   E   V   Q   F   N   W   Y EU Index 279 280 281 282 283 284 285 286 287 288 289 290 291 292 293 294 295 296 297 298 299
  IgG1    V   D   G   V   E   V   H   N   A   K   T   K   P   R   E   E   Q   Y   N   S   T
  IgG2    V   D   G   V   E   V   H   N   A   K   T   K   P   R   E   E   Q   F   N   S   T
  IgG3    V   D   G   V   E   V   H   N   A   K   T   K   P   R   E   E   Q   Y   N   S   T
  IgG4    V   D   G   V   E   V   H   N   A   K   T   K   P   R   E   E   Q   F   N   S   T EU Index 300 301 302 303 304 305 306 307 308 309 310 311 312 313 314 315 316 317 318 319 320
  IgG1    Y   R   V   V   S   V   L   T   V   L   H   Q   D   W   L   N   G   K   E   Y   K
  IgG2    F   R   V   V   S   V   L   T   V   V   H   Q   D   W   L   N   G   K   E   Y   K
  IgG3    F   R   V   V   S   V   L   T   V   L   H   Q   D   W   L   N   G   K   E   Y   K
  IgG4    Y   R   V   V   S   V   L   T   V   L   H   Q   D   W   L   N   G   K   E   Y   K
```

Fig. 1 (cont.)

| EU Index | 321 | 322 | 323 | 324 | 325 | 326 | 327 | 328 | 329 | 330 | 331 | 332 | 333 | 334 | 335 | 336 | 337 | 338 | 339 | 340 |
|---|---|---|---|---|---|---|---|---|---|---|---|---|---|---|---|---|---|---|---|---|
| IgG1 | C | K | V | S | N | K | A | L | P | A | P | I | E | K | T | I | S | K | A | K |
| IgG2 | C | K | V | S | N | K | G | L | P | A | P | I | E | K | T | I | S | K | T | K |
| IgG3 | C | K | V | S | N | K | A | L | P | A | P | I | E | K | T | I | S | K | T | K |
| IgG4 | C | K | V | S | N | K | G | L | P | S | S | I | E | K | T | I | S | K | A | K |

CH3

| EU Index | 341 | 342 | 343 | 344 | 345 | 346 | 347 | 348 | 349 | 350 | 351 | 352 | 353 | 354 | 355 | 356 | 357 | 358 | 359 | 360 | 361 |
|---|---|---|---|---|---|---|---|---|---|---|---|---|---|---|---|---|---|---|---|---|---|
| IgG1 | G | Q | P | R | E | P | Q | V | Y | T | L | P | P | S | R | D | E | L | T | K | N |
| IgG2 | G | Q | P | R | E | P | Q | V | Y | T | L | P | P | S | R | E | E | M | T | K | N |
| IgG3 | G | Q | P | R | E | P | Q | V | Y | T | L | P | P | S | R | E | E | M | T | K | N |
| IgG4 | G | Q | P | R | E | P | Q | V | Y | T | L | P | P | S | Q | E | E | M | T | K | N |

| EU Index | 362 | 363 | 364 | 365 | 366 | 367 | 368 | 369 | 370 | 371 | 372 | 373 | 374 | 375 | 376 | 377 | 378 | 379 | 380 | 381 | 382 |
|---|---|---|---|---|---|---|---|---|---|---|---|---|---|---|---|---|---|---|---|---|---|
| IgG1 | Q | V | S | L | T | C | L | V | K | G | F | Y | P | S | D | I | A | V | E | W | E |
| IgG2 | Q | V | S | L | T | C | L | V | K | G | F | Y | P | S | D | I | A | V | E | W | E |
| IgG3 | Q | V | S | L | T | C | L | V | K | G | F | Y | P | S | D | I | A | V | E | W | E |
| IgG4 | Q | V | S | L | T | C | L | V | K | G | F | Y | P | S | D | I | A | V | E | W | E |

| EU Index | 383 | 384 | 385 | 386 | 387 | 388 | 389 | 390 | 391 | 392 | 393 | 394 | 395 | 396 | 397 | 398 | 399 | 400 | 401 | 402 | 403 |
|---|---|---|---|---|---|---|---|---|---|---|---|---|---|---|---|---|---|---|---|---|---|
| IgG1 | S | N | G | Q | P | E | N | N | Y | K | T | T | P | P | V | L | D | S | D | G | S |
| IgG2 | S | N | G | Q | P | E | N | N | Y | K | T | T | P | P | M | L | D | S | D | G | S |
| IgG3 | S | S | G | Q | P | E | N | N | Y | N | T | T | P | P | M | L | D | S | D | G | S |
| IgG4 | S | N | G | Q | P | E | N | N | Y | K | T | T | P | P | V | L | D | S | D | G | S |

| EU Index | 404 | 405 | 406 | 407 | 408 | 409 | 410 | 411 | 412 | 413 | 414 | 415 | 416 | 417 | 418 | 419 | 420 | 421 | 422 | 423 | 424 |
|---|---|---|---|---|---|---|---|---|---|---|---|---|---|---|---|---|---|---|---|---|---|
| IgG1 | F | F | L | Y | S | K | L | T | V | D | K | S | R | W | Q | Q | G | N | V | F | S |
| IgG2 | F | F | L | Y | S | K | L | T | V | D | K | S | R | W | Q | Q | G | N | V | F | S |
| IgG3 | F | F | L | Y | S | K | L | T | V | D | K | S | R | W | Q | Q | G | N | I | F | S |
| IgG4 | F | F | L | Y | S | R | L | T | V | D | K | S | R | W | Q | E | G | N | V | F | S |

| EU Index | 425 | 426 | 427 | 428 | 429 | 430 | 431 | 432 | 433 | 434 | 435 | 436 | 437 | 438 | 439 | 440 | 441 | 442 | 443 | 444 | 445 |
|---|---|---|---|---|---|---|---|---|---|---|---|---|---|---|---|---|---|---|---|---|---|
| IgG1 | C | S | V | M | H | E | A | L | H | N | H | Y | T | Q | K | S | L | S | L | S | P |
| IgG2 | C | S | V | M | H | E | A | L | H | N | H | Y | T | Q | K | S | L | S | L | S | P |
| IgG3 | C | S | V | M | H | E | A | L | H | N | R | F | T | Q | K | S | L | S | L | S | P |
| IgG4 | C | S | V | M | H | E | A | L | H | N | H | Y | T | Q | K | S | L | S | L | S | L |

| EU Index | 446 | 447 | |
|---|---|---|---|
| IgG1 | G | K | Seq ID NO. 1 |
| IgG2 | G | K | Seq ID NO. 2 |
| IgG3 | G | K | Seq ID NO. 3 |
| IgG4 | G | K | Seq ID NO. 4 |

| Allotype | Allotype | Position | | |
|---|---|---|---|---|
| | | 214 | 356 358 | 431 |
| G1m(1,17) | G1m(a,z) | K | D L | A |
| G1m(1,2,17) | G1m(a,x,z) | K | D L | G |
| G1m(3) | G1m(f) | R | E M | A |
| G1m(1,3) | G1m(a,f) | R | D L | A |

FIG. 2b

| Allotype | Allotype | Position |
|---|---|---|
| | | 282 |
| G2m(23) | G2m(n+) | V |
| | G2m(n-) | M |

FIG. 3a

| Hinge | CH1 | | Hinge | | | | | | | | | | | | | CH2 | |
|---|---|---|---|---|---|---|---|---|---|---|---|---|---|---|---|---|---|
| EU Index | 219 | 220 | 221 | 222 | 223 | 224 | 225 | 226 | 227 | 228 | 229 | 230 | 231 | 232 | 233 | 234 | 235 | 236 | 237 | 238 |
| IgG1 | S | C | D | K | T | H | T | C | P | P | C | P | A | P | E | L | L | G | G | P |

FIG. 4

| Modification(s)<br># = deletion<br>^ = insertion after | IgG | Insertion/Deletion<br>Description | Hinge<br>230-238 |
|---|---|---|---|
| WT IgG1 | IgG1 | | PAPELLGGP |
| WT IgG2 | IgG2 | | PAPPVAGP |
| WT IgG4 | IgG4 | | PAPEFLGGP |
| L235G | IgG1 | | PAPELGGGP |
| G236R | IgG1 | | PAPELLRGP |
| G237K | IgG1 | | PAPELLGKP |
| N325L | IgG1 | | PAPELLGGP |
| N325A | IgG1 | | PAPELLGGP |
| L328R | IgG1 | | PAPELLGGP |
| L235G/G236R | IgG1 | | PAPELGRGP |
| G236R/G237K | IgG1 | | PAPELLRKP |
| G236R/N325L | IgG1 | | PAPELLRGP |
| G237K/N325L | IgG1 | | PAPELLGKP |
| G236R/L328R | IgG1 | | PAPELLRGP |
| N325A/L328R | IgG1 | | PAPELLGGP |
| N325L/L328R | IgG1 | | PAPELLGGP |
| L235G/G236R/G237K | IgG1 | | PAPELGRKP |
| G236R/G237K/L328R | IgG1 | | PAPELLRKP |
| G237# | IgG1 | delete G237 | PAPELLGP |
| G236#/G237# | IgG1 | delete G236 & G2367 | PAPELLP |
| ^236R | IgG1 | insert R after G236 | PAPELLGRGP |
| ^237R | IgG1 | insert R after G237 | PAPELLGGRP |
| ^237RR | IgG1 | insert 2 R's after G237 | PAPELLGGRRP |
| G237#/L328R | IgG1 | delete G237 (+L328R) | PAPELLGP |
| G236#/G237#/L328R | IgG1 | delete G236 & G2367 (+L328R) | PAPELLP |
| ^236R/L328R | IgG1 | insert R after G236 (+L328R) | PAPELLGRGP |
| ^237R/L328R | IgG1 | insert R after G237 (+L328R) | PAPELLGGRP |
| ^237RR/L328R | IgG1 | Insert 2 R's after G237 (+L328R) | PAPELLGGRRP |
| L328R | IgG2 | | PAPPVAGP |
| ^235R | IgG2 | insert R after A235 | PAPPVARGP |
| V234# | IgG2 | delete V234 | PAPPAGP |
| A235# | IgG2 | delete A235 | PAPPVGP |
| G237# | IgG2 | delete G237 | PAPPVAP |
| ^235R/L328R | IgG2 | insert R after A235 (+L328R) | PAPPVARGP |
| V234#/L328R | IgG2 | delete V234 (+L328R) | PAPPAGP |
| A235#/L328R | IgG2 | delete A235 (+L328R) | PAPPVGP |
| G237#/L328R | IgG2 | delete G237 (+L328R) | PAPPVAP |

FIG. 6

| Modification(s) | IgG | K_D (M) | | | | | |
|---|---|---|---|---|---|---|---|
| | | FcγRI | H131 FcγRIIa | R131 FcγRIIa | FcγRIIb | V158 FcγRIIIa | F158 FcγRIIIa |
| WT | IgG1 | 2.76 E-10 | 6.31 E-07 | 7.59 E-07 | 2.63 E-06 | 2.63 E-07 | 1.91 E-06 |
| WT | IgG2 | NB | 5.25 E-07 | 4.27 E-06 | NB | NB | NB |
| serum | IgG3 | 8.71 E-10 | 6.03 E-07 | 7.08 E-07 | 2.34 E-06 | 3.24 E-07 | 3.89 E-06 |
| WT | IgG4 | 8.32 E-09 | Weak | 4.07 E-06 | 2.00 E-06 | Weak | NB |
| G236R/L328R | IgG1 | NB | NB | NB | NB | NB | NB |
| L235G/G236R | IgG1 | 7.59 E-07 | NB | NB | NB | NB | NB |
| N325A/L328R | IgG1 | 1.12 E-07 | NB | NB | NB | NB | NB |
| N325L/L328R | IgG1 | 6.46 E-08 | NB | NB | NB | NB | NB |
| G237# | IgG1 | NB | | | | | |
| G236#/G237# | IgG1 | NB | NB | NB | NB | NB | NB |
| ^236R | IgG1 | 6.61 E-09 | | | | | |
| ^237R | IgG1 | NB | NB | NB | NB | NB | NB |
| ^237RR | IgG1 | NB | | | | | |
| G237#/L328R | IgG1 | NB | NB | NB | NB | NB | NB |
| G236#/G237#/L328R | IgG1 | NB | | | | | |
| ^236R/L328R | IgG1 | NB | NB | NB | NB | NB | NB |
| ^237R/L328R | IgG1 | NB | NB | NB | NB | NB | NB |
| ^237RR/L328R | IgG1 | NB | | | | | |
| L328R | IgG2 | NB | NB | NB | NB | NB | NB |
| ^235R | IgG2 | NB | NB | NB | NB | NB | NB |
| V234# | IgG2 | NB | | | | | |
| A235# | IgG2 | NB | NB | NB | NB | NB | NB |
| G237# | IgG2 | NB | NB | NB | NB | NB | NB |
| ^235R/L328R | IgG2 | NB | NB | NB | NB | NB | NB |
| V234#/L328R | IgG2 | NB | | | | | |
| A235#/L328R | IgG2 | NB | NB | NB | NB | NB | NB |
| G237#/L328R | IgG2 | NB | NB | NB | NB | NB | NB |

FIG. 13a

| Insertions | Deletions |
|---|---|
| after 233 | 233 |
| after 234 | 234 |
| after 235 | 235 |
| after 236 | 236 |
| after 237 | 237 |

FIG. 13b

| Position | Substitution(s) |
|---|---|
| 235 | G |
| 236 | R |
| 237 | K |
| 325 | A L |
| 328 | R |

FIG. 14

| Modification(s)<br># = deletion<br>^ = insertion after | IgG | Insertion/Deletion Description | Hinge 230-238 |
|---|---|---|---|
| WT IgG1 | IgG1 | | PAPELLGGP |
| WT IgG2 | IgG2 | | PAPPVAGP |
| S239D/I332E | IgG1 | | PAPELLGGP |
| S239D/I332E | IgG2 | | PAPPVAGP |
| P233E/V234L/A235L/^235G/S239D/I332E | IgG2 | insert G after 235 | PAPELLGGP |
| P233E/V234L/A235L/^235G/G327A | IgG2 | insert G after 235 | PAPELLGGP |
| P233E/V234L/A235L/^235G/S239D/I332E/G327A | IgG2 | insert G after 235 | PAPELLGGP |
| S239D/I332E/G327A | IgG2 | | PAPELLGGP |
| S239D/I332E/^V234L | IgG2 | insert L after 234 | PAPPVLAGP |
| S239D/I332E/^P233L | IgG2 | insert L after 233 | PAPPLVAGP |
| S239D/I332E/^P233EL | IgG2 | insert E & L after 233 | PAPPELVAGP |

FIG. 15a

| Variant | FcγRI | H131 FcγRIIa | R131 FcγRIIa | FcγRIIb | V158 FcγRIIIa | F158 FcγRIIIa |
|---|---|---|---|---|---|---|
| IgG1 WT | 2.76 E-10 | 6.31 E-07 | 7.59 E-07 | 2.63 E-06 | 2.63 E-07 | 1.91 E-06 |
| IgG2 WT | NB | 5.25 E-07 | 4.27 E-06 | NB | NB | NB |
| IgG1_S239D/I332E | 1.03 E-10 | 1.37 E-07 | 1.16 E-07 | 1.85 E-07 | 6.88 E-09 | 1.99 E-08 |
| IgG2_P233E/V234L/A235L/^235G/S239D/I332E | 9.08 E-11 | 6.83 E-08 | 6.85 E-08 | 8.42 E-08 | 1.24 E-08 | 5.02 E-08 |
| IgG2_P233E/V234L/A235L/^235G/G327A | 1.45 E-10 | 3.13 E-07 | 2.60 E-07 | 6.63 E-07 | 7.36 E-08 | 6.94 E-05 |
| IgG2_P233E/V234L/A235L/^235G/S239D/I332E/G327A | 1.30 E-10 | 1.27 E-07 | 6.39 E-08 | 1.01 E-07 | 4.30 E-09 | 1.25 E-08 |
| IgG2_S239D/I332E | 2.42 E-08 | 1.60 E-07 | 1.28 E-07 | 6.82 E-07 | 3.03 E-08 | 8.17 E-08 |
| IgG2_S239D/I332E/G327A | 1.32 E-08 | 1.22 E-07 | 1.61 E-07 | 2.32 E-07 | 1.94 E-08 | 3.63 E-08 |
| IgG2_S239D/I332E/^V234L | 6.34 E-10 | 2.90 E-08 | 2.78 E-08 | 9.58 E-08 | 3.37 E-08 | 9.62 E-08 |
| IgG2_S239D/I332E/^P233L | 3.28 E-09 | 8.22 E-08 | 6.74 E-08 | 2.38 E-07 | 2.52 E-08 | 5.32 E-08 |
| IgG2_S239D/I332E/^P233EL | 1.94 E-09 | 7.18 E-08 | 6.42 E-08 | 2.64 E-07 | 2.16 E-08 | 5.96 E-08 |

FIG. 15b

| Variant | H IIa : IIb | R IIa : IIb | V IIIa : IIb | F IIIa : IIb |
|---|---|---|---|---|
| IgG1 WT | 4.17 | 3.47 | 10.00 | 1.38 |
| IgG2 WT | | | | |
| IgG1_S239D/I332E | 1.35 | 1.59 | 26.89 | 9.30 |
| IgG2_P233E/V234L/A235L/^235G/S239D/I332E | 1.23 | 1.23 | 6.79 | 1.68 |
| IgG2_P233E/V234L/A235L/^235G/G327A | 2.12 | 2.55 | 9.01 | 0.01 |
| IgG2_P233E/V234L/A235L/^235G/S239D/I332E/G327A | 0.80 | 1.58 | 23.49 | 8.08 |
| IgG2_S239D/I332E | 4.26 | 5.33 | 22.51 | 8.35 |
| IgG2_S239D/I332E/G327A | 1.90 | 1.44 | 11.96 | 6.39 |
| IgG2_S239D/I332E/^V234L | 3.30 | 3.45 | 2.84 | 1.00 |
| IgG2_S239D/I332E/^P233L | 2.90 | 3.53 | 9.44 | 4.47 |
| IgG2_S239D/I332E/^P233EL | 3.68 | 4.11 | 12.22 | 4.43 |

Figure 18a

| Insertions | Deletions |
|---|---|
| after 233 | 233 |
| after 234 | 234 |
| after 235 | 235 |
| after 236 | 236 |
| after 237 | 237 |

Figure 18b

| Position | Substitution(s) |
|---|---|
| 234 | G I |
| 235 | D E I Y |
| 236 | A S |
| 239 | D E |
| 243 | L |
| 247 | L |
| 255 | L |
| 267 | D E Q |
| 268 | D E |
| 270 | E |
| 280 | H Q Y |
| 292 | P |
| 293 | R |
| 295 | E |
| 298 | A T N |
| 300 | L |
| 305 | I |
| 324 | G I |
| 326 | A D E W Y |
| 327 | H |
| 328 | A F I |
| 330 | I L Y V |
| 332 | D E |
| 333 | A S |
| 334 | A L |
| 392 | T |
| 396 | L |
| 421 | K |

FIG. 19
FIG. 19a (SEQ ID NO: 5)

Anti-CD20 variable light chain (VL)

DIQMTQSPSSLSASVGDRVTITCRASSSVSYMHWYQQKPGKAPKPLIYAPSNLASGVPSRF
SGSGSGTDFTLTISSLQPEDFATYYCQQWSFNPPTFGQGTKVEIK

FIG. 19b (SEQ ID NO: 6)

Anti-CD20 variable heavy chain (VH)

EVQLVESGGGLVQPGGSLRLSCAASGYTFTSYNMHWVRQAPGKGLEWVGAIYPGNGDTS
YNQKFKGRFTISVDKSKNTLYLQMNSLRAEDTAVYYCARVVYYSNSYWYFDVWGQGTLVT
VSS

FIG. 19c (SEQ ID NO: 7)

Anti-Her2 variable light chain (VL)

DIQMTQSPSSLSASVGDRVTITCRASQDVNTAVAWYQQKPGKAPKLLIYSASFLYSGVPSR
FSGSRSGTDFTLTISSLQPEDFATYYCQQHYTTPPTFGQGTKVEIK

FIG. 19d (SEQ ID NO: 8)

Anti-Her2 heavy chain (VH)

EVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVS
S

FIG. 19e (SEQ ID NO: 9)

Anti-CTLA-4 variable light chain (VL)

EIVLTQSPGTLSLSPGERATLSCRASQSVGSSYLAWYQQKPGQAPRLLIYGAFSRATGIPDR
FSGSGSGTDFTLTISRLEPEDFAVYYCQQYGSSPWTFGQGTKVEIK

FIG. 19f (SEQ ID NO: 10)

Anti-CTLA-4 variable heavy chain (VH)

QVQLVESGGGVVQPGRSLRLSCAASGFTFSSYTMHWVRQAPGKGLEWVTFISYDGNNKY
YADSVKGRFTISRDNSKNTLYLQMNSLRAEDTAIYYCARTGWLGPFDYWGQGTLVTVSS

FIG. 20
FIG. 20a (SEQ ID NO: 11)

Kappa constant light chain (Cκ)

RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

FIG. 20b (SEQ ID NO: 12)

IgG1 constant heavy chain (CH1-hinge-CH2-CH3)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGN
VFSCSVMHEALHNHYTQKSLSLSPGK

FIG. 20c (SEQ ID NO: 13)

IgG2 constant heavy chain (CH1-hinge-CH2-CH3)

ASTKGPSVFPLAPCSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAPPVAGPSVFLF
PPKPKDTLMISRTPEVTCVVVDVSHEDPEVQFNWYVDGVEVHNAKTKPREEQFNSTFRVV
SVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFS
CSVMHEALHNHYTQKSLSLSPGK

FIG. 20d (SEQ ID NO: 14)

IgG3 constant heavy chain (CH1-hinge-CH2-CH3)

ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRVELKTPLGDTTHTCPRCPEPKSCD
TPPPCPRCPEPKSCDTPPPCPRCPEPKSCDTPPPCPRCPAPELLGGPSVFLFPPKPKDTL
MISRTPEVTCVVVDVSHEDPEVQFKWYVDGVEVHNAKTKPREEQYNSTFRVVSVLTVLHQ
DWLNGKEYKCKVSNKALPAPIEKTISKTKGQPREPQVYTLPPSREEMTKNQVSLTCLVKGF
YPSDIAVEWESSGQPENNYNTTPPMLDSDGSFFLYSKLTVDKSRWQQGNIFSCSVMHEAL
HNRFTQKSLSLSPGK

FIG. 20e (SEQ ID NO: 15)

IgG4 constant heavy chain (CH1-hinge-CH2-CH3)

ASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPSCPAPEFLGGPSVFL
FPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVF
SCSVMHEALHNHYTQKSLSLSLGK

SEQUENCE LISTING

<160> NUMBER OF SEQ ID NOS: 20

<210> SEQ ID NO 1
<211> LENGTH: 106
<212> TYPE: PRT
<213> ORGANISM: Artificial
<220> FEATURE:
<223> OTHER INFORMATION: Synthetic

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30
```

-continued

His Trp Tyr Gln Gln Lys Pro Gly Lys Ala Pro Lys Pro Leu Ile Tyr
                35                  40                  45

Ala Pro Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys
            100                 105

<210> SEQ ID NO 2
<211> LENGTH: 122
<212> TYPE: PRT
<213> ORGANISM: Artificial
<220> FEATURE:
<223> OTHER INFORMATION: Synthetic

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
                20                  25                  30

Asn Met His Trp Val Arg Gln Ala Pro Gly Lys Gly Leu Glu Trp Val
                35                  40                  45

Gly Ala Ile Tyr Pro Gly Asn Gly Asp Thr Ser Tyr Asn Gln Lys Phe
        50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
                100                 105                 110

Gly Gln Gly Thr Leu Val Thr Val Ser Ser
            115                 120

<210> SEQ ID NO 3
<211> LENGTH: 107
<212> TYPE: PRT
<213> ORGANISM: Artificial
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

-continued

```
<210> SEQ ID NO 4
<211> LENGTH: 120
<212> TYPE: PRT
<213> ORGANISM: Artificial
<220> FEATURE:
<223> OTHER INFORMATION: Synthetic

<400> SEQUENCE: 4

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 5
<211> LENGTH: 108
<212> TYPE: PRT
<213> ORGANISM: Artificial
<220> FEATURE:
<223> OTHER INFORMATION: Synthetic

<400> SEQUENCE: 5

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 6
<211> LENGTH: 118
<212> TYPE: PRT
<213> ORGANISM: Artificial
<220> FEATURE:
<223> OTHER INFORMATION: Synthetic

<400> SEQUENCE: 6

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30
```

Thr Met His Trp Val Arg Gln Ala Pro Gly Lys Gly Leu Glu Trp Val
            35                  40                  45

Thr Phe Ile Ser Tyr Asp Gly Asn Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                 85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 7
<211> LENGTH: 107
<212> TYPE: PRT
<213> ORGANISM: Artificial
<220> FEATURE:
<223> OTHER INFORMATION: Synthetic

<400> SEQUENCE: 7

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 8
<211> LENGTH: 330
<212> TYPE: PRT
<213> ORGANISM: Artificial
<220> FEATURE:
<223> OTHER INFORMATION: Synthetic

<400> SEQUENCE: 8

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 326
<212> TYPE: PRT
<213> ORGANISM: Artificial
<220> FEATURE:
<223> OTHER INFORMATION: Synthetic

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 10
<211> LENGTH: 377
<212> TYPE: PRT
<213> ORGANISM: Artificial
<220> FEATURE:
<223> OTHER INFORMATION: Synthetic

<400> SEQUENCE: 10

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val

```
                        180                 185                 190
Val Val Asp Val Ser His Glu Asp Pro Glu Val Gln Phe Lys Trp Tyr
                195                 200                 205
Val Asp Gly Val Glu Val His Asn Ala Lys Thr Lys Pro Arg Glu Glu
            210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
        290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
        355                 360                 365
Lys Ser Leu Ser Leu Ser Pro Gly Lys
        370                 375

<210> SEQ ID NO 11
<211> LENGTH: 327
<212> TYPE: PRT
<213> ORGANISM: Artificial
<220> FEATURE:
<223> OTHER INFORMATION: Synthetic

<400> SEQUENCE: 11

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 12
<211> LENGTH: 330
<212> TYPE: PRT
<213> ORGANISM: Artificial
<220> FEATURE:
<223> OTHER INFORMATION: Synthetic

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Phe Asn Ser Thr Phe Arg Val Val Ser Val Leu Thr Val Val
        180                 185                 190

His Gln Asp Trp Leu Asn Gly Lys Glu Tyr Lys Cys Lys Val Ser Asn
    195                 200                 205
```

```
Lys Gly Leu Pro Ala Pro Ile Glu Lys Thr Ile Ser Lys Thr Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 215
<212> TYPE: PRT
<213> ORGANISM: Artificial
<220> FEATURE:
<223> OTHER INFORMATION: Synthetic

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 14
<211> LENGTH: 448
<212> TYPE: PRT
```

<213> ORGANISM: Artificial
<220> FEATURE:
<223> OTHER INFORMATION: Synthetic

<400> SEQUENCE: 14

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Gly Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 15
<211> LENGTH: 444
<212> TYPE: PRT
<213> ORGANISM: Artificial
<220> FEATURE:
<223> OTHER INFORMATION: Synthetic

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

```
Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
        340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 16
<211> LENGTH: 330
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (117)..(117)
<223> OTHER INFORMATION: Xaa can be Leucine, Glycine or Histidine
<220> FEATURE:
<221> NAME/KEY: MISC_FEATURE
<222> LOCATION: (118)..(118)
<223> OTHER INFORMATION: Xaa can be Leucine, Aspartic Acid, Glycine or
      Histidine
<220> FEATURE:
<221> NAME/KEY: MISC_FEATURE
<222> LOCATION: (119)..(119)
<223> OTHER INFORMATION: Xaa can be Glycine, Isoleucine, Asparagine,
      Proline or Arginine
<220> FEATURE:
<221> NAME/KEY: MISC_FEATURE
<222> LOCATION: (120)..(120)
<223> OTHER INFORMATION: Xaa can be Glycine, Lysine or Leucine
<220> FEATURE:
<221> NAME/KEY: MISC_FEATURE
<222> LOCATION: (150)..(150)
<223> OTHER INFORMATION: Xaa can be Serine or Arginine
<220> FEATURE:
<221> NAME/KEY: MISC_FEATURE
<222> LOCATION: (152)..(152)
<223> OTHER INFORMATION: Xaa can be Glutamic Acid or Arginine
<220> FEATURE:
<221> NAME/KEY: MISC_FEATURE
<222> LOCATION: (208)..(208)
<223> OTHER INFORMATION: Xaa can be Asparagine, Alanine or Leucine
<220> FEATURE:
<221> NAME/KEY: MISC_FEATURE
<222> LOCATION: (211)..(211)
<223> OTHER INFORMATION: Xaa can be Leucine or Arginine

<400> SEQUENCE: 16

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Xaa Xaa Xaa Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Xaa His Xaa Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Xaa
        195                 200                 205

Lys Ala Xaa Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 330
<212> TYPE: PRT
<213> ORGANISM: Homo sapiens

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 326
<212> TYPE: PRT
<213> ORGANISM: Homo sapiens

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

-continued

```
Val Glu Val His Asn Ala Lys Thr Lys Pro Arg Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 19
<211> LENGTH: 377
<212> TYPE: PRT
<213> ORGANISM: Homo sapiens

<400> SEQUENCE: 19

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205
```

Val Asp Gly Val Glu Val His Asn Ala Lys Thr Lys Pro Arg Glu Glu
    210                 215                 220

Gln Tyr Asn Ser Thr Phe Arg Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 20
<211> LENGTH: 327
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

```
                    -continued
Pro Ser Ser Ile Glu Lys Thr Ile Ser Lys Ala Lys Gly Gln Pro Arg
    210             215             220

Glu Pro Gln Val Tyr Thr Leu Pro Pro Ser Gln Glu Met Thr Lys
225             230             235             240

Asn Gln Val Ser Leu Thr Cys Leu Val Lys Gly Phe Tyr Pro Ser Asp
            245             250             255

Ile Ala Val Glu Trp Glu Ser Asn Gly Gln Pro Glu Asn Asn Tyr Lys
            260             265             270

Thr Thr Pro Pro Val Leu Asp Ser Asp Gly Ser Phe Phe Leu Tyr Ser
        275             280             285

Arg Leu Thr Val Asp Lys Ser Arg Trp Gln Glu Gly Asn Val Phe Ser
    290             295             300

Cys Ser Val Met His Glu Ala Leu His Asn His Tyr Thr Gln Lys Ser
305             310             315             320

Leu Ser Leu Ser Leu Gly Lys
                325
```

US 8,399,618 B2

IMMUNOGLOBULIN INSERTIONS, DELETIONS, AND SUBSTITUTIONS

This application is a continuation of U.S. application Ser. No. 12/020,443, filed Jan. 25, 2008, U.S. Ser. No. 12/020,443 claims benefit under 35 U.S.C. §119(e) to U.S. Ser. No. 60/886,635, filed Jan. 25, 2007; and is contination-in-part of U.S. Ser. No. 11/396,495, filed Mar. 31, 2006; a continuation-in-part of U.S. Ser. No. 11/256,060, filed Oct. 21, 2005; U.S. Ser. No. 11/256,060 claims benefit under 35 U.SC. §119(e) to U.S. Ser. No. 60/659,004, filed Mar. 3, 2005; U.S. Ser. No. 60/652,968, filed Feb. 14, 2005; U.S. Ser. No. 60/629,068, filed Nov. 18, 2004; and U.S. Ser. No. 60/621,387, filed Oct. 21, 2004, all of which are incorporated herein by reference in their entirety.

FIELD OF THE INVENTION

The present invention relates to novel immunoglobulin insertions, deletions, and substitutions that provide optimized effector function properties, engineering methods for their generation, and their application, particularly for therapeutic purposes.

BACKGROUND OF THE INVENTION

Antibodies are immunological proteins that bind a specific antigen. Generally, antibodies are specific for targets, have the ability to mediate immune effector mechanisms, and have a long half-life in serum. Such properties make antibodies powerful therapeutics. Monoclonal antibodies are used therapeutically for the treatment of a variety of conditions including cancer, infectious disease, autoimmune disease, and inflammatory disorders. There are currently over ten antibody products on the market and hundreds in development.

Antibodies have found widespread application in oncology, particularly for targeting cellular antigens selectively expressed on tumor cells with the goal of cell destruction. There are a number of mechanisms by which antibodies destroy tumor cells, including anti-proliferation via blockage of needed growth pathways, intracellular signaling leading to apoptosis, enhanced down regulation and/or turnover of receptors, CDC, ADCC, ADCP, and promotion of an adaptive immune response (Cragg et al., 1999, Curr Opin Immunol 11:541-547; Glennie et al., 2000, Immunol Today 21:403-410, both hereby entirely incorporated by reference). Anti-tumor efficacy may be due to a combination of these mechanisms, and their relative importance in clinical therapy appears to be cancer dependent.

Despite this arsenal of anti-tumor weapons, the potency of antibodies as anti-cancer agents is unsatisfactory, particularly given their high cost. Patient tumor response data show that monoclonal antibodies provide only a small improvement in therapeutic success over normal single-agent cytotoxic chemotherapeutics. For example, just half of all relapsed low-grade non-Hodgkin's lymphoma patients respond to the anti-CD20 antibody rituximab (McLaughlin et al., 1998, J Clin Oncol 16:2825-2833, hereby entirely incorporated by reference). Of 166 clinical patients, 6% showed a complete response and 42% showed a partial response, with median response duration of approximately 12 months. Trastuzumab (Herceptin™, Genentech), an anti-HER2/neu antibody for treatment of metastatic breast cancer, has less efficacy. The overall response rate using trastuzumab for the 222 patients tested was only 15%, with 8 complete and 26 partial responses and a median response duration and survival of 9 to 13 months (Cobleigh et al., 1999, J Clin Oncol 17:2639-2648, hereby entirely incorporated by reference). Currently for anticancer therapy, any small improvement in mortality rate defines success. Thus there is a significant need to enhance the capacity of antibodies to destroy targeted cancer cells.

One potential way to improve the activity of anti-cancer therapeutics is to optimize their affinity and/or selectivity for Fc gamma receptors (FcγRs). Because all FcγRs interact with the same binding site on Fc, and because of the high homology among the FcγRs, obtaining variants that selectively increase or reduce FcγR affinity is a major challenge. Thus there is a need to make Fc variants that selectively increase or reduce FcγR affinity.

In contrast to antibody therapeutics and indications wherein effector functions contribute to clinical efficacy, for some antibodies and clinical applications it may be favorable to reduce or eliminate binding to one or more FcγRs, or reduce or eliminate one or more FcγR- or complement-mediated effector functions including but not limited to ADCC, ADCP, and/or CDC. This is often the case for therapeutic antibodies whose mechanism of action involves blocking or antagonism but not killing of the cells bearing target antigen. In these cases depletion of target cells is undesirable and can be considered a side effect. For example, the ability of anti-CD4 antibodies to block CD4 receptors on T cells makes them effective anti-inflammatories, yet their ability to recruit FcγR receptors also directs immune attack against the target cells, resulting in T cell depletion (Reddy et al., 2000, J Immunol 164:1925-1933, incorporated entirely by reference). Effector function may also be a problem for radiolabeled antibodies, referred to as radioconjugates, and antibodies conjugated to toxins, referred to as immunotoxins. These drugs can be used to destroy cancer cells, but the recruitment of immune cells via Fc interaction with FcγRs brings healthy immune cells in proximity to the deadly payload (radiation or toxin), resulting in depletion of normal lymphoid tissue along with targeted cancer cells (Hutchins et al., 1995, Proc Natl Acad Sci USA 92:11980-11984; White et al., 2001, Annu Rev Med 52:125-145, both incorporated entirely by reference). What is needed is a general and robust means to completely ablate all FcγR binding and FcγR- and complement-mediated effector functions. These and other needs are addressed by the present invention.

SUMMARY OF THE INVENTION

The present invention is directed to an Fc variant of a parent Fc polypeptide, wherein said Fc variant comprises amino modifications, which can comprise independently or in combination amino acid insertion(s), amino acid deletion(s) and/or amino acid substitutions, particularly in the Fc region of said parent Fc polypeptide.

In one aspect of the invention, the Fc variant of the invention comprises an amino acid insertion after a position selected from the group consisting of 233, 234, 235, 236, and 237, wherein numbering is according to the EU index. The Fc variant may additionally comprise an amino acid substitution in the Fc region. In one embodiment, said substitution occurs at a position selected from the group consisting of 235, 236, 237, 325, and 328, wherein numbering is according to the EU index. In a preferred embodiment, said substitution is selected from the group consisting of 235G, 236R, 237K, 325L, 325A, and 328R. In another embodiment, said substitution occurs at a position selected from the group consisting of 234, 235, 236, 239, 243, 247, 255, 267, 268, 270, 280, 292, 293, 295, 298, 300, 305, 324, 326, 327, 328, 330, 332, 333, 334, 392, 396, and 421, wherein numbering is according to the EU index. In a preferred embodiment, said substitution is selected from the group consisting of 234G, 234I, 235D, 235E, 235I, 235Y, 236A, 236S, 239D, 239E, 243L, 247L, 255L, 267D, 267E, 267Q, 268D, 268E, 270E, 280H, 280Q, 280Y, 292P, 293R, 295E, 298A, 298T, 298N, 300L, 305I, 324G, 324I, 326A, 326D, 326E, 326W, 326Y, 327H, 328A, 328F, 328I, 330I, 330L, 330Y, A330V, 332D, 332E, 333A, 333S, 334A, 334L, 392T, 396L, and 421K.

In another aspect of the invention, the Fc variant of the invention comprises an amino acid deletion at a position selected from the group consisting of 233, 234, 235, 236, and 237, wherein numbering is according to the EU index. The Fc variant may additionally comprise an amino acid substitution in the Fc region. In one embodiment, said substitution occurs at a position selected from the group consisting of 235, 236, 237, 325, and 328, wherein numbering is according to the EU index. In a preferred embodiment, said substitution is selected from the group consisting of 235G, 236R, 237K, 325L, 325A, and 328R. In another embodiment, said substitution occurs at a position selected from the group consisting of 234, 235, 236, 239, 243, 247, 255, 267, 268, 270, 280, 292, 293, 295, 298, 300, 305, 324, 326, 327, 328, 330, 332, 333, 334, 392, 396, and 421, wherein numbering is according to the EU index. In a preferred embodiment, said substitution is selected from the group consisting of 234G, 234I, 235D, 235E, 235I, 235Y, 236A, 236S, 239D, 239E, 243L, 247L, 255L, 267D, 267E, 267Q, 268D, 268E, 270E, 280H, 280Q, 280Y, 292P, 293R, 295E, 298A, 298T, 298N, 300L, 305I, 324G, 324I, 326A, 326D, 326E, 326W, 326Y, 327H, 328A, 328F, 328I, 330I, 330L, 330Y, A330V, 332D, 332E, 333A, 333S, 334A, 334L, 392T, 396L, and 421K.

In a preferred embodiment of the invention, the Fc variant alters binding to one or more FcγRs. In one aspect, said Fc variant reduces affinity to a human FcγR. In another aspect, said Fc variant improves affinity to a human FcγR.

The present invention provides novel Fc polypeptides, including antibodies, Fc fusions, isolated Fc, and Fc fragments, that comprise the Fc variants disclosed herein. The novel Fc polypeptides may find use in a therapeutic product. In certain embodiments, the Fc polypeptides of the invention are antibodies.

In one aspect of the invention, the Fc variant of the invention composes an antibody that is a human IgG1, IgG2, or IgG4 antibody.

The present invention provides isolated nucleic acids encoding the Fc variants described herein. The present invention provides vectors comprising the nucleic acids, optionally, operably linked to control sequences. The present invention provides host cells containing the vectors, and methods for producing and optionally recovering the Fc variants.

The present invention provides compositions comprising Fc polypeptides that comprise the Fc variants described herein, and a physiologically or pharmaceutically acceptable carrier or diluent.

The present invention contemplates therapeutic and diagnostic uses for Fc polypeptides that comprise the Fc variants disclosed herein. The Fc polypeptides described by the invention may be used to treat a variety of indications, including but not limited to cancers, infectious diseases, autoimmune disorders, an infectious diseases.

BRIEF DESCRIPTION OF THE DRAWINGS

FIG. 1 [SEQ ID NOS. 1-4]. Alignment of the amino acid sequences of the human IgG immunoglobulins IgG1, IgG2, IgG3, and IgG4. FIG. 1a provides the sequences of the CH1 (Cγ1) and hinge domains, and FIG. 1b provides the sequences of the CH2 (Cγ2) and CH3 (Cγ3) domains. Positions are numbered according to the EU index of the IgG1 sequence, and differences between IgG1 and the other immunoglobulins IgG2, IgG3, and IgG4 are shown in gray. Allotypic polymorphisms exist at a number of positions, and thus slight differences between the presented sequences and sequences in the prior art may exist. The possible beginnings of the Fc region are labeled, defined herein as either EU position 226 or 230.

FIGS. 2a and 2b. Common haplotypes of the human gamma1 (FIG. 2a) and gamma2 (FIG. 2b) chains.

FIGS. 3a and 3b. FIG. 3a provides an illustration of the hinge region and sites of engineering. Gray indicates the C-terminus of the CH1 domain (left) and N-terminus of the CH2 domain (right). Bold indicates residues in the hinge and N-terminal CH2 domain, 233-238, that interact with FcγRs according to the structure of the human Fc/FcγRIIIb complex (pdb 1E4K, Sondermann et al., 2000, Nature 406:267-273). FIG. 3b shows the structured domains (CH2 and CH3) of the Fc region (pdb 1 DN2, DeLano et al., 2000, Science 287: 1279-1283). The first residues involved in the structured CH2 region, G237 and P238, are shown as black sticks. The carbohydrate attached at N297 is shown as black lines.

FIG. 4. Library of antibody Fc variants screened for reduced FcγR affinity and effector function. # indicates a deletion of the designated residue, and ˆ indicates an insertion of the designated amino acid after the designated position. A description of insertions and deletions is provided for each variant, and the amino acid sequence from EU positions 230-238 is provided.

FIG. 5a shows the binding of anti-Her2 WT IgG1 antibody to human FcγRs FcγRI, H131 and R131 FcγRIIa, FcγRIIb, and V158 and F158 FcγRIIIa. Binding was measured at 5 concentrations of receptor. FIG. 5b shows the sensorgram for the highest receptor concentration for binding of select antibodies and antibody variants to each FcγR.

FIG. 6. Table of affinities for binding of WT IgG and Fc variant antibodies to human FcγRs as determined by Biacore. The equilibrium dissociation constant ($K_D$) for binding of each variant to each FcγR is provided where tested. "NB"=no binding detected; "Weak"=binding observed but not fittable to an accurate $K_D$. A blank cell indicates that the receptor was not tested for that particular variant.

FIGS. 13a and 13b. Preferred modifications of the invention for reducing FcγR- and/or complement-mediated effector function. FIG. 13a shows positions at which insertions and deletions may be constructed. FIG. 13b shows positions and substitutions that may be combined with the modifications provided in FIG. 13a. However, as outlined herein, FIG. 13 is not meant to be limiting, and any amino acid modification described herein or in the applications incorporated by reference can be combined independently with any other(s).

FIG. 14. Library of antibody Fc variants screened for selective FcγR affinity and optimized effector function. # indicates a deletion of the designated residue, and ^ indicates an insertion of the designated amino acid after the designated position. A description of insertions and deletions is provided for each variant, and the amino acid sequence from 230-238 is provided.

FIGS. 15a and 15b. FIG. 15a provides the affinities for binding of WT IgG and Fc variant antibodies to human FcγRs as determined by Biacore. The equilibrium dissociation constant ($K_D$) for binding of each variant to each FcγR is provided where tested. "NB"=no binding detected. FIG. 15b provides the activating:inhibitory ratios for two activating receptors, FcγRIIa (H131 and R131 isoforms) and FcγRIIIa (V1158 and F158 isoforms) relative to the inhibitory receptor FcγRIIb. These ratios were calculated by dividing the $K_D$ for FcγRIIb by the $K_D$ for the activating receptor.

FIGS. 18a and 18b. Preferred modifications of the invention for engineering selectively optimized FcγR affinity. FIG. 18a shows positions at which insertions and deletions may be constructed. FIG. 18b shows positions and substitutions that may be combined with the modifications provided in FIG. 18a.

FIGS. 19a-19f [SEQ ID NOS. 5-10]. Amino acid sequences of variable light (VL) and heavy (VH) chains used in the present invention, including PRO70769 (FIGS. 19a and 19b), trastuzumab (FIGS. 19c and 19d), and ipilimumab (FIGS. 19e and 19f).

FIGS. 20a-20e [SEQ ID NOS. 11-15. Amino acid sequences of human constant light kappa (FIG. 20a) and heavy (FIGS. 20b-20e) chains used in the present invention.

DETAILED DESCRIPTION OF THE INVENTION

Figure 3B:
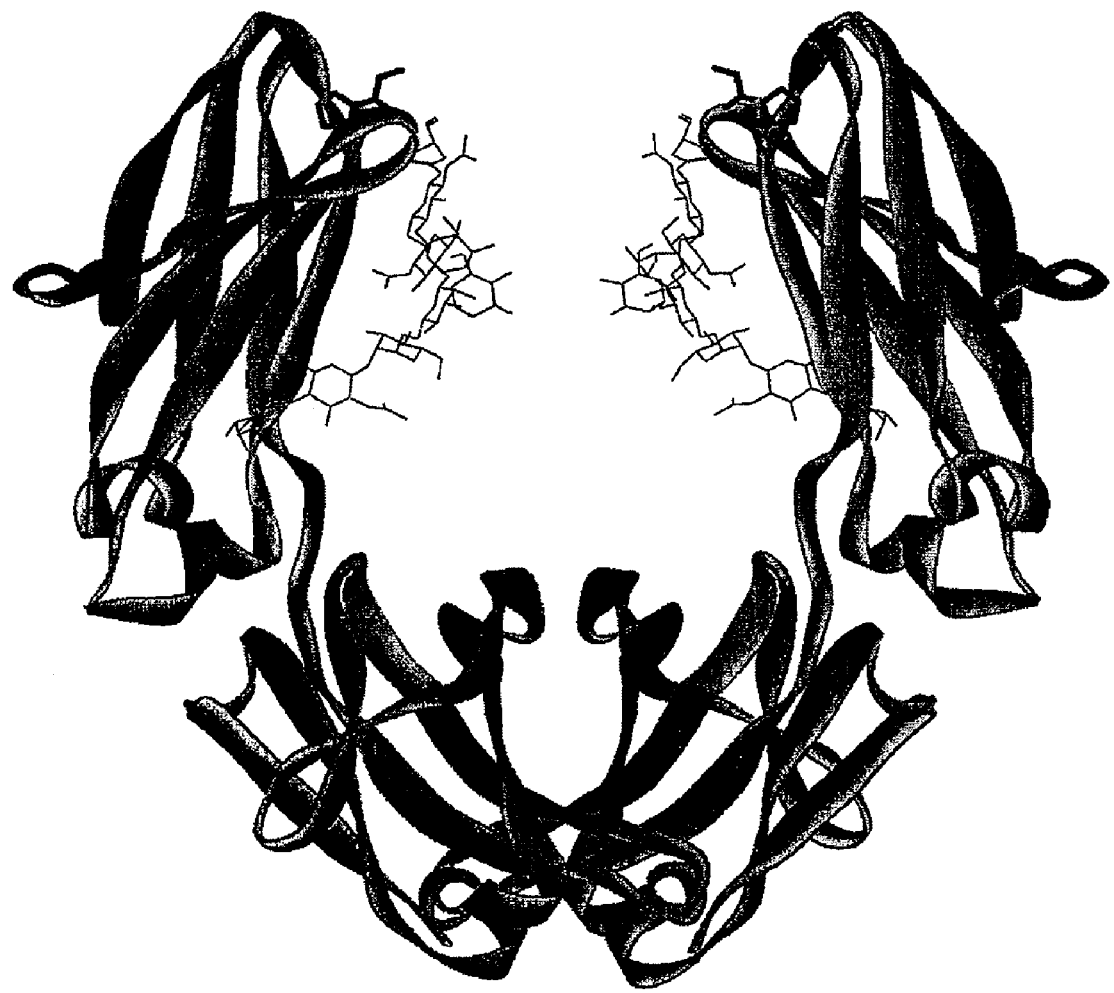

The present invention is directed to proteins comprising altered Fc regions that exhibit altered functionality, including differential binding to one or more Fcγ receptors as compared to a non-altered Fc region. In a particular embodiment, the variants reduce functionality, leading to desirable biological properties. The variants can include one or more insertions of an amino acid, one or more deletions, and/or one or more amino acid substitutions, as outlined herein.

Specifically, amino acid variations outlined in U.S. Ser. No. 10/672,280, 10/822,231, 11/124,620, 11/174,287, 11/396,495; 11/538,406, 11/538,411 and 60/886,635 include a variety of disclosures, all of which are expressly incorporated by reference herein, and in particular for the disclosure of positions, particular substitutions, data and the figures.

In addition, each modification outlined herein can be done independently or in combination with any other modification(s), and can be done on the Fc region of any or all of IgG1, IgG2, IgG3 and/or IgG4.

Definitions

In order that the invention may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "antibody" herein is meant a protein consisting of one or more polypeptides substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (υ), delta (δ), gamma (γ), sigma (σ), and alpha (α) which encode the IgM, IgD, IgG (IgG1, IgG2, IgG3, and IgG4), IgE, and IgA (IgA1 and IgA2) isotypes respectively. Antibody herein is meant to include full length antibodies and antibody fragments, and may refer to a natural antibody from any organism, an engineered antibody, or an antibody generated recombinantly for experimental, therapeutic, or other purposes. Additional description and definition of "antibody", including for example "humanized", "chimeric", etc., is outlined below.

By "amino acid" and "amino acid identity" as used herein is meant one of the 20 naturally occurring amino acids or any non-natural analogues that may be present at a specific, defined position.

By "CDC" or "complement dependent cytotoxicity" as used herein is meant the reaction wherein one or more complement protein components recognize bound antibody on a target cell and subsequently cause lysis of the target cell.

By "constant region" of an antibody as defined herein is meant the region of the antibody that is encoded by one of the light or heavy chain immunoglobulin constant region genes. By "constant light chain" or "light chain constant region" as used herein is meant the region of an antibody encoded by the kappa (Cκ) or lambda (Cλ) light chains. The constant light chain typically comprises a single domain, and as defined herein refers to positions 108-214 of Cκ or Cλ, wherein numbering is according to the EU index. By "constant heavy chain" or "heavy chain constant region" as used herein is meant the region of an antibody encoded by the mu, delta, gamma, alpha, or epsilon genes to define the antibody's isotype as IgM, IgD, IgG, IgA, or IgE, respectively. For full length IgG antibodies, the constant heavy chain, as defined herein, refers to the N-terminus of the CH1 domain to the C-terminus of the CH3 domain, thus comprising positions 118-447, wherein numbering is according to the EU index.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC.

By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys.

By "Fab" or "Fab region" as used herein is meant the polypeptides that comprise the $V_H$, CH1, $V_H$, and $C_L$ immunoglobulin domains. Fab may refer to this region in isolation, or this region in the context of a full length antibody or antibody fragment.

By "Fc" or "Fc region" or "Fc domain", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide such as an antibody or immunoadhesin (e.g. an Fc fusion protein), as described below. It should be noted that for the purposes described herein, "Fc region" generally includes the hinge region, comprising residues 230-238, unless noted otherwise. Thus, an "Fc variant" can include variants of the hinge region, in the presence or absence of additional amino acid modifications in the Cγ2 and Cγ3 domains.

By "Fc polypeptide" as used herein is meant a polypeptide that comprises all or part of an Fc region. Fc polypeptides include antibodies, Fc fusions (sometimes referred to as "Fc fusion proteins" or "immunoadhesins"), isolated Fcs, and Fc fragments.

By "Fc fusion" as used herein is meant a protein wherein one or more polypeptides is operably linked to Fc. Fc fusion is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200, both hereby entirely incorporated by reference). An Fc fusion combines the Fc region of an immunoglobulin with a fusion partner, which in general may be any protein, polypeptide or small molecule. The role of the non-Fc part of an Fc fusion, i.e., the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor that is implicated in disease.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, incorporated entirely by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "Fc ligand" or "Fc receptor" as used herein is meant a molecule, preferably a polypeptide, from any organism that binds to the Fc region of an antibody to form an Fc-ligand complex. Fc ligands include but are not limited to FcγRs, FcγRs, FcγRs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136). Fc ligands may include undiscovered molecules that bind Fc.

By "full length antibody" as used herein is meant the structure that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region.

By "IgG" as used herein is meant a polypeptide belonging to the class of antibodies that are substantially encoded by a recognized immunoglobulin gamma gene. In humans this IgG comprises the subclasses or isotypes IgG1, IgG2, IgG3, and IgG4. In mice IgG comprises IgG1, IgG2a, IgG2b, IgG3.

By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains.

By "immunoglobulin (Ig) domain" as used herein is meant a region of an immunoglobulin that exists as a distinct structural entity as ascertained by one skilled in the art of protein structure. Ig domains typically have a characteristic β-sandwich folding topology. The known Ig domains in the IgG isotype of antibodies ar VH Cγ1, Cγ2, Cγ3, VL, and CL.

By "IgG" or "IgG immunoglobulin" as used herein is meant a polypeptide belonging to the class of antibodies that are substantially encoded by a recognized immunoglobulin gamma gene. In humans this class comprises the subclasses or isotypes IgG1, IgG2, IgG3, and IgG4. By "isotype" as used herein is meant any of the subclasses of immunoglobulins defined by the chemical and antigenic characteristics of their constant regions. The known human immunoglobulin isotypes are IgG1, IgG2, IgG3, IgG4, IgA1, IgA2, IgM, IgD, and IgE.

By "modification" herein is meant an alteration in the physical, chemical, or sequence properties of a protein, polypeptide, antibody, or immunoglobulin. Preferred modifications of the invention are amino acid modifications and glycoform modifications.

By "amino acid modification" herein is meant an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution I332E refers to a variant polypeptide, in this case a constant heavy chain variant, in which the isoleucine at position 332 is replaced with glutamic acid. It should be noted that in some cases, the initial identification of the wild-type amino acid is not meant to be determinative; that is, "I332E" can also refer to a protein that contains an glutamic acid at position 332, even if the wild-type amino acid in the particular parent protein is not isoleucine. This can also be conveyed using "332E" language, for example. In addition, as is generally noted herein, multiple modifications, including multiple substitutions, can be made. In some embodiments, from 1, 2, 3, 4, 5, 6, 7, 8, 9 or 10 amino acid substitutions are done, with any range within being contemplated, in combination with one or more insertion(s) and/or one or more deletion(s).

By "amino acid insertion" or "insertion" as used herein is meant the addition of an amino acid at a particular position in a parent polypeptide sequence. An insertion as described herein is designated by the symbol "^", followed by the position, followed by the amino acid that is inserted. For example, ^236R designates an insertion of arginine after postion 236; "^236RR" depicts the insertion of two arginines after position 236, etc. For ease of reference, the original numbering after an insertion is not changed; that is, in a molecule containing an insertion, the amino acid normally found following the insertion site is still numbered as if the insertion did not occur, unless noted otherwise.

By "amino acid deletion" or "deletion" as used herein is meant the removal of an amino acid at a particular position in a parent polypeptide sequence. A deletion as described herein is designated by the symbol "#", preceded by the amino acid and position that are to be deleted. For example, G237# designates the deletion of glycine at position 237. For ease of reference, the original numbering after a deletion is not changed; that is, in a molecule containing a deletion, the amino acid normally found following the deletion site is still numbered as if the deletion did not occur, unless noted otherwise.

As is noted herein, any amino acid modification outlined herein or in the incorporated references can be combined with any other modification; the examples herein are not meant to be limiting. Thus, for example, it may be desirable to combine one or more deletions with one or more insertions and one or more subsititutions; one or more deletions with one or more insertions; one or more deletions with one or more substitutions; one or more substitutions with one or more insertions, etc.

By "glycoform modification" or "modified glycoform" or "engineered glycoform" as used herein is meant a carbohydrate composition that is covalently attached to a protein, for example an antibody, wherein said carbohydrate composition differs chemically from that of a parent protein. Modified glycoform typically refers to the different carbohydrate or oligosaccharide; thus for example an Fc variant may comprise a modified glycoform. Alternatively, modified glycoform may refer to the Fc variant that comprises the different carbohydrate or oligosaccharide. In particular, alterations in fucosylation are considered "engineered glycoforms", as is more fully described below.

By "parent polypeptide", "parent protein", "precursor polypeptide", or "precursor protein" as used herein is meant an unmodified polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent Fc polypeptide" as used herein is meant an Fc polypeptide that is modified to generate a variant, and by "parent antibody" as used herein is meant an antibody that is modified to generate a variant antibody. In some embodiments, the "parent" is a wild-type protein.

By "position" as used herein is meant a location in the sequence of a protein. Positions may be numbered sequentially, or according to an established format, for example the EU index as in Kabat. For example, position 297 is a position in the human antibody IgG1.

By "polypeptide" or "protein" as used herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "variant polypeptide", "polypeptide variant", or "variant" as used herein is meant a polypeptide sequence that differs from that of a parent polypeptide sequence by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "Fc variant" or "variant Fc" as used herein is meant an Fc sequence that differs from that of a parent Fc sequence by virtue of at least one amino acid modification. An Fc variant may only encompass an Fc region, or may exist in the context of an antibody, Fc fusion, isolated Fc, Fc fragment, or other polypeptide that is substantially encoded by Fc. Fc variant may refer to the Fc polypeptide itself, compositions comprising the Fc variant polypeptide, or the amino acid sequence that encodes it. By "Fc polypeptide variant" or "variant Fc polypeptide" as used herein is meant an Fc polypeptide that differs from a parent Fc polypeptide by virtue of at least one amino acid modification. By "protein variant" or "variant protein" as used herein is meant a protein that differs from a parent protein by virtue of at least one amino acid modification. By "antibody variant" or "variant antibody" as used herein is meant an antibody that differs from a parent antibody by virtue of at least one amino acid modification. By "IgG variant" or "variant IgG" as used herein is meant an antibody that differs from a parent IgG by virtue of at least one amino acid modification. By "immunoglobulin variant" or "variant immunoglobulin" as used herein is meant an immunoglobulin sequence that differs from that of a parent immunoglobulin sequence by virtue of at least one amino acid modification.

By "wild type" or "WT" herein is meant an amino acid sequence or a nucleotide sequence that is found in nature, including allelic variations. A WT protein, polypeptide, antibody, immunoglobulin, IgG, etc. has an amino acid sequence or a nucleotide sequence that has not been intentionally modified.

Antibodies

Antibodies are immunological proteins that bind a specific antigen. In most mammals, including humans and mice, antibodies are constructed from paired heavy and light polypeptide chains. The light and heavy chain variable regions show significant sequence diversity between antibodies, and are responsible for binding the target antigen. Each chain is made up of individual immunoglobulin (Ig) domains, and thus the generic term immunoglobulin is used for such proteins.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. IgA has several subclasses, including but not limited to IgA1 and IgA2. Thus, "isotype" as used herein is meant any of the classes and subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

Each of the light and heavy chains are made up of two distinct regions, referred to as the variable and constant regions. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order VL-CL, referring to the light chain variable domain and the light chain constant domain respectively. The constant regions show less sequence diversity, and are responsible for binding a number of natural proteins to elicit important biochemical events. The distinguishing features between these antibody classes are their constant regions, although subtler differences may exist in the variable region.

The variable region of an antibody contains the antigen binding determinants of the molecule, and thus determines the specificity of an antibody for its target antigen. The variable region is so named because it is the most distinct in sequence from other antibodies within the same class. The amino-terminal portion of each chain includes a variable region of about 100 to 110 or more amino acids primarily responsible for antigen recognition. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, Biophys Chem 68:9-16; Morea et al., 2000, Methods 20:267-279, hereby entirely incorporated by reference, and the conserved features of antibodies are disclosed, for example, in Maynard et al., 2000, Annu Rev Biomed Eng 2:339-376, hereby entirely incorporated by reference.

The carboxy-terminal portion of each chain defines a constant region primarily responsible for effector function. In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge region. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another important region of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230 to 236.

Of particular interest in the present invention are the Fc regions. By "Fc" or "Fc region", as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the lower hinge region between Cgamma1 (Cγ1) and Cgamma2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Fc may refer to this region in isolation, or this region in the context of an Fc polypeptide, as described below. By "Fc polypeptide" as used herein is meant a polypeptide that comprises all or part of an Fc region. Fc polypeptides include antibodies, Fc fusions, isolated Fcs, and Fc fragments.

The Fc region of an antibody interacts with a number of Fc receptors and ligands, imparting an array of important functional capabilities referred to as effector functions. For IgG the Fc region, Fc comprises Ig domains Cγ2 and Cγ3 and the N-terminal hinge leading into Cγ2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290, both hereby entirely incorporated by reference). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65, hereby entirely incorporated by reference). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γγ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290, both hereby entirely incorporated by reference). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP).

The different IgG subclasses have different affinities for the FcγRs, with IgG1 and IgG3 typically binding substantially better to the receptors than IgG2 and IgG4 (Jefferis et al., 2002, Immunol Lett 82:57-65, hereby entirely incorporated by reference). The FcγRs bind the IgG Fc region with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. Despite these differences in affinities and activities, all FcγRs bind the same region on Fc, at the N-terminal end of the Cγ2 domain and the preceding hinge. This interaction is well characterized structurally (Sondermann et al., 2001, J Mol Biol 309:737-749, hereby entirely incorporated by reference), and several structures of the human Fc bound to the extracellular domain of human FcγRIIIb have been solved (pdb accession code 1E4K) (Sondermann et al., 2000, Nature 406:267-273, hereby entirely incorporated by reference) (pdb accession codes 1IIS and 1IIX) (Radaev et al., 2001, J Biol Chem 276:16469-16477, hereby entirely incorporated by reference).

An overlapping but separate site on Fc serves as the interface for the complement protein C1q. In the same way that Fc/FcγR binding mediates ADCC, Fc/C1q binding mediates complement dependent cytotoxicity (CDC). A site on Fc between the Cγ2 and Cγ3 domains mediates interaction with the neonatal receptor FcRn, the binding of which recycles endocytosed antibody from the endosome back to the bloodstream (Raghavan et al., 1996, Annu Rev Cell Dev Biol 12:181-220; Ghetie et al., 2000, Annu Rev Immunol 18:739-766, both hereby entirely incorporated by reference). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. The fidelity of these regions, the complement and FcRn/protein A binding regions are important for both the clinical properties of antibodies and their development.

A key feature of the Fc region is the conserved N-linked glycosylation that occurs at N297. This carbohydrate, or oligosaccharide as it is sometimes referred, plays a critical structural and functional role for the antibody, and is one of the principle reasons that antibodies must be produced using mammalian expression systems. Efficient Fc binding to FcγR and C1q requires this modification, and alterations in the composition of the N297 carbohydrate or its elimination affect binding to these proteins (Umana et al., 1999, Nat Biotechnol 17:176-180; Davies et al., 2001, Biotechnol Bioeng 74:288-294; Mimura et al., 2001, J Biol Chem 276:45539-45547; Radaev et al., 2001, J Biol Chem 276:16478-16483; Shields et al., 2001, J Biol Chem 276:6591-6604; Shields et al., 2002, J Biol Chem 277:26733-26740; Simmons et al., 2002, J Immunol Methods 263:133-147, all hereby entirely incorporated by reference).

Variants of the Invention

In general, as outlined above and unless noted otherwise, Fc variants include amino acid modifications in the hinge region and/or the Cγ2 and Cγ3 regions.

An Fc variant comprises one or more amino acid modifications relative to a parent Fc polypeptide, wherein the amino acid modification(s) optionally provide one or more optimized properties, although in some cases, the variants exhibit substantially identical biological properties. It should be recognized that "optimized" may include increases and/or decreases in biological activity. That is, as is outlined herein, it may be desirable in some cases to substantially ablate binding to one or more FcγRs, even an activating receptor such as FcγIIIa.

An Fc variant of the present invention differs in amino acid sequence from its parent IgG by virtue of at least one amino acid modification. Thus Fc variants of the present invention have at least one amino acid modification compared to the parent. Alternatively, the Fc variants of the present invention may have more than one amino acid modification as compared to the parent, for example from about one to fifty amino acid modifications, preferably from about one to ten amino acid modifications, and most preferably from about one to about five amino acid modifications compared to the parent. Thus the sequences of the Fc variants and those of the parent Fc polypeptide are substantially homologous or identical. For example, the variant Fc variant sequences herein will possess about 80% homology (including identity) with the parent Fc variant sequence, preferably at least about 90% homology, and most preferably at least about 95, 96, 97, 98 and 99% identity. Modifications of the invention include amino acid modifications, including insertions, deletions, and substitutions. Modifications of the invention also include glycoform modifications. Modifications may be made genetically using molecular biology, or may be made enzymatically or chemically.

The Fc variants of the present invention are defined according to the amino acid modifications that compose them. Thus, for example, L328R is an Fc variant with the substitution L328R relative to the parent Fc polypeptide. Likewise, ^236R/L328R defines an Fc variant with the insertion ^236R and the substitution L328R relative to the parent Fc polypeptide. The identity of the WT amino acid may be unspecified, in which case the aforementioned variant is referred to as ^236R/328R. It is noted that the order in which modifications are provided is arbitrary, that is to say that, for example, ^236R/L328R is the same Fc variant as L328R/^236R, and so on. For all positions discussed in the present invention, numbering is according to the EU index or EU numbering scheme (Kabat et al., 1991, Sequences of Proteins of Immunological Interest, 5th Ed., United States Public Health Service, National Institutes of Health, Bethesda, hereby entirely incorporated by reference). The EU index or EU index as in Kabat or EU numbering scheme refers to the numbering of the EU antibody (Edelman et al., 1969, Proc Natl Acad Sci USA 63:78-85, hereby entirely incorporated by reference).

In one embodiment, one or more amino acid insertions are made. Amino acid insertions can be made within the hinge region, including at positions 233, 234, 235, 236 and 237. Exemplary insertions include, but are not limited to, ^233L, ^233EL, ^234L, ^235G, ^235A, ^235S, ^235T, ^235N, ^235D, ^235V, ^235L, ^235R, ^237R, ^237RR, ^297G, ^297D, ^297A, ^297S, ^326G, ^326T, ^326D and ^326E. Particular combinations of insertions and other modifications are also outlined in the figures. All of these may be done in any IgG molecule, particularly in IgG1 and IgG2. In some embodiments, insertions of glycine after position 235 are not preferred (^235G), except in combinations with other amino acid modifications.

In one embodiment, one or more amino acid deletions are made. Amino acid insertions can be made within the hinge region, including at positions 233, 234, 235, 236 and 237. Particular combinations of deletions and other modifications are also outlined in the figures. All of these may be done in any IgG molecule, particularly in IgG1 and IgG2. In some embodiments, deletions at position 236 are not preferred (236#), except in combinations with other amino acid modifications.

In one embodiment, one or more amino acid substitutions are made. Amino acid substitutions can be made at positions 221, 222, 224, 227, 228, 230, 231, 223, 233, 234, 235, 236, 237, 238, 239, 240, 241, 243, 244, 245, 246, 247, 249, 250, 258, 262, 263, 264, 265, 266, 267, 268, 269, 270, 271, 272, 273, 274, 275, 276, 278, 280, 281, 283, 285, 286, 288, 290, 291, 293, 294, 295, 296, 297, 298, 299, 300, 302, 313, 317, 318, 320, 322, 323, 324, 325, 326, 327, 328, 329, 330, 331, 332, 333, 334, 335 336 and 428, again, as any possible combination of substitution(s), insertion(s) and deletion(s). These amino acid substitutions include, but are not limited to, D221K, D221Y, K222E, K222Y, T223E, T223K, H224E, H224Y, T225E, T225K, T225W, P227E, P227G, P227K, P227Y, P228E, P228G, P228K, P228Y, P230A, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234K, L234M, L234N, L234P, L234Q, L234R, L234S, L234T, L234V, L234W, L234Y, L235A, L235D, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236J, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P238Y, S239D, S239E, S239F, S239G, S239H, S239I, S239K, S239L, S239M, S239N, S239P, S239Q, S239R, S239T, S239V, S239W, S239Y, V240A, V240I, V240M, V240T, F241D, F241E, F241L, F241R, F241S, F241W, F241Y, F243E, F243H, F243L, F243Q, F243R, F243W, F243Y, P244H, P245A, K246D, K246E, K246H, K246Y, P247G, P247V, D249H, D249Q, D249Y, R255E, R255Y, E258H, E258S, E258Y, T260D, T260E, T260H, T260Y, V262A, V262E, V262F, V262I, V262T, V263A, V263I, V263M, V263T, V264A, V264D, V264E, V264F, V264G, V264H, V264I, V264K, V264L, V264M, V264N, V264P, V264Q, V264R, V264S, V264T, V264W, V264Y, D265F, D265G, D265H, D265I, D265K, D265L, D265M, D265N, D265P, D265Q, D265R, D265S, D265T, D265V, D265W, D265Y, V266A, V266I, V266M, V266T, S267D, S267E, S267F, S267H, S267I, S267K, S267L, S267M, S267N, S267P, S267Q, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, D280G, D280K, D280L, D280P, D280W, G281D, G281E, G281K, G281N, G281P, G281Q, G281Y, V282E, V282G, V282K, V282P, V282Y, E283G, E283H, E283K, E283L, E283P, E283R, E283Y, V284D, V284E, V284L, V284N, V284Q, V284T, V284Y, H285D, H285E, H285K, H285Q, H285W, H285Y, N286D, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296H, Y296I, Y296K, Y296L, Y296M, Y296N, Y296Q, Y296R, Y296S, Y296T, Y296V, N297D, N297E, N297F, N297G, N297H, N297I, N297K, N297L, N297M, N297P, N297Q, N297R, N297S, N297T, N297V, N297W, N297Y, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328E, L328F, L328G, L328H, L328I, L328K, L328M, L328N, L328P, L328Q, L328R, L328S, L328T, L328V, L328W, L328Y, P329D, P329E, P329F, P329G, P329H, P329I, P329K, P329L, P329M, P329N, P329Q, P329R, P329S, P329T, P329V, P329Y, A330F, A330G, A330H, A330I, A330L, A330M, A330N, A330P, A330R, A330S, A330T, A330V, A330W, A330Y, P331D, P331F, P331H, P331I, P331L, P331M, P331Q, P331R, P331T, P331V, P331W, P331Y, I332A, I332D, I332E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334L, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, D221K, D221Y, K222E, K222Y, T223E, T223K, H224E, H224Y, T225E, T225K, T225W, P227E, P227G, P227K, P227Y, P228E, P228G, P228K, P228Y, P230A, P230A/E233D, P230A/E233D/I332E, P230E, P230G, P230Y, A231E, A231G, A231K, A231P, A231Y, P232E, P232G, P232K, P232Y, E233A, E233D, E233F, E233G, E233H, E233I, E233K, E233L, E233M, E233N, E233Q, E233R, E233S, E233T, E233V, E233W, E233Y, L234A, L234D, L234E, L234F, L234G, L234H, L234I, L234I/L235D, L234K, L234M, L234N, L234P, L234Q, L234R, L234S, L234T, L234V, L234W, L235A, L235D, L235D/S239D/A330Y/I332E, L235D/S239D/N297D/I332E, L235E, L235F, L235G, L235H, L235I, L235K, L235M, L235N, L235P, L235Q, L235R, L235S, L235T, L235V, L235W, L235Y, G236A, G236D, G236E, G236F, G236H, G236I, G236K, G236L, G236M, G236N, G236P, G236Q, G236R, G236S, G236T, G236V, G236W, G236Y, G237D, G237E, G237F, G237H, G237I, G237K, G237L, G237M, G237N, G237P, G237Q, G237R, G237S, G237T, G237V, G237W, G237Y, P238D, P238E, P238F, P238G, P238H, P238I, P238K, P238L, P238M, P238N, P238Q, P238R, P238S, P238T, P238V, P238W, P238Y, S239D, S239D/A330L/I332E, S239D/A330Y/I332E/L234I, S239D/A330Y/I332E/V266I, S239D/D265F/N297D/I332E, S239D/D265H/N297D/I332E, S239D/D265I/N297D/I332E, S239D/D265L/N297D/I332E, S239D/D265T/N297D/I332E, S239D/D265Y/N297D/I332E, S239D/E272I/A330L/I332E, S239D/E272I/I332E, S239D/E272K/A330L/I332E, S239D/E272K/I332E, S239D/E272S/A330L/I332E, S239D/E272S/I332E, S239D/E272Y/A330L/I332E, S239D/E272Y/I332E, S239D/F241S/F243H/V262T/V264T/N297D/A330Y/I332E, S239D/H268D, S239D/H268E, S239D/I332D, S239D/I332E, S239D/I332E/A327D, S239D/I332E/A330I, S239D/I332E/A330Y, S239D/I332E/E272H, S239D/I332E/E272R, S239D/I332E/E283H, S239D/I332E/E283L, S239D/I332E/G236A, S239D/I332E/G236S, S239D/I332E/H268D, S239D/I332E/H268E, S239D/I332E/K246H, S239D/I332E/R255Y, S239D/I332E/S267E, S239D/I332E/V264I, S239D/I332E/V264I/A330L, S239D/I332E/V264I/S298A, S239D/I332E/V284D, S239D/I332E/V284E, S239D/I332E/V284E, S239D/I332N, S239D/I332Q, S239D/K274E/A330L/I332E, S239D/K274E/I332E, S239D/K326E/A330L/I332E, S239D/K326E/A330Y/I332E, S239D/K326E/I332E, S239D/K326T/A330Y/I332E, S239D/K326T/I332E, S239D/N297D/A330Y/I332E, S239D/N297D/I332E, S239D/N297D/K326E/I332E, S239D/S267E/A330L/I332E, S239D/S267E/I332E, S239D/S298A/K326E/I332E, S239D/S298A/K326T/I332E, S239D/V240I/A330Y/I332E, S239D/V264T/A330Y/I332E, S239D/Y278T/A330L/I332E, S239D/Y278T/I332E, S239E, S239E/D265G, S239E/D265N, S239E/D265Q, S239E/I332D, S239E/I332E, S239E/I332N, S239E/I332Q, S239E/N297D/I332E, S239E/V264I/A330Y/I332E, S239E/V264I/I332E, S239E/V264I/S298A/A330Y/I332E, S239F, S239G, S239H, S239I, S239K, S239L, S239M, S239N, S239N/I332D, S239N/I332E, S239N/I332E/A330L, S239N/I332E/A330Y, S239N/I332N, S239N/I332Q, S239P, S239Q, S239Q/I332D, S239Q/I332E, S239Q/I332N, S239Q/I332Q, S239Q/V264I/I332E, S239R, S239T, S239V, S239W, S239Y, V240A, V240I, V240I/V266I, V240M, V240T, F241D, F241E, F241E/F243Q/V262T/V264E/I332E, F241E/F243Q/V262T/V264E, F241E/F243R/V262E/V264R/I332E, F241E/F243R/V262E/V264R, F241E/F243Y/V262T/V264R/I332E, F241E/F243Y/C262T/V264R, F241L, F241L/F243L/V262I/V264I, F241L/V262I, F241R/F243Q/V262T/V264R/I332E, F241R/F243Q/V262T/V264R, F241W, F241W/F243W, F241W/F243W/V262A/V264A, F241Y, F241Y/F243Y/V262T/V264T/N297D/I332E, F241Y/F243Y/V262T/V264T, F243E, F243L, F243L/V262I/N264W, F243L/V264I, F243W, P244H, P244H/P245A/P247V, P245A, K246D, K246E, K246H, K246Y, P247G, P247V, D249H, D249Q, D249Y, R255E, R255Y, E258H, E258S, E258Y, T260D, T260E, T260H, T260Y, V262E, V262F, V263A, V263I, V263M, V263T, V264A, V264D, V264E, V264E/N297D/I332E, V264F, V264G, V264H, V264I, V264I/A330L/I332E, V264I/A330Y/I332E, V264I/I332E, V264K, V264L, V264M, V264N, V264P, V264Q, V264R, V264S, V264T, V264W, V264Y, D265F, D265F/N297E/I332E, D265G, D265H, D265I, D265K, D265L, D265M, D265N, D265P, D265Q, D265R, D265S, D265T, D265V, D265W, D265Y, D265Y/N297D/I332E, D265Y/N297D/T299L/I332E, V266A, V266I, V266M, V266T, S267D, S267E, S267E, S267E/A327D, S267E/P331D, S267E/S324I, S267E/V282G, S267F, S267H, S267I, S267K, S267L, S267L/A327S, S267M, S267N, S267P, S267Q, S267Q/A327S, S267R, S267T, S267V, S267W, S267Y, H268D, H268E, H268F, H268G, H268I, H268K, H268L, H268M, H268P, H268Q, H268R, H268T, H268V, H268W, E269F, E269G, E269H, E269I, E269K, E269L, E269M, E269N, E269P, E269R, E269S, E269T, E269V, E269W, E269Y, D270F, D270G, D270H, D270I, D270L, D270M, D270P, D270Q, D270R, D270S, D270T, D270W, D270Y, P271A, P271D, P271E, P271F, P271G, P271H, P271I, P271K, P271L, P271M, P271N, P271Q, P271R, P271S, P271T, P271V, P271W, P271Y, E272D, E272F, E272G, E272H, E272I, E272K, E272L, E272M, E272P, E272R, E272S, E272T, E272V, E272W, E272Y, V273I, K274D, K274E, K274F, K274G, K274H, K274I, K274L, K274M, K274N, K274P, K274R, K274T, K274V, K274W, K274Y, F275L, F275W, N276D, N276E, N276F, N276G, N276H, N276I, N276L, N276M, N276P, N276R, N276S, N276T, N276V, N276W, N276Y, Y278D, Y278E, Y278G, Y278H, Y278I, Y278K, Y278L, Y278M, Y278N, Y278P, Y278Q, Y278R, Y278S, Y278T, Y278V, Y278W, Y278W, Y278W/E283R/V302I, Y278W/V302I, D280G, D280K, D280L, D280P, D280W, G281D, G281D/V282G, G281E, G281K, G281N, G281P, G281Q, G281Y, V282E, V282G, V282G/P331D, V282K, V282P, V282Y, E283G, E283H, E283K, E283L, E283P, E283R, E283R/V302I/Y278W/E283R, E283Y, V284D, V284E, V284L, V284N, V284Q, V284T, V284Y, H285D, H285E, H285K, H285Q, H285W, H285Y, N286E, N286G, N286P, N286Y, K288D, K288E, K288Y, K290D, K290H, K290L, K290N, K290W, P291D, P291E, P291G, P291H, P291I, P291Q, P291T, R292D, R292E, R292T, R292Y, E293F, E293G, E293H, E293I, E293L, E293M, E293N, E293P, E293R, E293S, E293T, E293V, E293W, E293Y, E294F, E294G, E294H, E294I, E294K, E294L, E294M, E294P, E294R, E294S, E294T, E294V, E294W, E294Y, Q295D, Q295E, Q295F, Q295G, Q295H, Q295I, Q295M, Q295N, Q295P, Q295R, Q295S, Q295T, Q295V, Q295W, Q295Y, Y296A, Y296D, Y296E, Y296G, Y296I, Y296K, Y296L, Y296M, Y296N, Y296Q, Y296R, Y296S, Y296T, Y296V, N297D, N297D/I332E, N297D/I332E/A330Y, N297D/I332E/S239D/A330L, N297D/I332E/S239D/D265V, N297D/I332E/S298A/A330Y, N297D/I332E/T299E, N297D/I332E/T299F, N297D/I332E/T299H, N297D/I332E/T299I, N297D/I332E/T299L, N297D/I332E/T299V, N297D/I332E/V296D, N297D/I332E/Y296E, N297D/I332E/Y296H, N297D/I332E/Y296N, N297D/I332E/Y296Q, N297D/I332E/Y296T, N297E/I332E, N297F, N297G, N297H, N297I, N297K, N297L, N297M, N297P, N297Q, N297R, N297S, N297S/I332E, N297T, N297V, N297W, N297Y, S298A/I332E, S298A/K326E, S298A/K326E/K334L, S298A/K334L, S298D, S298E, S298F, S298H, S298I, S298K, S298M, S298N, S298Q, S298R, S298T, S298W, S298Y, T299A, T299D, T299E, T299F, T299G, T299H, T299I, T299K, T299L, T299M, T299N, T299P, T299Q, T299R, T299S, T299V, T299W, T299Y, Y300A, Y300D, Y300E, Y300G, Y300H, Y300K, Y300M, Y300N, Y300P, Y300Q, Y300R, Y300S, Y300T, Y300V, Y300W, R301D, R301E, R301H, R301Y, V302I, V303D, V303E, V303Y, S304D, S304H, S304L, S304N, S304T, V305E, V305T, V305Y, W313F, K317E, K317Q, E318H, E318L, E318Q, E318R, E318Y, K320D, K320F, K320G, K320H, K320I, K320L, K320N, K320P, K320S, K320T, K320V, K320W, K320Y, K322D, K322F, K322G, K322H, K322I, K322P, K322S, K322T, K322V, K322W, K322Y, V323I, S324D, S324F, S324G, S324H, S324I, S324I/A327D, S324L, S324M, S324P, S324R, S324T, S324V, S324W, S324Y, N325A, N325D, N325E, N325F, N325G, N325H, N325I, N325K, N325L, N325M, N325P, N325Q, N325R, N325S, N325T, N325V, N325W, N325Y, K326I, K326L, K326P, K326T, A327D, A327E, A327F, A327H, A327I, A327K, A327L, A327M, A327N, A327P, A327R, A327S, A327T, A327V, A327W, A327Y, L328A, L328D, L328D/I332E, L328E, L328E/I332E, L328F, L328G, L328H, L328H/I332E, L328I, L328I/I332E, L328I/I332E, L328K, L328M, L328M/I332E, L328N, L328N/I332E, L328P, L328Q, L328Q/I332E, L328Q/I332E, L328R, L328S, L328T, L328T/I332E, L328V, L328V/I332E, L328W, L328Y, P329D, P329E, P329F, P329G, P329H, P329I, P329K, P329L, P329M, P329N, P329Q, P329R, P329S, P329T, P329V, P329W, P329Y, A330E, A330F, A330G, A330H, A330I, A330L, A330L/I332E, A330M, A330N, A330P, A330R, A330S, A330T, A330V, A330W, A330Y, A330Y/I332E, P331D, P331F, P331H, P331I, P331L, P331M, P331Q, P331R, P331T, P331V, P331W, P331Y, I332A, I332D, I332E, I332E/G281D, I332E/H268D, I332E/H268E, I332E/S239D/S298A, I332E/S239N/S298A, I332E/V264I/S298A, I332E/V284E, I332F, I332H, I332K, I332L, I332M, I332N, I332P, I332Q, I332R, I332S, I332T, I332V, I332W, I332Y, E333F, E333H, E333I, E333L, E333M, E333P, E333T, E333Y, K334F, K334I, K334P, K334T, T335D, T335F, T335G, T335H, T335I, T335L, T335M, T335N, T335P, T335R, T335S, T335V, T335W, T335Y, I336E, I336K, I336Y, S337E, S337H, and S337N, wherein the numbering of the residues in the Fc region is that of the EU index as in Kabat, as is true throughout. Particular combinations of insertion(s), deletion(s) and other modifications are also outlined in the figures. All of these may be done in any IgG molecule, particularly in IgG1 and IgG2.

In some embodiments, combinations of modifications that find use in the present invention are found in FIGS. 4 and 6-17, and additionally include ^236R/L328R (particularly in IgG1) and ^236A/I332E (particularly in IgG2). Similarly, amino modifications at 332 and/or 239 can be coupled with insertion(s) and/or deletion(s).

Functionally, variants that result in increased binding to activating FcγRs as compared to the change in binding affinity to inhibitory FcγRs find particular use in some embodiments.

The Fc variants of the present invention may be substantially encoded by immunoglobulin genes belonging to any of the antibody classes. In certain embodiments, the Fc variants of the present invention find use in antibodies or Fc fusions that comprise sequences belonging to the IgG class of antibodies, including IgG1, IgG2, IgG3, or IgG4. FIG. 1 provides an alignment of these human IgG sequences. In an alternate embodiment the Fc variants of the present invention find use in antibodies or Fc fusions that comprise sequences belonging to the IgA (including subclasses IgA1 and IgA2), IgD, IgE, IgG, or IgM classes of antibodies. The Fc variants of the present invention may comprise more than one protein chain. That is, the present invention may find use in an antibody or Fc fusion that is a monomer or an oligomer, including a homo- or hetero-oligomer.

In certain embodiments, the Fc variants of the invention are based on human IgG sequences, and thus human IgG sequences are used as the "base" sequences against which other sequences are compared, including but not limited to sequences from other organisms, for example rodent and primate sequences. Fc variants may also comprise sequences from other immunoglobulin classes such as IgA, IgE, IgGD, IgGM, and the like. It is contemplated that, although the Fc variants of the present invention are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first Fc variant are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second IgG that is at the level of tertiary structure for IgGs whose structures have been determined. In this case, equivalent residues are defined as those for which the atomic coordinates of two or more of the main chain atoms of a particular amino acid residue of the parent or precursor (N on N, CA on CA, C on C and O on O) are within about 0.13 nm and preferably about 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent IgG in which the IgGs are made, what is meant to be conveyed is that the Fc variants discovered by the present invention may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent Fc variant does not affect the ability to transfer the Fc variants of the present invention to other parent IgGs.

Fc variants of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a certain embodiments, the Fc variants of the present invention are substantially human.

As is well known in the art, immunoglobulin polymorphisms exist in the human population. Gm polymorphism is determined by the IGHG1, IGHG2 and IGHG3 genes which have alleles encoding allotypic antigenic determinants referred to as G1 m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem Immunol. 65:88-110; Gorman & Clark, 1990, Semin Immunol 2(6):457-66, both hereby entirely incorporated by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; Loghem E van, 1986, Allotypic markers, Monogr Allergy 19: 40-51, all hereby entirely incorporated by reference). Additionally, other polymorphisms have been characterized (Kim et al., 2001, J. Mol. Evol. 54:1-9, hereby entirely incorporated by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both hereby entirely incorporated by reference). Allotypes that are inherited in fixed combinations are called Gm haplotypes. FIG. 2 shows common haplotypes of the gamma chain of human IgG1 (FIG. 2a) and IgG2 (FIG. 2b) showing the positions and the relevant amino acid substitutions. The Fc variants of the present invention may be substantially encoded by any allotype, isoallotype, or haplotype of any immunoglobulin gene.

The Fc variants of the invention can compose any Fc polypeptide, including but not limited to antibodies, isolated Fcs, Fc fragments, and Fc fusions. In one embodiment, the Fc polypeptide of the invention is a full length antibody, constituting the natural biological form of an antibody, including variable and constant regions. For the IgG isotype full length antibody is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3.

Fc polypeptides and antibodies of the invention can be a variety of structures, including, but not limited antibody fragments, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and fragments of each, respectively.

In one embodiment, the antibody is an antibody fragment. Of particular interest are antibodies that comprise Fc regions, Fc fusions, and the constant region of the heavy chain (CH1-hinge-CH2-CH3), again also including constant heavy region fusions.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment, which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site, (viii) bispecific single chain Fv dimers, and (ix) "diabodies" or "triabodies", multivalent or multispecific fragments constructed by gene fusion. The antibody fragments may be modified. For example, the molecules may be stabilized by the incorporation of disulphide bridges linking the VH and VL domains. Examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference.

In one embodiment, the antibody of the invention is a multispecific antibody, and notably a bispecific antibody, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

Fc Fusions, Antibody Fusions, and Antibody Conjugates

In addition to antibodies, an antibody-like protein that is finding an expanding role in research and therapy is the Fc fusion (Chamow et al., 1996, Trends Biotechnol 14:52-60; Ashkenazi et al., 1997, Curr Opin Immunol 9:195-200, both incorporated entirely by reference). "Fc fusion" is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion is a protein wherein one or more polypeptides is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present invention extends also to Fc fusions.

Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

In one embodiment, the Fc variants of the invention are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588, incorporated entirely by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the Fc variant. Thus, for example, the conjugation of a toxin to an Fc variant targets the delivery of said toxin to cells expressing the target antigen. As will be appreciated by one skilled in the art, in reality the concepts and definitions of fusion and conjugate are overlapping. The designation of a fusion or conjugate is not meant to constrain it to any particular embodiment of the present invention. Rather, these terms are used loosely to convey the broad concept that any Fc variant of the present invention may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331, incorporated enirely by reference.

In one embodiment, the Fc variants of the present invention are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, incorporated entirely by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the Fc variants of the present invention are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14:49-71, incorporated entirely by reference. Small molecule toxins include but are not limited to calicheamicin, maytansine (U.S. Pat. No. 5,208,020, incorporated entirely by reference), trichothene, and CC1065. In one embodiment of the invention, the Fc variant is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al., 1992, Cancer Research 52: 127-131, incorporated entirely by reference) to generate a maytansinoid-antibody conjugate. Another conjugate of interest comprises an Fc variant conjugated to one or more calicheamicin molecules. The calicheamicin family of antibiotics are capable of producing double-stranded DNA breaks at sub-picomolar concentrations. Structural analogues of calicheamicin that may be used include but are not limited to $\gamma_1^1$, $\alpha_2^1$, $\alpha_3$, N-acetyl-$\gamma_1^1$, PSAG, and $\Theta_1^1$, (Hinman et al., 1993, Cancer Research 53:3336-3342; Lode et al., 1998, Cancer Research 58:2925-2928) (U.S. Pat. Nos. 5,714,586; 5,712,374; 5,264,586; 5,773,001, all incorporated enirely by reference). Dolastatin 10 analogs such as auristatin E (AE) and monomethylauristatin E (MMAE) may find use as conjugates for the Fc variants of the present invention (Doronina et al., 2003, Nat Biotechnol 21(7):778-84; Francisco et al., 2003 Blood 102(4):1458-65, both incorporated entirely by reference). Useful enyzmatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, PCT WO 93/21232, incorporated entirely by reference. The present invention further contemplates a conjugate between an Fc variant of the present invention and a compound with nucleolytic activity, for example a ribonuclease or DNA endonuclease such as a deoxyribonuclease (Dnase).

In an alternate embodiment, an Fc variant of the present invention may be fused, conjugated, or operably linked to a radioisotope to form a radioconjugate. A variety of radioactive isotopes are available for the production of radioconjugate antibodies. Examples include, but are not limited to, At211, I131, I125, Y90, Re186, Re188, Sm153, Bi212, P32, and radioactive isotopes of Lu. See for example, reference.

In yet another embodiment, an Fc variant of the present invention may be conjugated to a "receptor" (such streptavidin) for utilization in tumor pretargeting wherein the Fc variant-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the Fc variant is conjugated or operably linked to an enzyme in order to employ Antibody Dependent Enzyme Mediated Prodrug Therapy (ADEPT). ADEPT may be used by conjugating or operably linking the Fc variant to a prodrug-activating enzyme that converts a prodrug (e.g. a peptidyl chemotherapeutic agent, see PCT WO 81/01145, incorporated entirely by reference) to an active anti-cancer drug. See, for example, PCT WO 88/07378 and U.S. Pat. No. 4,975,278, both incorporated entirely by reference. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuramimidase useful for converting glycosylated prodrugs into free drugs; beta-lactamase useful for converting drugs derivatized with .alpha.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, *Nature* 328: 457-458, incorporated entirely by reference). Fc variant-abzyme conjugates can be prepared for delivery of the abzyme to a tumor cell population. A variety of additional conjugates are contemplated for the Fc variants of the present invention. A variety of chemotherapeutic agents, anti-angiogenic agents, tyrosine kinase inhibitors, and other therapeutic agents are described below, which may find use as Fc variant conjugates.

Also contemplated as fusion and conjugate partners are Fc polypeptides. Thus an Fc variant may be a multimeric Fc polypeptide, comprising two or more Fc regions. The advantage of such a molecule is that it provides multiple binding sites for Fc receptors with a single protein molecule. In one embodiment, Fc regions may be linked using a chemical engineering approach. For example, Fab's and Fc's may be linked by thioether bonds originating at cysteine residues in the hinges, generating molecules such as FabFc$_2$. Fc regions may be linked using disulfide engineering and/or chemical cross-linking. In a preferred embodiment, Fc regions may be linked genetically. In a preferred embodiment, Fc regions in an Fc variant are linked genetically to generated tandemly linked Fc regions as described in U.S. Ser. No. 11/022,289, filed Dec. 21, 2004, entitled "Fc polypeptides with novel Fc ligand binding sites," incorporated entirely by reference. Tandemly linked Fc polypeptides may comprise two or more Fc regions, preferably one to three, most preferably two Fc regions. It may be advantageous to explore a number of engineering constructs in order to obtain homo- or heterotandemly linked Fc variants with the most favorable structural and functional properties. Tandemly linked Fc variants may be homo- tandemly linked Fc variants, that is an Fc variant of one isotype is fused genetically to another Fc variant of the same isotype. It is anticipated that because there are multiple Fc R, C1q, and/or FcRn binding sites on tandemly linked Fc polypeptides, effector functions and/or pharmacokinetics may be enhanced. In an alternate embodiment, Fc variants from different isotypes may be tandemly linked, referred to as hetero- tandemly linked Fc variants. For example, because of the capacity to target FcγR and FcαRI receptors, an Fc variant that binds both FcγRs and FcαRI may provide a significant clinical improvement.

Fusion and conjugate partners may be linked to any region of an Fc variant of the present invention, including at the N- or C-termini, or at some residue in-between the termini. In a preferred embodiment, a fusion or conjugate partner is linked at the N- or C-terminus of the Fc variant, most preferably the N-terminus. A variety of linkers may find use in the present invention to covalently link Fc variants to a fusion or conjugate partner. By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. Linkers are known in the art; for example, homo- or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. Preferably, the linker is from about 1 to 30 amino acids in length, with linkers of 1 to 20 amino acids in length being most preferred. Useful linkers include glycine-serine polymers (including, for example, (GS)n, (GSGGS)n [SEQ ID NO. 16] (GGGGS)n [SEQ ID NO. 17] and (GGGS)n [SEQ ID NO. 18], where n is an integer of at least one), glycine-alanine polymers, alanine-serine polymers, and other flexible linkers, as will be appreciated by those in the art. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the Fc variants of the present invention to a fusion or conjugate partner, or to link the Fc variants of the present invention to a conjugate.

Nonhuman, Chimeric, Humanized, and Fully Human Antibodies

The variable region of an antibody, as is well known in the art, can compose sequences from a variety of species. In some embodiments, the antibody variable region can be from a nonhuman source, including but not limited to mice, rats, rabbits, camels, llamas, and monkeys. In some embodiments, the scaffold components can be a mixture from different species. As such, if the antibody of the invention may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse or other nonhuman species and the constant region(s) from a human.

"Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. "Backmutation" of selected acceptor framework residues to the corresponding donor residues is often required to regain affinity that is lost in the initial grafted construct (U.S. Pat. No. 5,693,762, incorporated entirely by reference. The humanized antibody optimally also will comprise at least a portion of an immunoglobulin constant region, typically that of a human immunoglobulin, and thus will typically comprise a human Fc region. Humanized antibodies can also be generated using mice with a genetically engineered immune system. Roque et al., 2004, Biotechnol. Prog. 20:639-654. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084. Structure-based methods may be employed for humanization and affinity maturation, for example as described in U.S. Ser. No. 10/153,159 and related applications, all incorporated enirely by reference. In certain variations, the immunogenicity of the antibody is reduced using a method described in U.S. Ser. No. 11/004,590, entitled "Methods of Generating Variant Proteins with Increased Host String Content and Compositions Thereof", filed on Dec. 3, 2004, incorporated entirely by reference.

In one embodiment, the antibody is a fully human antibody with at least one modification as outlined herein. "Fully human antibody" or "complete human antibody" refers to a human antibody having the gene sequence of an antibody derived from a human chromosome with the modifications outlined herein. Fully human antibodies may be obtained, for example, using transgenic mice (Bruggemann et al., 1997, Curr Opin Biotechnol 8:455-458) or human antibody libraries coupled with selection methods (Griffiths et al., 1998, Curr Opin Biotechnol 9:102-108).

Targets

The Fc variants of the present invention may be agonists, antagonists, neutralizing, inhibitory, or stimulatory. The Fc variant may find use in an antibody composition that is monoclonal or polyclonal. In a preferred embodiment, the Fc variants of the present invention are used to kill target cells that bear the target antigen, for example cancer cells. In an alternate embodiment, the Fc variants of the present invention are used to block, antagonize, or agonize the target antigen, for example for antagonizing a cytokine or cytokine receptor. In an alternately preferred embodiment, the Fc variants of the present invention are used to block, antagonize, or agonize the target antigen and kill the target cells that bear the target antigen.

Virtually any antigen may be targeted by the Fc variants of the present invention, including but not limited to proteins, subunits, domains, motifs, and/or epitopes belonging to the following list of targets: 17-IA, 4-1 BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCl, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-1 (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bpi, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Mud), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2DRS, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DcTRAIL R2TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors, etc.

Fc Receptor Binding Properties

The Fc variants of the present invention may be optimized for a variety of Fc receptor binding properties. An Fc variant that is engineered or predicted to display one or more optimized properties is herein referred to as an "optimized Fc variant". Properties that may be optimized include but are not limited to enhanced or reduced affinity for an FcγR. In a preferred embodiment, the Fc variants of the present invention are optimized to possess enhanced affinity for a human activating FcγR, preferably FcγRI, FcγRIIa, FcγRIIc, FcγRIIIa, and FcγRIIIb, most preferrably FcγRIIa and FcγRIIIa. In an alternately preferred embodiment, the Fc variants are optimized to possess reduced affinity for the human inhibitory receptor FcγRIIb. These preferred embodiments are anticipated to provide Fc polypeptides with enhanced therapeutic properties in humans, for example enhanced effector function and greater anti-cancer potency. In other embodiments, Fc variants of the present invention provide enhanced affinity for one or more FcγRs, yet reduced affinity for one or more other FcγRs. For example, an Fc variant of the present invention may have enhanced binding to FcγRI, FcγRIIa, and/or FcγRIIIa, yet reduced binding to FcγRIIb.

By "greater affinity" or "improved affinity" or "enhanced affinity" or "better affinity" than a parent Fc polypeptide, as used herein is meant that an Fc variant binds to an Fc receptor with a significantly higher equilibrium constant of association ($K_A$) or lower equilibrium constant of dissociation ($K_D$) than the parent Fc polypeptide when the amounts of variant and parent polypeptide in the binding assay are essentially the same. For example, the Fc variant with improved Fc receptor binding affinity may display from about 5 fold to about 1000 fold, e.g. from about 10 fold to about 500 fold improvement in Fc receptor binding affinity compared to the parent Fc polypeptide, where Fc receptor binding affinity is determined, for example, as disclosed in the Examples herein. Accordingly, by "reduced affinity" as compared to a parent Fc polypeptide as used herein is meant that an Fc variant binds an Fc receptor with significantly lower $K_A$ or higher $K_D$ than the parent Fc polypeptide.

In a preferred embodiment of the invention, the Fc variants provide selectively enhanced affinity to one or more human activating receptors relative to the inhibitory receptor FcγRIIb. Selectively enhanced affinity to an activating receptor relative to FcγRIIb means either that the Fc variant has improved affinity for the activating receptor as compared to the parent Fc polypeptide but has reduced affinity for FcγRIIb as compared to the parent Fc polypeptide, or it means that the Fc variant has improved affinity for both activating and inhibitory receptors as compared to the parent Fc polypeptide, however the improvement in affinity is greater for the activating receptor than it is for FcγRIIb. The purpose of grouping both of these Fc receptor properties together is that currently it is not known for cells that express both activating and inhibitory receptors whether activation/inhibition is determined by the absolute threshold of FcγRIIb engagement, or by the relative engagement by activating and inhibitory receptors. The preferred application of Fc variants with such Fc receptor affinity profiles is to impart antibodies, Fc fusions, or other Fc polypeptides with enhanced FcγR-mediated effector function and cellular activation, specifically for cells that express both activating and inhibitory receptors including but not limited to neutrophils, monocytes and macrophages, and dendritic cells.

In alternately preferred embodiments of the present invention, the Fc variants reduce or ablate binding to one or more FcγRs, reduce or ablate binding to one or more complement proteins, reduce or ablate one or more FcγR-mediated effector functions, and/or reduce or ablate one or more complement-mediated effector functions. In some embodiments, insertions and/or deletions can be used to ablate the activity, and then amino acid substitutions can be used to increase binding, in many cases to one or more selected FcγRs.

The presence of different polymorphic forms of FcγRs provides yet another parameter that impacts the therapeutic utility of the Fc variants of the present invention. Whereas the specificity and selectivity of a given Fc variant for the different classes of FcγRs signficantly affects the capacity of an Fc variant to target a given antigen for treatment of a given disease, the specificity or selectivity of an Fc variant for different polymorphic forms of these receptors may in part determine which research or pre-clinical experiments may be appropriate for testing, and ultimately which patient populations may or may not respond to treatment. Thus the specificity or selecitivty of Fc variants of the present invention to Fc receptor polymorphisms, including but not limited to FcγRIIa, FcγRIIIa, and the like, may be used to guide the selection of valid research and pre-clinical experiments, clinical trial design, patient selection, dosing dependence, and/or other aspects concerning clinical trials.

Fc variants of the invention may comprise modifications that modulate interaction with Fc receptors other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136).

Clearly an important parameter that determines the most beneficial selectivity of a given Fc variant to treat a given disease is the context of the Fc variant. Thus the Fc receptor selectivity or specifity of a given Fc variant will provide different properties depending on whether it composes an antibody, Fc fusion, or Fc variants with a coupled fusion or conjugate partner.

Preferably, the Fc receptor specificity of the Fc variant of the present invention will determine its therapeutic utility. The utility of a given Fc variant for therapeutic purposes will depend on the epitope or form of the target antigen and the disease or indication being treated. For some targets and indications, enhanced FcγR-mediated effector functions may be preferable. This may be particularly favorable for anti-cancer Fc variants. Thus Fc variants may be used that comprise Fc variants that provide enhanced affinity for activating FcγRs and/or reduced affinity for inhibitory FcγRs. For some targets and indications, it may be further beneficial to utilize Fc variants that provide differential selectivity for different activating FcγRs; for example, in some cases enhanced binding to FcγRIIa and FcγRIIIa may be desired, but not FcγRI, whereas in other cases, enhanced binding only to FcγRIIa may be preferred. For certain targets and indications, it may be preferable to utilize Fc variants that enhance both FcγR-mediated and complement-mediated effector functions, whereas for other cases it may be advantageous to utilize Fc variants that enhance either FcγR-mediated or complement-mediated effector functions. For some targets or cancer indications, it may be advantageous to reduce or ablate one or more effector functions, for example by knocking out binding to C1q, one or more FcγR's, FcRn, or one or more other Fc ligands. For other targets and indications, it may be preferable to utilize Fc variants that provide enhanced binding to the inhibitory FcγRIIb, yet WT level, reduced, or ablated binding to activating FcγRs. This may be particularly useful, for example, when the goal of an Fc variant is to inhibit inflammation or auto-immune disease, or modulate the immune system in some way.

In a preferred embodiment, the target of the Fc variants of the present invention is itself one or more Fc ligands. Fc polypeptides of the invention can be utilized to modulate the activity of the immune system, and in some cases to mimic the effects of IVIg therapy in a more controlled, specific, and efficient manner. IVIg is effectively a high dose of immunoglobulins delivered intravenously. In general, IVIg has been used to down-regulate autoimmune conditions. It has been hypothesized that the therapeutic mechanism of action of IVIg involves ligation of Fc receptors at high frequency (J. Bayry et al., 2003, Transfusion Clinique et Biologique 10: 165-169; Binstadt et al., 2003, J. Allergy Clin. Immunol, 697-704). Indeed animal models of (thrombocytopenia pur- pura (ITP) show that the isolated Fc are the active portion of IVIg (Samuelsson et al, 2001, Pediatric Research 50(5), 551).

For use in therapy, iimmunoglobulins are harvested from thousands of donors, with all of the concomitant problems associated with non-recombinant biotherapeutics collected from humans. An Fc variant of the present invention should serve all of the roles of IVIg while being manufactured as a recombinant protein rather than harvested from donors.

The immunomodulatory effects of IVIg may be dependent on productive interaction with one or more Fc ligands, including but not limited to FcγRs, complement proteins, and FcRn. In some embodiments, Fc variants of the invention with enhanced affinity for FcγRIIb can be used to promote anti-inflammatory activity (Samuelsson et al., 2001, Science 291: 484-486) and or to reduce autoimmunity (Hogarth, 2002, Current Opinion in Immunology, 14:798-802). In other embodiments, Fc polypeptides of the invention with enhanced affinity for one or more FcγRs can be utilized by themselves or in combination with additional modifications to reduce autoimmunity (Hogarth, 2002, Current Opinion in Immunology, 14:798-802). In alternative embodiments, Fc variants of the invention with enhanced affinity for FcγRIIIa but reduced capacity for intracellular signaling can be used to reduce immune system activation by competitively interfering with FcγRIIIa binding. The context of the Fc variant dramatically impacts the desired specificity. For example, Fc variants that provide enhanced binding to one or more activating FcγRs may provide optimal immunomodulatory effects in the context of an antibody, Fc fusion, isolated Fc, or Fc fragment by acting as an FcγR antagonist (van Mirre et al., 2004, J. Immunol. 173:332-339). However, fusion or conjugation of two or more Fc variants may provide different effects, and for such an Fc polypeptide it may be optimal to utilize Fc variants that provide enhanced affinity for an inhibitory receptor.

The Fc variants of the present invention may be used as immunomodulatory therapeutics. Binding to or blocking Fc receptors on immune system cells may be used to influence immune response in immunological conditions including but not limited to idiopathic thrombocytopenia purpura (ITP) and rheumatoid arthritis (RA) among others. By use of the affinity enhanced Fc variants of the present invention, the dosages required in typical IVIg applications may be reduced while obtaining a substantially similar therapeutic effect. The Fc variants may provide enhanced binding to an FcγR, including but not limited to FcγRIIa, FcγRIIb, FcγRIIIa, FcγRIIIb, and/or FcγRI. In particular, binding enhanements to FcγRIIb would increase expression or inhibitory activity, as needed, of that receptor and improve efficacy. Alternatively, blocking binding to activation receptors such as FcγRIIIb or FcγRI may improve efficacy. In addition, modulated affinity of the Fc variants for FcRn and/or also complement may also provide benefits.

In one embodiment, Fc variants that provide enhanced binding to the inhibitory receptor FcγRIIb provide an enhancement to the IVIg therapeutic approach. In particular, the Fc variants of the present invention that bind with greater affinity to the FcγRIIb receptor than parent Fc polypeptide may be used. Such Fc variants would thus function as FcγRIIb agonists, and would be expected to enhance the beneficial effects of IVIg as an autoimmune disease therapeutic and also as a modulator of B-cell proliferation. In addition, such FcγRIIb-enhanced Fc variants may also be further modified to have the same or limited binding to other receptors. In additional embodiments, the Fc variants with enhanced FcγRIIb affinity may be combined with mutations that reduce or ablate to other receptors, thereby potentially further minimizing side effects during therapeutic use.

Such immunomodulatory applications of the Fc variants of the present invention may also be utilized in the treatment of oncological indications, especially those for which antibody therapy involves antibody-dependant cytotoxic mechanisms. For example, an Fc variant that enhances affinity to FcγRIIb may be used to antagonize this inhibitory receptor, for example by binding to the Fc/FcγRIIb binding site but failing to trigger, or reducing cell signaling, potentially enhancing the effect of antibody-based anti-cancer therapy. Such Fc variants, functioning as FcγRIIb antagonists, may either block the inhibitory properties of FcγRIIb, or induce its inhibitory function as in the case of IVIg. An FcγRIIb antagonist may be used as co-therapy in combination with any other therapeutic, including but not limited to antibodies, acting on the basis of ADCC related cytotoxicity. FcγRIIb antagonistic Fc variants of this type are preferably isolated Fc or Fc fragments, although in alternate embodiments antibodies and Fc fusions may be used.

Glycoform Modifications

Many polypeptides, including antibodies, are subjected to a variety of post-translational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation (Lifely et al., 1995, Glycobiology 5(8): 813-822).

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate (Jefferis et al., 1998, Immunol. Rev. 163:59-76; Wright et al., 1997, Trends Biotech 15:26-32). For human IgG, the core oligosaccharide normally consists of $GlcNAc_2Man_3GlcNAc$, with differing numbers of outer residues.

The carbohydrate moieties of the present invention will be described with reference to commonly used nomenclature for the description of oligosaccharides. A review of carbohydrate chemistry which uses this nomenclature is found in Hubbard et al. 1981, Ann. Rev. Biochem. 50:555-583. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of the present invention occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991).

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)$_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyl-transferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

The present invention contemplates Fc variants that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In a preferred embodiment, the Fc variants of the present invention are modified to control the level of fucosylated and/or bisecting oligosaccharides that are covalently attached to the Fc region. A variety of methods are well known in the art for generating modified glycoforms (Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. Nos. 10/277,370; 10/113,929; PCT WO 00/61739A1; PCT WO 01/29246A1; PCT WO 02/31140A1; PCT WO 02/30954A1); (Potelligent™ technology [Biowa, Inc., Princeton, N.J.]; GlycoMAb™ glycosylation engineering technology [GLYCART biotechnology AG, Zürich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyl-transferase] and/or β1-4-N-acetylglucosaminyltransferase III [GnTIII]), or by modifying carbohydrate(s) after the IgG has been expressed. The use of a particular mode of generating a modified glycoform, for example the use of the Lec-13 cell line in the present study, is not meant to constrain the present invention to that particular embodiment. Rather, the present invention contemplates Fc variants with modified glycoforms irrespective of how they are produced.

Other methods for modifying glycoforms of the Fc variants of the invention include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). Methods for modying glycoforms include but are not limited to using a glycoengineered strain of yeast *Pichia pastoris* (Li et al., 2006, Nature Biotechnology 24(2):210-215), a glycoengineered strain of the moss *Physcomitrella patens* wherein the enzymes β1,2-xylosyltransferase and/or α1,3- fucosyltransferase are knocked out in (Nechansky et al., 2007, Mol Immunjol 44(7):1826-8), and the use of RNA interference to inhibit endogenous alpha-1,3-fucosyltransferase and/or beta-1,2-xylosyltransferase in the aquatic plant Lemna minor (Cox et al., 2006, Nat Biotechnol 24(12):1591-7).

Engineered glycoform typically refers to the different carbohydrate or oligosaccharide; thus for example an Fc variant may comprise an engineered glycoform. Alternatively, engineered glycoform may refer to the Fc variant that comprises the different carbohydrate or oligosaccharide. For the purposes of modified glycoforms described herein, a "parent antibody" is a glycosylated antibody having the same amino acid sequence and mature core carbohydrate structure as an engineered glycoform of the present invention, except that fucose is attached to the mature core carbohydrate structure of the parent antibody. For instance, in a composition comprising the parent glycoprotein about 50-100% or about 70-100% of the parent glycoprotein comprises a mature core carbohydrate structure having fucose attached thereto.

The present invention provides a composition comprising a glycosylated Fc variant having an Fc region, wherein about 51-100% of the glycosylated antibody in the composition comprises a mature core carbohydrate structure which lacks fucose, attached to the Fc region of the antibody. More preferably, about 80-100% of the antibody in the composition comprises a mature core carbohydrate structure which lacks fucose and most preferably about 90-99% of the antibody in the composition lacks fucose attached to the mature core carbohydrate structure. In a most preferred embodiment, the antibody in the composition both comprises a mature core carbohydrate structure that lacks fucose and additionally comprises at least one amino acid modification in the Fc region. In the most preferred embodiment, the combination of engineered glycoform and amino acid modification provides optimal Fc receptor binding properties to the antibody.

Other Modifications

Fc variants of the present invention may comprise one or more modifications that provide optimized properties that are not specifically related to FcγR- or complement-mediated effector functions per se. Said modifications may be amino acid modifications, or may be modifications that are made enzymatically or chemically. Such modification(s) likely provide some improvement in the Fc variant, for example an enhancement in its stability, solubility, function, or clinical use. The present invention contemplates a variety of improvements that made be made by coupling the Fc variants of the present invention with additional modifications.

In one embodiment, the variable region of an antibody of the present invention may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the target antigen.

Fc variants of the invention may comprise one or more modifications that provide reduced or enhanced internalization of an Fc variant. In one embodiment, Fc variants of the present invention can be utilized or combined with additional modifications in order to reduce the cellular internalization of an Fc variant that occurs via interaction with one or more Fc ligands. This property might be expected to enhance effector function, and potentially reduce immunogenicity of the Fc variants of the invention. Alternatively, Fc variants of the present invention can be utilized directly or combined with additional modifications in order to enhance the cellular internalization of an Fc variant that occurs via interaction with one or more Fc ligands. For example, in a preferred embodiment, an Fc variant is used that provides enhanced binding to FcγRI, which is expressed on dendritic cells and active early in immune response. This strategy could be further enhanced by combination with additional modifications, either within the Fc variant or in an attached fusion or conjugate partner, that promote recognition and presentation of Fc peptide fragments by MHC molecules. These strategies are expected to enhance target antigen processing and thereby improve antigenicity of the target antigen (Bonnerot and Amigorena, 1999, *Immunol Rev.* 172:279-84, incorporated entirely by reference), promoting an adaptive immune response and greater target cell killing by the human immune system. These strategies may be particularly advantageous when the targeted antigen is shed from the cellular surface. An additional application of these concepts arises with idiotype vaccine immunotherapies, in which clone-specific antibodies produced by a patient's lymphoma cells are used to vaccinate the patient.

In a preferred embodiment, modifications are made to improve biophysical properties of the Fc variants of the present invention, including but not limited to stability, solubility, and oligomeric state. Modifications can include, for example, substitutions that provide more favorable intramolecular interactions in the Fc variant such as to provide greater stability, or substitution of exposed nonpolar amino acids with polar amino acids for higher solubility. A number of optimization goals and methods are described in U.S. Ser. No. 10/379,392, incorporated entirely by reference, that may find use for engineering additional modifications to further optimize the Fc variants of the present invention. The Fc variants of the present invention can also be combined with additional modifications that reduce oligomeric state or size, such that tumor penetration is enhanced, or in vivo clearance rates are increased as desired.

Other modifications to the Fc variants of the present invention include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., 2001, *J. Immunol.*, 2001, 166: 1320-1326; Stevenson et al., 2002, *Recent Results Cancer Res.* 159: 104-12; U.S. Pat. No. 5,681,566; Caron et al., 1992, J. Exp. Med. 176:1191-1195, and Shopes, 1992, J. Immunol. 148(9): 2918-22, all incorporated enirely by reference. Additional modifications to the variants of the present invention include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, J. Mol. Biol. 270(1):26-35, and Carter et al., 2001, J. Immunol. Methods 248:7-15, both incorporated entirely by reference. Additional modifications include modifications in the hinge and CH3 domains, in which the modifications reduce the propensity to form dimers.

In further embodiments, the Fc variants of the present invention comprise modifications that remove proteolytic degradation sites. These may include, for example, protease sites that reduce production yields, as well as protease sites that degrade the administered protein in vivo. In a preferred embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains (T. E. Creighton, Proteins: Structure and Molecular Properties, W.H. Freeman & Co., San Francisco, pp. 79-86 (1983), incorporated entirely by reference), acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The Fc variants of the present invention may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101(2):7566-71, Zhang et al., 2003, 303(5656):371-3, and Chin et al., 2003, Science 301(5635):964-7, all incorporated enirely by reference. In some embodiments, these modifications enable manipulation of various functional, biophysical, immunological, or manufacturing properties discussed above. In additional embodiments, these modifications enable additional chemical modification for other purposes. Other modifications are contemplated herein. For example, the Fc variant may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the Fc variants. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the Fc variants of the present invention.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an anti-XXXX antibody of the present invention. See for example U.S. Ser. Nos. 09/903,378, 10/754,296, 11/249,692, and references cited therein, all expressly incorporated by reference.

In particularly preferred embodiments of the invention, Fc variants of the present invention may be combined with Fc variants that alter FcRn binding. Such variants may provide improved pharmacokinetic properties to the Fc variants of the invention. In particular, variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Jounal of Immunology 176:346-356, U.S. Ser. No. 11/102,621, PCT/US2003/033037, PCT/US2004/011213, U.S. Ser. Nos. 10/822,300, 10/687,118, PCT/US2004/034440, U.S. Ser. No. 10/966,673 all entirely incorporated by reference), 256A, 272A, 286A, 305A, 307A, 311A, 312A, 376A, 378Q, 380A, 382A, 434A (Shields et al, Journal of Biological Chemistry, 2001, 276(9):6591-6604, U.S. Ser. No. 10/982,470, U.S. Pat. No. 6,737,056, U.S. Ser. Nos. 11/429,793, 11/429,786, PCT/US2005/029511, U.S. Ser. No. 11/208,422, all entirely incorporated by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311 S (Dall Acqua et al. Journal of Immunology, 2002, 169:5171-5180, U.S. Pat. No. 7,083,784, PCT/US97/03321, U.S. Pat. No. 6,821,505, PCT/US01/48432, U.S. Ser. No. 11/397,328, all entirely incorporated by reference), 257C, 257M, 257L, 257N, 257Y, 279E, 279Q, 279Y, insertion of Ser after 281, 283F, 284E, 306Y, 307V, 308F, 308Y 311V, 385H, 385N, (PCT/US2005/041220, U.S. Ser. Nos. 11/274,065, 11/436,266 all entirely incorporated by reference) 204D, 284E, 285E, 286D, and 290E (PCT/US2004/037929 entirely incorporated by reference).

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the covalent modification of the antibodies of the invention comprises the addition of one or more labels. The term "labeling group" means any detectable label. In some embodiments, the labeling group is coupled to the antibody via spacer arms of various lengths to reduce potential steric hindrance. Various methods for labeling proteins are known in the art and may be used in performing the present invention. In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art and may be used in performing the present invention. Specific labels include optical dyes, including, but not limited to, chromophores, phosphors and fluorophores, with the latter being specific in many instances. Fluorophores can be either "small molecule" fluores, or proteinaceous fluores. By "fluorescent label" is meant any molecule that may be detected via its inherent fluorescent properties.

Production of Fc Variants

The present invention provides methods for producing and experimentally testing Fc variants. The described methods are not meant to constrain the present invention to any particular application or theory of operation. Rather, the provided methods are meant to illustrate generally that one or more Fc variants may be produced and experimentally tested to obtain Fc variants. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76; Antibodies: A Laboratory Manual by Harlow & Lane, New York: Cold Spring Harbor Laboratory Press, 1988, all incorporated enirely by reference.

In one embodiment of the present invention, nucleic acids are created that encode the Fc variants, and that may then be cloned into host cells, expressed and assayed, if desired. Thus, nucleic acids, and particularly DNA, may be made that encode each protein sequence. These practices are carried out using well-known procedures. For example, a variety of methods that may find use in the present invention are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons), both incorporated entirely by reference. As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or amino acid substitutions at variable positions, a physical library comprising nucleic acids that encode the library sequences, or a physical library comprising the variant proteins, either in purified or unpurified form. Accordingly, there are a variety of techniques that may be used to efficiently generate libraries of the present invention. Such methods that may find use in the present invention are described or referenced in U.S. Pat. No. 6,403,312; U.S. Ser. Nos. 09/782,004; 09/927,790; 10/218,102; PCT WO 01/40091; and PCT WO 02/25588, all incorporated entirely by reference. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode Fc variants.

The Fc variants of the present invention may be produced by culturing a host cell transformed with nucleic acid, preferably an expression vector, containing nucleic acid encoding the Fc variants, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in the present invention are described in the ATCC® cell line catalog, available from the American Type Culture Collection.

In a preferred embodiment, the Fc variants are expressed in mammalian expression systems, including systems in which the expression constructs are introduced into the mammalian cells using virus such as retrovirus or adenovirus. Any mammalian cells may be used, with human, mouse, rat, hamster, and primate cells being particularly preferred. Suitable cells also include known research cells, including but not limited to Jurkat T cells, NIH3T3, CHO, BHK, COS, HEK293, PER C.6, HeLa, Sp2/0, NS0 cells and variants thereof. In an alternately preferred embodiment, library proteins are expressed in bacterial cells. Bacterial expression systems are well known in the art, and include Escherichia coli (E. coli), Bacillus subtilis, Streptococcus cremoris, and Streptococcus lividans. In alternate embodiments, Fc variants are produced in insect cells (e.g. Sf21/Sf9, Trichoplusia ni Bti-Tn5b1-4) or yeast cells (e.g. S. cerevisiae, Pichia, etc). In an alternate embodiment, Fc variants are expressed in vitro using cell free translation systems. In vitro translation systems derived from both prokaryotic (e.g. E. coli) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the Fc variants may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the Fc variants of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing Fc variants.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the Fc variant, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Fc variants may be operably linked to a fusion partner to enable targeting of the expressed protein, purification, screening, display, and the like. Fusion partners may be linked to the Fc variant sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs Fc variant and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an Fc variant may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen Fc variants (see below). Fusion partners that enable a variety of selection methods are well-known in the art, and all of these find use in the present invention. For example, by fusing the members of an Fc variant library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317, incorporated entirely by reference). Fusion partners may enable Fc variants to be labeled. Alternatively, a fusion partner may bind to a specific sequence on the expression vector, enabling the fusion partner and associated Fc variant to be linked covalently or noncovalently with the nucleic acid that encodes them. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In a preferred embodiment, Fc variants are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of Fc variants. For example, the bacterial proteins A and G bind to the Fc region. Likewise, the bacterial protein L binds to the Fab region of some antibodies, as of course does the antibody's target antigen. Purification can often be enabled by a particular fusion partner. For example, Fc variants may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, N.Y., 1994, incorporated entirely by reference. The degree of purification necessary will vary depending on the screen or use of the Fc variants. In some instances no purification is necessary. For example in one embodiment, if the Fc variants are secreted, screening may take place directly from the media. As is well known in the art, some methods of selection do not involve purification of proteins. Thus, for example, if a library of Fc variants is made into a phage display library, protein purification may not be performed.

In Vitro Experimentation

Fc variants may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the Fc variants of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In a preferred embodiment, the functional and/or biophysical properties of Fc variants are screened in an in vitro assay. In vitro assays may allow a broad dynamic range for screening properties of interest. Properties of Fc variants that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of Fc variants to a protein or nonprotein molecule that is known or thought to bind the Fc variant. In a preferred embodiment, the screen is a binding assay for measuring binding to the target antigen. In an alternately preferred embodiment, the screen is an assay for binding of Fc variants to an Fc ligand, including but are not limited to the family of FcγRs, the neonatal receptor FcRn, the complement protein C1q, and the bacterial proteins A and G. Said Fc ligands may be from any organism, with humans, mice, rats, rabbits, and monkeys preferred. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label of the Fc variant. Assays may employ a variety of detection methods including but not limited to chromogenic, fluorescent, luminescent, or isotopic labels.

The biophysical properties of Fc variants, for example stability and solubility, may be screened using a variety of methods known in the art. Protein stability may be determined by measuring the thermodynamic equilibrium between folded and unfolded states. For example, Fc variants of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an Fc variant may be quantitatively or qualitatively determined using a wide range of methods that are known in the art. Methods which may find use in the present invention for characterizing the biophysical properties of Fc variants include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an Fc variant could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the Fc variant's stability and solubility.

In a preferred embodiment, the library is screened using one or more cell-based or in vitro assays. For such assays, Fc variants, purified or unpurified, are typically added exogenously such that cells are exposed to individual variants or groups of variants belonging to a library. These assays are typically, but not always, based on the biology of the ability of the Fc variant to bind to the target antigen and mediate some biochemical event, for example effector functions like cellular lysis, phagocytosis, ligand/receptor binding inhibition, inhibition of growth and/or proliferation, apoptosisand the like. Such assays often involve monitoring the response of cells to Fc variant, for example cell survival, cell death, cellular phagocytosis, cell lysis, change in cellular morphology, or transcriptional activation such as cellular expression of a natural gene or reporter gene. For example, such assays may measure the ability of Fc variants to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferationor activation to be monitored. In a preferred embodiment, the DELFIA® EuTDA-based cytotoxicity assay (Perkin Elmer, MA) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an Fc variant. Cell types for such assays may be prokaryotic or eukaryotic, and a variety of cell lines that are known in the art may be employed. Alternatively, cell-based screens are performed using cells that have been transformed or transfected with nucleic acids encoding the Fc variants.

In vitro assays include but are not limited to binding assays, ADCC, CDC, cytotoxicity, proliferation, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

In Vivo Experimentation

The biological properties of the Fc variants of the present invention may be characterized in cell, tissue, and whole organism experiments. As is know in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the Fc variants of the present invention, a particular challenge arises when using animal models to evaluate the potential for in-human efficacy of candidate polypeptides—this is due, at least in part, to the fact that Fc variants that have a specific effect on the affinity for a human Fc receptor may not have a similar affinity effect with the orthologous animal receptor. These problems can be further exacerbated by the inevitable ambiguities associated with correct assignment of true orthologues (Mechetina et al., Immunogenetics, 2002 54:463-468, incorporated entirely by reference), and the fact that some orthologues simply do not exist in the animal (e.g. humans possess an FcγRIIa whereas mice do not). Therapeutics are often tested in mice, including but not limited to nude mice, SCID mice, xenograft mice, and transgenic mice (including knockins and knockouts). For example, an Fc variant of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the Fc variant to reduce or inhibit cancer growth and metastasis. An alternative approach is the use of a SCID murine model in which immune-deficient mice are injected with human PBLs, conferring a semi-functional and human immune system—with an appropriate array of human FcRs- to the mice that have subsequently been injected with antibodies or Fc-polypeptides that target injected human tumor cells. In such a model, the Fc-polypeptides that target the desired antigen (such as her2/neu on SkOV3 ovarian cancer cells) interact with human PBLs within the mice to engage tumoricidal effector functions. Such experimentation may provide meaningful data for determination of the potential of said Fc variant to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the Fc variants of the present invention. Tests of the Fc variants of the present invention in humans are ultimately required for approval as drugs, and thus of course these experiments are contemplated. Thus the Fc variants of the present invention may be tested in humans to determine their therapeutic efficacy, toxicity, pharmacokinetics, and/or other clinical properties.

The Fc variants of the present invention may confer superior performance on Fc-containing therapeutics in animal models or in humans. The receptor binding profiles of such Fc variants, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an Fc variant with reduced binding to FcγRIIIa, FcγRI and FcγRIIa can be selected to eliminate most cell-mediated effector function, or an Fc variant with reduced binding to C1q may be selected to limit complement-mediated effector functions. In some contexts, such effector functions are known to have potential toxic effects, therefore eliminating them may increase the safety of the Fc-bearing drug and such improved safety may be characterized in animal models. In some contexts, such effector functions are known to mediate the desirable therapeutic activity, therefore enhancing them may increase the activity or potency of the Fc-bearing drug and such improved activity or potency may be characterized in animal models.

Optimized Fc variants can be tested in a variety of orthotopic tumor models. These clinically relevant animal models are important in the study of pathophysiology and therapy of aggressive cancers like pancreatic, prostate and breast cancer. Immune deprived mice including, but not limited to athymic nude or SCID mice are frequently used in scoring of local and systemic tumor spread from the site of intraorgan (e.g. pancreas, prostate or mammary gland) injection of human tumor cells or fragments of donor patients.

In preferred embodiments, Fc variants of the present invention may be assessed for efficacy in clinically relevant animal models of various human diseases. In many cases, relevant models include various transgenic animals for specific tumor antigens.

Relevant transgenic models such as those that express human Fc receptors (e.g., CD16 including the gamma chain, FcγR1, RIIa/b, and others) could be used to evaluate and test Fc variant antibodies and Fc-fusions in their efficacy. The evaluation of Fc variants by the introduction of human genes that directly or indirectly mediate effector function in mice or other rodents that may enable physiological studies of efficacy in tumor toxicity or other diseases such as autoimmune disorders and RA. Human Fc receptors such as FcγRIIIa may possess polymorphisms such as that in position 158 V or F which would further enable the introduction of specific and combinations of human polymorphisms into rodents. The various studies involving polymorphism-specific FcRs is not limited to this section, however encompasses all discussions and applications of FcRs in general as specified in throughout this application. Fc variants of the present invention may confer superior activity on Fc-containing drugs in such transgenic models, in particular variants with binding profiles optimized for human FcγRIIIa mediated activity may show superior activity in transgenic CD16 mice. Similar improvements in efficacy in mice transgenic for the other human Fc receptors, e.g. FcγRIIa, FcγRI, etc., may be observed for Fc variants with binding profiles optimized for the respective receptors. Mice transgenic for multiple human receptors would show improved activity for Fc variants with binding profiles optimized for the corresponding multiple receptors.

Because of the difficulties and ambiguities associated with using animal models to characterize the potential efficacy of candidate therapeutic antibodies in a human patient, some variant polypeptides of the present invention may find utility as proxies for assessing potential in-human efficacy. Such proxy molecules would preferably mimic—in the animal system—the FcR and/or complement biology of a corresponding candidate human Fc variant. This mimicry is most likely to be manifested by relative association affinities between specific Fc variants and animal vs. human receptors. For example, if one were using a mouse model to assess the potential in-human efficacy of an Fc variant that has enhanced affinity for human FcγRIIIa, an appropriate proxy variant would have enhanced affinity for mouse FcγRIII-2 (mouse CD16-2). Alternatively if one were using a mouse model to assess the potential in-human efficacy of an Fc variant that has reduced affinity for the inhibitory human FcγRIIb, an appropriate proxy variant would have reduced affinity for mouse FcγRII. It should also be noted that the proxy Fc variants could be created in the context of a human Fc variant, an animal Fc variant, or both.

In a preferred embodiment, the testing of Fc variants may include study of efficacy in primates (e.g. cynomolgus monkey model) to facilitate the evaluation of depletion of specific target cells harboring the target antigen. Additional primate models include but not limited to that of the rhesus monkey and Fc polypeptides in therapeutic studies of autoimmune, transplantation and cancer.

Toxicity studies are performed to determine the antibody or Fc-fusion related-effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therepeutics, naked or conjugated are evaluated for cross-reactivity with normal tissues, immunogenicity/antibody production, conjugate or linker toxicity and "bystander" toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/contaminants have been removed, that the test material is comparable throughout development, and GLP compliance.

The pharmacokinetics (PK) of the Fc variants of the invention can be studied in a variety of animal systems, with the most relevant being non-human primates such as the cynomolgus, rhesus monkeys. Single or repeated i.v./s.c. administrations over a dose range of 6000-fold (0.05-300 mg/kg) can be evaluated for the half-life (days to weeks) using plasma concentration and clearance as well as volume of distribution at a steady state and level of systemic absorbance can be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T1/2). Additional measured parameters could include compartmental analysis of concentration-time data obtained following i.v. administration and bioavailability. Examples of pharmacological/toxicological studies using cynomolgus have been established for Rituxan and Zevalin in which monoclonal antibodies to CD20 are cross-reactive. Biodistribution, dosimetry (for radiolabled antibodies), and PK studies can also be done in rodent models. Such studies would evaluate tolerance at all doses administered, toxicity to local tissues, preferential localization to rodent xenograft animal models, depletion of target cells (e.g. CD20 positive cells).

The Fc variants of the present invention may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of Fc variants of the present invention. Because Fc variants of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific tumor cells or blocking signaling mechanisms, measuring depletion of target antigen expressing cells or signals, etc. The Fc variants of the present invention may target particular effector cell populations and thereby direct Fc-containing drugs to recruit certain activities to improve potency or to increase penetration into a particularly favorable physiological compartment. For example, neutrophil activity and localization can be targeted by an Fc variant that preferentially targets FcγRIIIb. Such pharmacodynamic effects may be demonstrated in animal models or in humans.

Clinical Use

The Fc variants of the present invention may find use in a wide range of products. In one embodiment the Fc variant of the present invention is a therapeutic, a diagnostic, or a research reagent, preferably a therapeutic. Alternatively, the Fc variants of the present invention may be used for agricultural or industrial uses.

The Fc variants of the present invention may be used for various therapeutic purposes. As will be appreciated by those in the art, the Fc variants of the present invention may be used for any therapeutic purpose that antibodies, and the like may be used for. In a preferred embodiment, the Fc variants are administered to a patient to treat disorders including but not limited to autoimmune and inflammatory diseases, infectious diseases, and cancer.

A "patient" for the purposes of the present invention includes both humans and other animals, preferably mammals and most preferably humans. Thus the Fc variants of the present invention have both human therapy and veterinary applications. The term "treatment" or "treating" in the present invention is meant to include therapeutic treatment, as well as prophylactic, or suppressive measures for a disease or disorder. Thus, for example, successful administration of an Fc variant prior to onset of the disease results in treatment of the disease. As another example, successful administration of an optimized Fc variant after clinical manifestation of the disease to combat the symptoms of the disease comprises treatment of the disease. "Treatment" and "treating" also encompasses administration of an optimized Fc variant after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an Fc variant of the present invention is administered to a patient having a disease involving inappropriate expression of a protein or other molecule. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the Fc variants of the present invention.

By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia; tumors of the central nervous system such as glioma, glioblastoma, neuroblastoma, astrocytoma, medulloblastoma, ependymoma, and retinoblastoma; solid tumors of the head and neck (eg. nasopharyngeal cancer, salivary gland carcinoma, and esophageal cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

By "autoimmune diseases" herein include allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis, type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Reynauld's phenomenon, Reiter's syndrome, rheumatoid arthritis, sarcoidosis, scleroderma, Sjorgen's syndrome, solid organ transplant rejection, stiff-man syndrome, systemic lupus erythematosus, takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

By "inflammatory disorders" herein include acute respiratory distress syndrome (ARDS), acute septic arthritis, adjuvant arthritis (Prakken et al., Springer Semin Immunopathol., 2003 August; 25(1):47-63, incorporated entirely by reference), juvenile idiopathic arthritis (de Kleer et al., Arthritis Rheum. 2003 July; 47(7):2001-10, incorporated entirely by reference), allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, respiratory syncytial virus, rinderpest, rhinovirus, rotavirus, rubella, SARS virus, smallpox, viral meningitis, and the like. Infections diseases may also be caused by bacteria including *Bacillus antracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis,*

*Pseudomonas aeruginosa, S. pneumonia, Streptococcus, Staphylococcus, Vibria cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as chlamydia, kokzidioa, leishmania, malaria, rickettsia, trypanosoma, and the like.

Furthermore, antibodies of the present invention may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological conditions.

A number of the receptors that may interact with the Fc variants of the present invention are polymorphic in the human population. For a given patient or population of patients, the efficacy of the Fc variants of the present invention may be affected by the presence or absence of specific polymorphisms in proteins. For example, FcγRIIIa is polymorphic at position 158, which is commonly either V (high affinity) or F (low affinity). Patients with the V/V homozygous genotype are observed to have a better clinical response to treatment with the anti-CD20 antibody Rituxan® (rituximab), likely because these patients mount a stronger NK response (Dall'Ozzo et. al. (2004) Cancer Res. 64:4664-9, incorporated entirely by reference). Additional polymorphisms include but are not limited to FcγRIIa R131 or H131, and such polymorphisms are known to either increase or decrease Fc binding and subsequent biological activity, depending on the polymorphism. Fc variants of the present invention may bind preferentially to a particular polymorphic form of a receptor, for example FcγRIIIa 158 V, or to bind with equivalent affinity to all of the polymorphisms at a particular position in the receptor, for example both the 158V and 158F polymorphisms of FcγRIIIa. In a preferred embodiment, Fc variants of the present invention may have equivalent binding to polymorphisms may be used in an antibody to eliminate the differential efficacy seen in patients with different polymorphisms. Such a property may give greater consistency in therapeutic response and reduce non-responding patient populations. Such variant Fc with identical binding to receptor polymorphisms may have increased biological activity, such as ADCC, CDC or circulating half-life, or alternatively decreased activity, via modulation of the binding to the relevant Fc receptors. In a preferred embodiment, Fc variants of the present invention may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing a polymorphism with a higher affinity for an inhibitory receptor such as FcγRIIb could receive a drug containing an Fc variant with reduced binding to such polymorphic form of the receptor, creating a more efficacious drug.

In a preferred embodiment, patients are screened for one or more polymorphisms in order to predict the efficacy of the Fc variants of the present invention. This information may be used, for example, to select patients to include or exclude from clinical trials or, post-approval, to provide guidance to physicians and patients regarding appropriate dosages and treatment options. For example, in patients that are homozygous or heterozygous for FcγRIIIa 158F antibody drugs such as the anti-CD20 mAb, Rituximab are minimially effective (Carton 2002 Blood 99: 754-758; Weng 2003 J. Clin. Oncol. 21:3940-3947, both incorporated entirely by reference); such patients may show a much better clinical response to the antibodies of the present invention. In one embodiment, patients are selected for inclusion in clinical trials for an antibody of the present invention if their genotype indicates that they are likely to respond significantly better to an antibody of the present invention as compared to one or more currently used antibody therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an Fc variant engineered to be specifically efficacious for such population, or alternatively where such therapy contains an Fc variant that does not show differential activity to the different forms of the polymorphism.

Included in the present invention are diagnostic tests to identify patients who are likely to show a favorable clinical response to an Fc variant of the present invention, or who are likely to exhibit a significantly better response when treated with an Fc variant of the present invention versus one or more currently used antibody therapeutics. Any of a number of methods for determining FcγR polymorphisms in humans known in the art may be used.

Furthermore, the present invention comprises prognostic tests performed on clinical samples such as blood and tissue samples. Such tests may assay for effector function activity, including but not limited to ADCC, CDC, phagocytosis, and opsonization, or for killing, regardless of mechanism, of cancerous or otherwise pathogenic cells. In a preferred embodiment, ADCC assays, such as those described previously, are used to predict, for a specific patient, the efficacy of a given Fc variant of the present invention. Such information may be used to identify patients for inclusion or exclusion in clinical trials, or to inform decisions regarding appropriate dosages and treatment regemins. Such information may also be used to select a drug that contains a particular Fc variant that shows superior activity in such assay.

Formulation

Pharmaceutical compositions are contemplated wherein an antibody of the present invention and one or more therapeutically active agents are formulated. Formulations of the antibodies of the present invention are prepared for storage by mixing said antibody having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues)

polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In a preferred embodiment, the pharmaceutical composition that comprises the antibody of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The antibodies disclosed herein may also be formulated as immunoliposomes. A liposome is a small vesicle comprising various types of lipids, phospholipids and/or surfactant that is useful for delivery of a therapeutic agent to a mammal. Liposomes containing the antibody are prepared by methods known in the art, such as described in Epstein et al., 1985, *Proc Natl Acad Sci USA*, 82:3688; Hwang et al., 1980, *Proc Natl Acad Sci USA*, 77:4030; U.S. Pat. Nos. 4,485,045; 4,544,545; and PCT WO 97/38731, all incorporated entirely by reference. Liposomes with enhanced circulation time are disclosed in U.S. Pat. No. 5,013,556, incorporated entirely by reference. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, *J National Cancer Inst* 81:1484, incorporated entirely by reference).

The antibody and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated entirely by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919, incorporated entirely by reference), copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(–)-3-hydroxybutyric acid, and Pro-Lease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an antibody of the present invention, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the antibody may be directly applied as a solution or spray. As is known in the art, the pharmaceutical composition may be formulated accordingly depending upon the manner of introduction.

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate (see WO 04091658, incorporated entirely by reference). Antibodies of the present invention may be more amenable to subcutaneous administration due to, for example, increased potency, improved serum half-life, or enhanced solubility.

As is known in the art, protein therapeutics are often delivered by IV infusion or bolus. The antibodies of the present invention may also be delivered using such methods. For example, administration may venious be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Antibodies of the present invention may be more amenable to intrapulmonary delivery. FcRn is present in the lung, and may promote transport from the lung to the bloodstream (e.g. Syntonix WO 04004798, Bitonti et al. (2004) Proc. Nat. Acad. Sci. 101:9763-8, both incorporated entirely by reference). Accordingly, antibodies that bind FcRn more effectively in the lung or that are released more efficiently in the bloodstream may have improved bioavailability following intrapulmonary administration. Antibodies of the present invention may also be more amenable to intrapulmonary administration due to, for example, improved solubility or altered isoelectric point.

Furthermore, antibodies of the present invention may be more amenable to oral delivery due to, for example, improved stability at gastric pH and increased resistance to proteolysis. Furthermore, FcRn appears to be expressed in the intestinal epithelia of adults (Dickinson et al. (1999) J. Clin. Invest. 104:903-11, incorporated entirely by reference), so antibodies of the present invention with improved FcRn interaction profiles may show enhanced bioavailability following oral administration. FcRn mediated transport of antibodies may also occur at other mucus membranes such as those in the gastrointestinal, respiratory, and genital tracts (Yoshida et al. (2004) Immunity 20:769-83, incorporated entirely by reference).

In addition, any of a number of delivery systems are known in the art and may be used to administer the antibodies of the present invention. Examples include, but are not limited to, encapsulation in liposomes, microparticles, microspheres (eg. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol), polylactides, copolymers of L-glutamic acid and ethyl-L-gutamate, ethylene-vinyl acetate, lactic acid-glycolic acid copolymers such as the Lupron Depot®, and poly-D-(−)-3-hydroxyburyric acid. It is also possible to administer a nucleic acid encoding the antibody of the current invention, for example by retroviral infection, direct injection, or coating with lipids, cell surface receptors, or other transfection agents. In all cases, controlled release systems may be used to release the antibody at or close to the desired location of action.

Dosing

The dosing amounts and frequencies of administration are, in a preferred embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active antibody in the formulation may vary from about 0.1 to 100 weight %. In a preferred embodiment, the concentration of the antibody is in the range of 0.003 to 1.0 molar. In order to treat a patient, a therapeutically effective dose of the antibody of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, with 1 to 10 mg/kg being preferred.

In some embodiments, only a single dose of the antibody is used. In other embodiments, multiple doses of the antibody are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the antibodies of the present invention are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the antibody of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The antibodies of the present invention may be administered concomitantly with one or more other therapeutic regimens or agents. The additional therapeutic regimes or agents may be used to improve the efficacy or safety of the antibody. Also, the additional therapeutic regimes or agents may be used to treat the same disease or a comorbidity rather than to alter the action of the antibody. For example, an antibody of the present invention may be administered to the patient along with chemotherapy, radiation therapy, or both chemotherapy and radiation therapy. The antibody of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional antibodies, FcγRIIb or other Fc receptor inhibitors, or other therapeutic agents.

The terms "in combination with" and "co-administration" are not limited to the administration of said prophylactic or therapeutic agents at exactly the same time. Instead, it is meant that the antibody of the present invention and the other agent or agents are administered in a sequence and within a time interval such that they may act together to provide a benefit that is increased versus treatment with only either the antibody of the present invention or the other agent or agents. It is preferred that the antibody and the other agent or agents act additively, and especially preferred that they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the antibodies of the present invention are administered with one or more additional molecules comprising antibodies or Fc. The antibodies of the present invention may be co-administered with one or more other antibodies that have efficacy in treating the same disease or an additional comorbidity; for example two antibodies may be administered that recognize two antigens that are overexpressed in a given type of cancer, or two antigens that mediate pathogenesis of an autoimmune or infectious disease.

Examples of anti-cancer antibodies that may be co-administered include, but are not limited to, anti-17-1A cell surface antigen antibodies such as Panorex™ (edrecolomab); anti-4-1BB antibodies; anti-4Dc antibodies; anti-A33 antibodies such as A33 and CDP-833; anti-α4β1 integrin antibodies such as natalizumab; anti-α4β7 integrin antibodies such as LDP-02; anti-α4β1 integrin antibodies such as F-200, M-200, and SJ-749; anti-αVβ3 integrin antibodies such as abciximab, CNTO-95, Mab-17E6, and Vitaxin™ anti-complement factor 5 (C5) antibodies such as 5G1.1; anti-CA125 antibodies such as OvaRex® (oregovomab); anti-CD3 antibodies such as Nuvion® (visilizumab) and Rexomab; anti-CD4 antibodies such as IDEC-151, MDX-CD4, OKT4A; anti-CD6 antibodies such as Oncolysin B and Oncolysin CD6; anti-CD7 antibodies such as HB2; anti-CD19 antibodies such as B43, MT-103, and Oncolysin B; anti-CD20 antibodies such as 2H7, 2H7.v16, 2H7.v114, 2H7.v115, Bexxar® (tositumomab, I-131 labeled anti-CD20), Rituxan® (rituximab), and Zevalin® (Ibritumomab tiuxetan, Y-90 labeled anti-CD20); anti-CD22 antibodies such as Lymphocide™ (epratuzumab, Y-90 labeled anti-CD22); anti-CD23 antibodies such as IDEC-152; anti-CD25 antibodies such as basiliximab and Zenapax® (daclizumab); anti-CD30 antibodies such as AC10, MDX-060, and SGN-30; anti-CD33 antibodies such as Mylotarg® (gemtuzumab ozogamicin), Oncolysin M, and Smart M195; anti-CD38 antibodies; anti-CD40 antibodies such as SGN-40 and toralizumab; anti-CD40L antibodies such as 5c8, Antova™ and IDEC-131; anti-CD44 antibodies such as bivatuzumab; anti-CD46 antibodies; anti-CD52 antibodies such as Campath® (alemtuzumab); anti-CD55 antibodies such as SC-1; anti-CD56 antibodies such as huN901-DM1; anti-CD64 antibodies such as MDX-33; anti-CD66e antibodies such as XR-303; anti-CD74 antibodies such as IMMU-110; anti-CD80 antibodies such as galiximab and IDEC-114; anti-CD89 antibodies such as MDX-214; anti-CD123 antibodies; anti-CD138 antibodies such as B-B4-DM1; anti-CD146 antibodies such as AA-98; anti-CD148 antibodies; anti-CEA antibodies such as cT84.66, labetuzumab, and Pentacea™ anti-CTLA-4 antibodies such as MDX-101; anti-CXCR4 antibodies; anti-EGFR antibodies such as ABX-EGF, Erbitux® (cetuximab), IMC-C225, and Merck Mab 425; anti-EpCAM antibodies such as Crucell's anti-EpCAM, ING-1, and IS-IL-2; anti-ephrin B2/EphB4 antibodies; anti-Her2 antibodies such as Herceptin®, MDX-210; anti-FAP (fibroblast activation protein) antibodies such as sibrotuzumab; anti-ferritin antibodies such as NXT-211; anti-FGF-1 antibodies; anti-FGF-3 antibodies; anti-FGF-8 antibodies; anti-FGFR antibodies, anti-fibrin antibodies; anti-G250 antibodies such as WX-G250 and Rencarex®; anti-GD2 ganglioside antibodies such as EMD-273063 and TriGem; anti-GD3 ganglioside antibodies such as BEC2, KW-2871, and mitumomab; anti-gpIIb/IIIa antibodies such as ReoPro; anti-heparinase antibodies; anti-Her2/ErbB2 antibodies such as Herceptin® (trastuzumab), MDX-210, and pertuzumab; anti-HLA antibodies such as Oncolym®, Smart 1D10; anti-HM1.24 antibodies; anti-ICAM antibodies such as ICM3; anti-IgA receptor antibodies; anti-IGF-1 antibodies such as CP-751871 and EM-164; anti-IGF-1R antibodies such as IMC-A12; anti-IL-6 antibodies such as CNTO-328 and elsilimomab; anti-IL-15 antibodies such as HuMax™-IL15; anti-KDR antibodies; anti-laminin 5 antibodies; anti-Lewis Y antigen antibodies such as Hu3S193 and IGN-311; anti-MCAM antibodies; anti-Mud antibodies such as BravaRex and TriAb; anti-NCAM antibodies such as ERIC-1 and ICRT; anti-PEM antigen antibodies such as Theragyn and Therex; anti-PSA antibodies; anti-PSCA antibodies such as IG8; anti-Ptk antibodies; anti-PTN antibodies; anti-RANKL antibodies such as AMG-162; anti-RLIP76 antibodies; anti-SK-1 antigen antibodies such as Monopharm C; anti-STEAP antibodies; anti-TAG72 antibodies such as CC49-SCA and MDX-220; anti-TGF-β antibodies such as CAT-152; anti-TNF-α antibodies such as CDP571, CDP870, D2E7, Humira® (adalimumab), and Remicade® (infliximab); anti-TRAIL-R1 and TRAIL-R2 antibodies; anti-VE-cadherin-2 antibodies; and anti-VLA-4 antibodies such as Antegren™. Furthermore, anti-idiotype antibodies including but not limited to the GD3 epitope antibody BEC2 and the gp72 epitope antibody 105AD7, may be used. In addition, bispecific antibodies including but not limited to the anti-CD3/CD20 antibody Bi20 may be used.

Examples of antibodies that may be co-administered to treat autoimmune or inflammatory disease, transplant rejection, GVHD, and the like include, but are not limited to, anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcγR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, and anti-TNFa antibodies such as CDP571, CDP870, D2E7, Infliximab, MAK-195F, anti-VLA-4 antibodies such as Antegren. Examples of other Fc-containing molecules that may be co-administered to treat autoimmune or inflammatory disease, transplant rejection, GVHD, and the like include, but are not limited to, the p75 TNF receptor/Fc fusion Enbrel® (etanercept) and Regeneron's IL-1 trap.

Examples of antibodies that may be co-administered to treat infectious diseases include, but are not limited to, anti-anthrax antibodies such as ABthrax, anti-CMV antibodies such as CytoGam and sevirumab, anti-cryptosporidium antibodies such as CryptoGAM, Sporidin-G, anti-helicobacter antibodies such as Pyloran, anti-hepatitis B antibodies such as HepeX-B, Nabi-HB, anti-HIV antibodies such as HRG-214, anti-RSV antibodies such as felvizumab, HNK-20, palivizumab, RespiGam, and anti-staphylococcus antibodies such as Aurexis, Aurograb, BSYX-A110, and SE-Mab.

Alternatively, the antibodies of the present invention may be co-administered or with one or more other molecules that compete for binding to one or more Fc receptors. For example, co-administering inhibitors of the inhibitory receptor FcγRIIb may result in increased effector function. Similarly, co-administering inhibitors of the activating receptors such as FcγRIIIa may minimize unwanted effector function. Fc receptor inhibitors include, but are not limited to, Fc molecules that are engineered to act as competitive inhibitors for binding to FcγRIIb FcγRIIIa, or other Fc receptors, as well as other immunoglobulins and specifically the treatment called IVIg (intravenous immunoglobulin). In one embodiment, the inhibitor is administered and allowed to act before the antibody is administered. An alternative way of achieving the effect of sequential dosing would be to provide an immediate release dosage form of the Fc receptor inhibitor and then a sustained release formulation of the antibody of the invention. The immediate release and controlled release formulations could be administered separately or be combined into one unit dosage form. Administration of an FcγRIIb inhibitor may also be used to limit unwanted immune responses, for example anti-Factor VIII antibody response following Factor VIII administration to hemophiliacs.

In one embodiment, the antibodies of the present invention are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; Stella et al., "Prodrugs: A Chemical Approach to Targeted Drug Delivery," Directed Drug Delivery; and Borchardt et al., (ed.): 247-267, Humana Press, 1985, all incorporated entirely by reference. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies of the present invention include but are not limited to any of the aforementioned chemotherapeutic agents.

A variety of other therapeutic agents may find use for administration with the antibodies of the present invention. In one embodiment, the antibody is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the antibody is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CDI), CAI, CD59 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin-12, kringle 5 (plasminogen fragment), marimastat, metalloproteinase inhibitors (eg. TIMPs), 2-methodyestradiol, MMI 270 (CGS 27023A), plasminogen activiator inhibitor (PAI), platelet factor-4 (PF4), prinomastat, prolactin 16 kDa fragment, proliferin-related protein (PRP), PTK 787/ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-β), vasculostatin, vasostatin (calreticulin fragment), ZS6126, and ZD6474.

In a preferred embodiment, the antibody is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (STI571, Gleevec®; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva™, OSI Pharmaceuticals/Genentech), all patent publications incorporated entirely by reference.

In another embodiment, the antibody is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but not limited to: nonsteroidal anti-inflammatory drugs (NSAIDs) such as asprin, ibuprofed, celecoxib, diclofenac, etodolac, fenoprofen, indomethacin, ketoralac, oxaprozin, nabumentone, sulindac, tolmentin, rofecoxib, naproxen, ketoprofen, and nabumetone; steroids (eg. glucocorticoids, dexamethasone, cortisone, hydroxycortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD52, CD64, CD80, CD86, CD147, CD152, complement factors (C5, D) CTLA4, eotaxin, Fas, ICAM, ICOS, IFNα, IFNβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (eg. leflunomide), methotrexate, minocycline, mizoribine, mycophenolate mofetil, rapamycin, and sulfasasazine.

In an alternate embodiment, antibody of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In a preferred embodiment, cytokines or other agents that stimulate cells of the immune system are co-administered with the antibody of the present invention. Such a mode of treatment may enhance desired effector function. For example, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et al. (2003) Scand. J. Immunol. 57: 221-8, incorporated entirely by reference), may be co-administered. Also, agents that stimulate neutrophils, including but not limited to G-CSF, GM-CSF, and the like may be administered. Furthermore, agents that promote migration of such immunostimulatory cytokines may be used. Also additional agents including but not limited to interferon gamma, IL-3 and IL-7 may promote one or more effector functions.

In an alternate embodiment, cytokines or other agents that inhibit effector cell function are co-administered with the antibody of the present invention. Such a mode of treatment may limit unwanted effector function.

In an additional embodiment, the antibody is administered with one or more antibiotics, including but not limited to: aminoglycoside antibiotics (eg. apramycin, arbekacin, bambermycins, butirosin, dibekacin, gentamicin, kanamycin, neomycin, netilmicin, paromomycin, ribostamycin, sisomycin, spectrinomycin), aminocyclitols (eg. sprctinomycin), amphenicol antibiotics (eg. azidamfenicol, chloramphenicol, florfrnicol, and thiamphemicol), ansamycin antibiotics (eg. rifamide and rifampin), carbapenems (eg. imipenem, meropenem, panipenem); cephalosporins (eg. cefaclor, cefadroxil, cefamandole, cefatrizine, cefazedone, cefozopran, cefpimizole, cefpiramide, cefpirome, cefprozil, cefuroxine, cefixime, cephalexin, cephradine), cephamycins (cefbuperazone, cefoxitin, cefminox, cefinetazole, and cefotetan); lincosamides (eg. clindamycin, lincomycin); macrolide (eg. azithromycin, brefeldin A, clarithromycin, erythromycin, roxithromycin, tobramycin), monobactams (eg. aztreonam, carumonam, and tigernonam); mupirocin; oxacephems (eg. flomoxef, latamoxef, and moxalactam); penicillins (eg. amdinocillin, amdinocillin pivoxil, amoxicillin, bacampicillin, bexzylpenicillinic acid, benzylpenicillin sodium, epicillin, fenbenicillin, floxacillin, penamecillin, penethamate hydriodide, penicillin o-benethamine, penicillin O, penicillin V, penicillin V benzoate, penicillin V hydrabamine, penimepicycline, and phencihicillin potassium); polypeptides (eg. bacitracin, colistin, polymixin B, teicoplanin, vancomycin); quinolones (amifloxacin, cinoxacin, ciprofloxacin, enoxacin, enrofloxacin, feroxacin, flumequine, gatifloxacin, gemifloxacin, grepafloxacin, lomefloxacin, moxifloxacin, nalidixic acid, norfloxacin, ofloxacin, oxolinic acid, pefloxacin, pipemidic acid, rosoxacin, rufloxacin, sparfloxacin, temafloxacin, tosufloxacin, trovafloxacin); rifampin; streptogramins (eg. quinupristin, dalfopristin); sulfonamides (sulfanilamide, sulfamethoxazole); tetracyclenes (chlortetracycline, demeclocycline hydrochloride, demethylchlortetracycline, doxycycline, duramycin, minocycline, neomycin, oxytetracycline, streptomycin, tetracycline, vancomycin).

Anti-fungal agents such as amphotericin B, ciclopirox, clotrimazole, econazole, fluconazole, flucytosine, itraconazole, ketoconazole, niconazole, nystatin, terbinafine, terconazole, and tioconazole may also be used.

Antiviral agents including protease inhibitors, reverse transcriptase inhibitors, and others, including type I interferons, viral fusion inhibitors, and neuramidase inhibitors, may also be used. Examples of antiviral agents include, but are not limited to, acyclovir, adefovir, amantadine, amprenavir, clevadine, enfuvirtide, entecavir, foscarnet, gangcyclovir, idoxuridine, indinavir, lopinavir, pleconaril, ribavirin, rimantadine, ritonavir, saquinavir, trifluridine, vidarabine, and zidovudine, may be used.

The antibodies of the present invention may be combined with other therapeutic regimens. For example, in one embodiment, the patient to be treated with an antibody of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the antibody of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient.

It is of course contemplated that the antibodies of the invention may employ in combination with still other therapeutic techniques such as surgery or phototherapy.

EXAMPLES

Examples are provided below to illustrate the present invention. These examples are not meant to constrain the present invention to any particular application or theory of operation.

Example 1

Fc Variants with Reduced FcγR- and Complement-mediated Effector Function

For some applications it may be favorable to reduce or eliminate binding to one or more FcγRs, or reduce or eliminate one or more FcγR- or complement-mediated effector functions including but not limited to ADCC, ADCP, and/or CDC. This is often the case for therapeutic antibodies whose mechanism of action involves blocking or antagonism but not killing of the cells bearing target antigen. In these cases depletion of target cells is undesirable and can be considered a side effect. Effector function can also be a problem for radiolabeled antibodies, referred to as radioconjugates, and antibodies conjugated to toxins, referred to as immunotoxins. These drugs can be used to destroy cancer cells, but the recruitment of immune cells via Fc interaction with FcγRs brings healthy immune cells in proximity to the deadly payload (radiation or toxin), resulting in depletion of normal lymphoid tissue along with targeted cancer cells.

A previously unconsidered advantage of ablated FcγR- and complement-binding is that in cases where effector function is not needed, binding to FcγR and complement may effectively reduce the active concentration of drug. Binding to Fc ligands may localize an antibody or Fc fusion to cell surfaces or in complex with serum proteins wherein it is less active or inactive relative to when it is free (uncomplexed). This may be due to decreased effective concentration at binding sites where the antibody is desired, or perhaps Fc ligand binding may put the Fc polypeptide in a conformation in which it is less active than it would be if it were unbound. An additional consideration is that FcγR-receptors may be one mechanism of antibody turnover, and can mediate uptake and processing by antigen presenting cells such as dendritic cells and macrophages. This may affect affect the pharmacokinetics (or in vivo half-life) of the antibody or Fc fusion and its immunogenicity, both of which are critical parameters of clinical performance.

Variants comprising insertions, deletions, and substitutions in the Fc region were engineered to reduce or ablate interaction with FcγRs and complement. Insertions and deletions are not commonly used in protein engineering strategies to modulate binding interactions because of the potential for large perturbations to protein structure and stability. However as illustrated in FIG. 3, the flexible hinge region of an antibody may be uniquely amenable to engineering of insertions and deletions. The hinge region, defined herein from position 221-236, contains part of the Fc region, and contains some binding determinants for interaction with Fc receptors. The FcγR binding site begins approximately at residue 233, yet structurally, the CH2 domain begins at position 237. Thus it may be that insertions and deletions at and N-terminal to position 237 can be used to modulate interaction with FcγRs and complement, yet without affecting the stability and fidelity of the structured CH2 domain.

FIG. 4. lists a series of variants that were designed to reduce or ablate interaction with FcγRs and complement. The variants were constructed in the context of an antibody comprising the Fv region of the anti-Her2 antibody trastuzumab and the constant heavy chain of the human IgG1. Human IgG2 and IgG4 versions were also constructed to compare effector function of the Fc variants with naturally existing IgG antibodies.

The genes for the variable region of anti-Her2 antibody trastuzumab (Carter et al., 1992, Proc Natl Acad Sci USA 89:4285-4289) were constructed using recursive PCR, and subcloned into the mammalian expression vector pcDNA3.1Zeo (Invitrogen) comprising the full length light kappa (Cκ) constant region for the light chain, or the heavy chain IgG1, IgG2, or IgG4 constant regions for the heavy chain. Amino acid modifications were constructed in the Fc region of the antibodies in the pcDNA3.1Zeo vector using quick-change mutagenesis techniques (Stratagene). DNA was sequenced to confirm the fidelity of the sequences. Plasmids containing heavy chain gene (VH-CH1-CH2-CH3) (wild-type or variants) were co-transfected with plasmid containing light chain gene (VL-Cκ) into 293T cells. Media were harvested 5 days after transfection, and antibodies were purified from the supernatant using protein A affinity chromatography (Pierce). The sequences of the Cκ and IgG isotype constant chains are shown in FIG. 20.

In order to evaluate the interaction of the antibodies with Fc receptors, the extracellular regions of human Fc receptors R131 and H131 FcγRIIa, and V158 and F158 FcγRIIIa containing C-terminal 6xHis tags were obtained by PCR from clones obtained from the Mammalian Gene Collection (MGC), or generated de novo using recursive PCR. Receptors were expressed in 293T cells and purified using nickel affinity chromatography. His-tagged extracellular regions of human FcγRI and FcγRIIb were obtained from R&D Systems.

Binding affinity to human FcγRs by Fc variant antibodies was measured using surface plasmon resonance (SPR), also referred to as BIAcore. Surface plasmon resonance measurements were performed using a Biacore 3000 instrument (Biacore). Antibodies were captured onto an immobilized protein NG (Pierce) CM5 biosensor chip (Biacore), generated using a standard primary amine coupling protocol. All measurements were performed in HBS-EP (0.01 M HEPES pH 7.4, 0.15 M NaCl, 3 mM EDTA, 0.005% v/v surfactant P20, Biacore) and glycine buffer (10 mM glycine-HCl, pH 1.5, Biacore) was used for the Protein A/G surface regeneration. All antibodies (50 nM in HBS-EP) were immobilized on the protein A/G surface for 5 minutes at 1 ul/min. Fc receptors in serial dilutions were injected over antibody bound surface for 2 min at 20 ul/min followed by 2 or 3 min dissociation phase. After each cycle the Protein A/G surface was regenerated by injecting glycine buffer (pH 1.5) for 30 s at 10 ul/min. Data were processed by zeroing time and response before the injection of receptor and by subtracting of appropriate non-specific signals (response of reference channel and injection of running buffer). Kinetic analysis was performed by global fitting of binding data with a 1:1 binding model (Langmuir) using the BIAevaluation software.

Figure 5A:
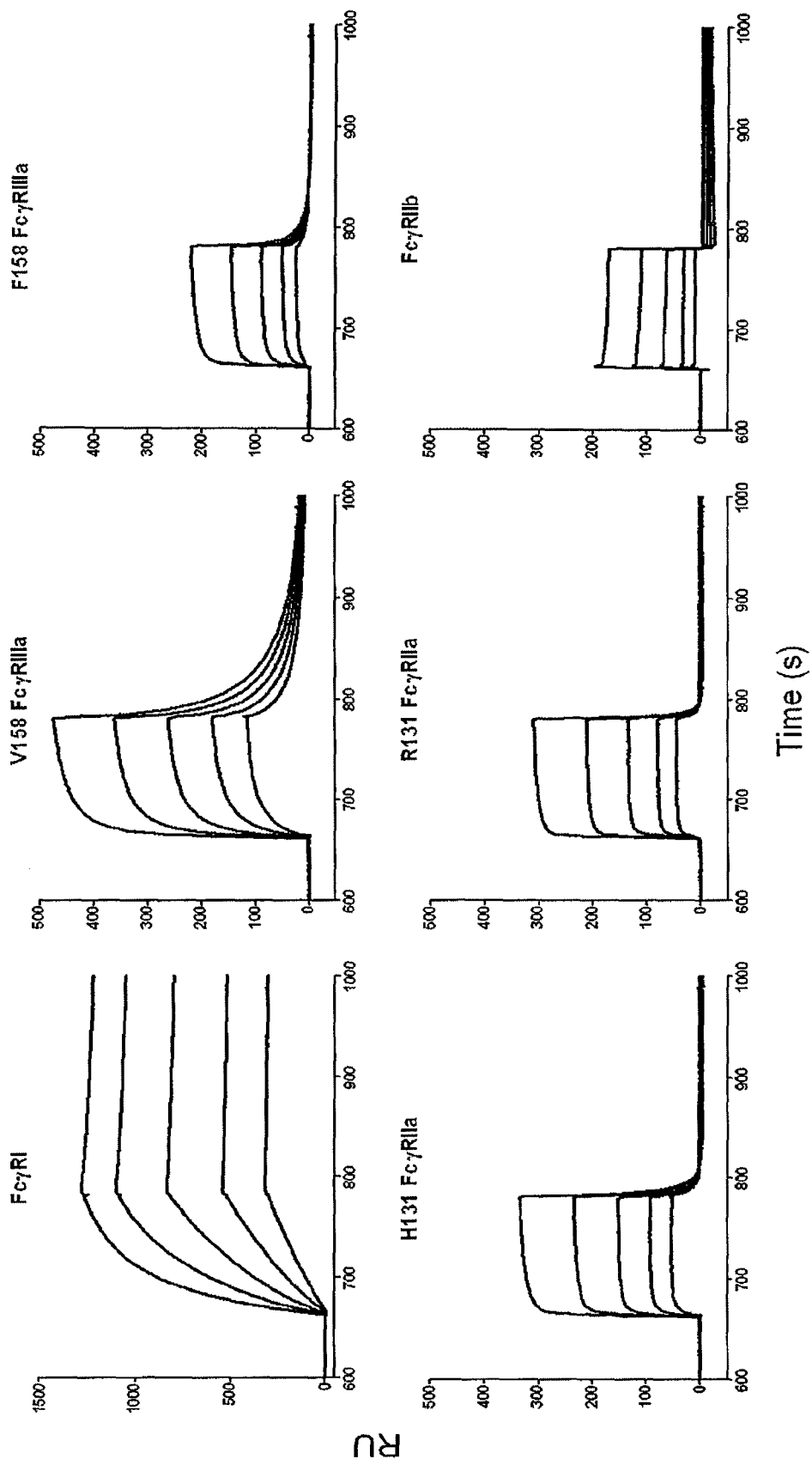
FIGS. 5a and 5b. Surface Plasmon Resonance (SPR) (Biaore) sensorgrams for binding of WT and Fc variant anti-Her2 antibodies to human Fc receptors.
Figure 5B:
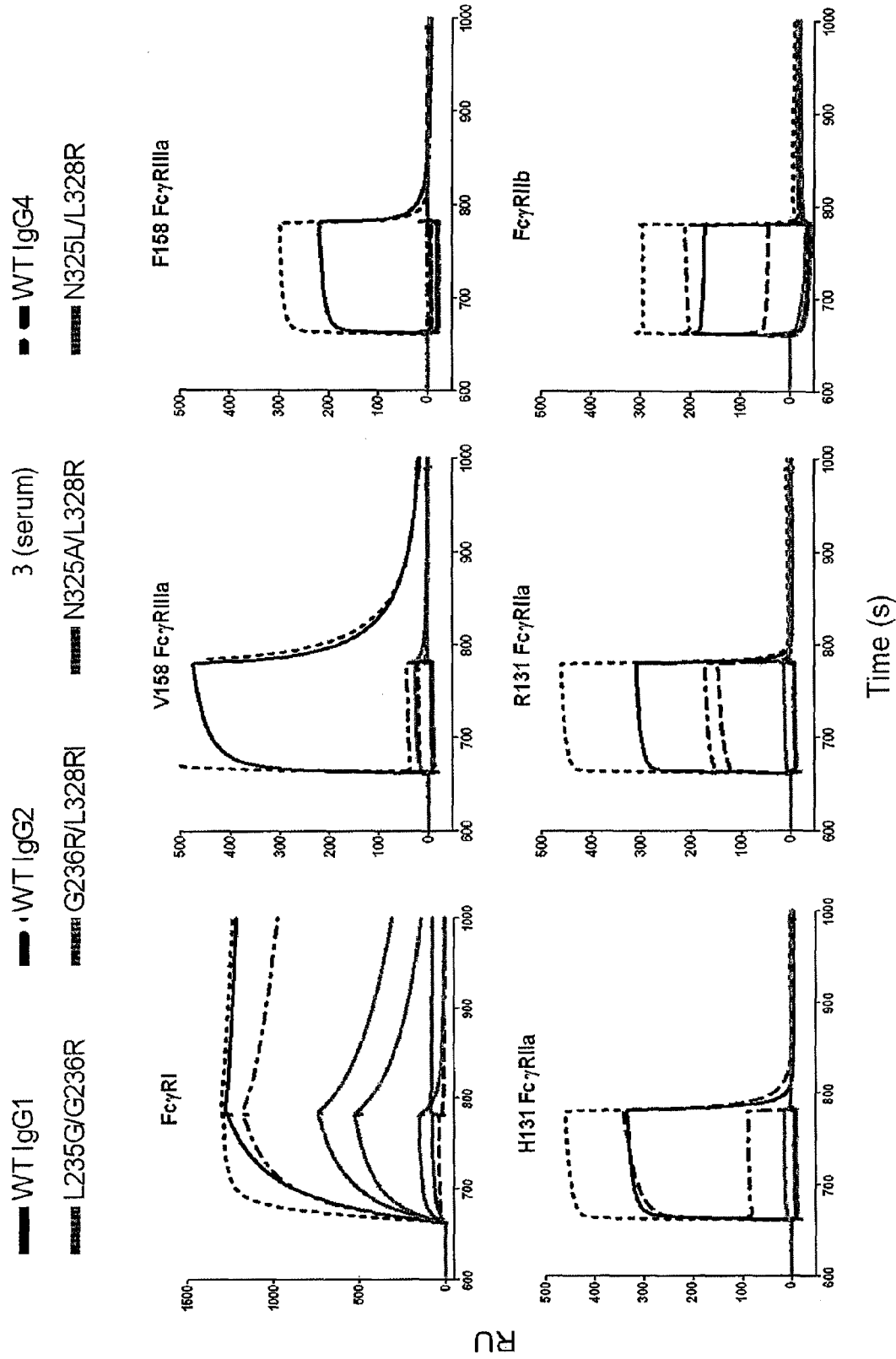
Figure 7:
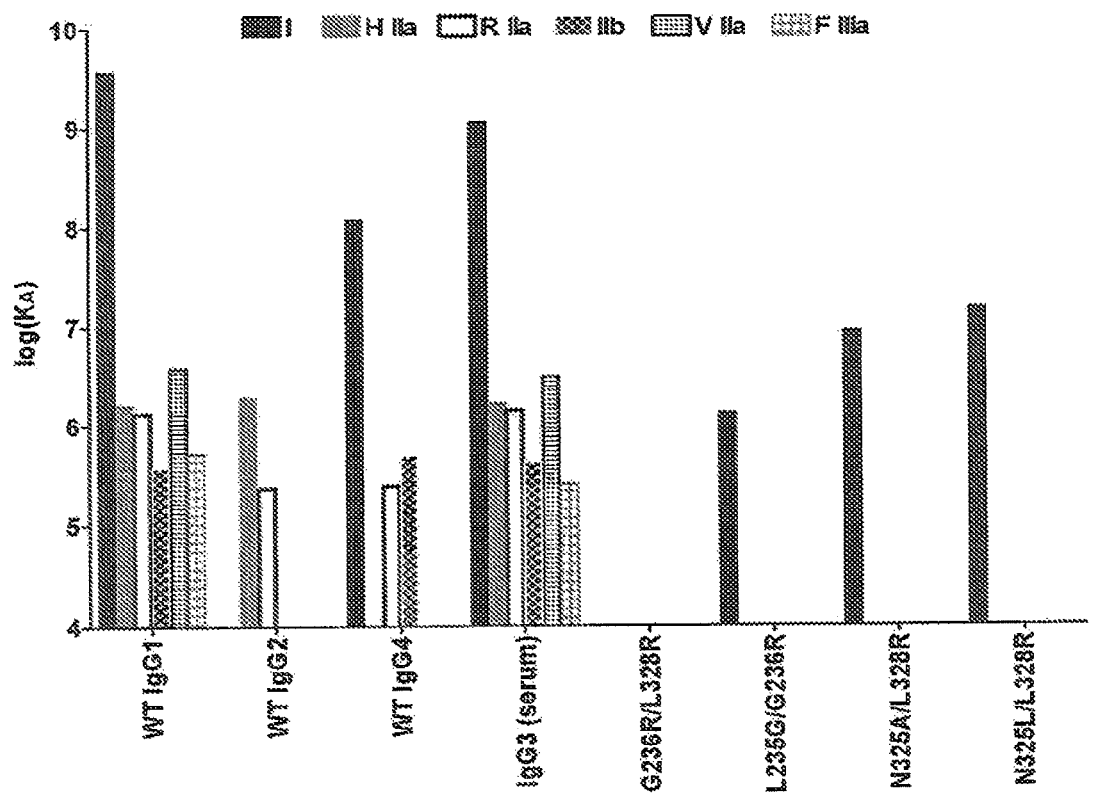
FIG. 7. Affinities for binding of WT and Fc variant antibodies to human FcγRs obtained from the data provided in FIG. 6. The graph is a plot of the log of the $K_A$ ($K_A=1/K_D$ as provided in FIG. 6) for binding of each variant to each of the Fc receptors. I=FcγRI, H IIa=H131 FcγRIIa, R IIa=R131 FcγRIIa, IIb=FcγRIIb, V IIIa=V158 FcγRIIIa, and F IIIa=F158 FcγRIIIa.

FIG. 5a shows the normalized SPR sensorgrams for each concentration for binding of WT IgG1 to the human Fc receptors FcγRI, both isoforms (H131 and R131) FcγRIIa, FcγRIIb, and both isofoforms (V158 and F158) of FcγRIIIa. An identical experiment was run for the other IgG isotypes (monoclonal IgG1, IgG2, and IgG4 with anti-Her2 variable region and polyclonal serum IgG3 purchased commercially) as well as select variants. FIG. 5b shows representative sensorgrams from each antibody at the highest concentration for each receptor. The higher amplitude and slower off-rates observed with IgG1 and IgG3 relative to IgG2 and IgG4 are consistent with the weaker binding of the latter. In contrast, no binding was observed for all of the variants tested, with the exception of FcγRI for some of the variants. Langmuir fits of the Biacore data for all the variants provided equilibrium $K_D$s (FIG. 6). FIG. 7 shows a plot of the affinities ($K_A=1/K_D$) on a logarithmic scale for binding of each antibody to each receptor. As can be seen, variant G236R/L328R shows no binding to any of the FcγRs. Variants L235G/G236R, N325A/L328R, and N325L/L328R show no binding to FcγRII and FcγRIII receptors, and show some albeit reduced binding to FcγRI.

Figure 8:
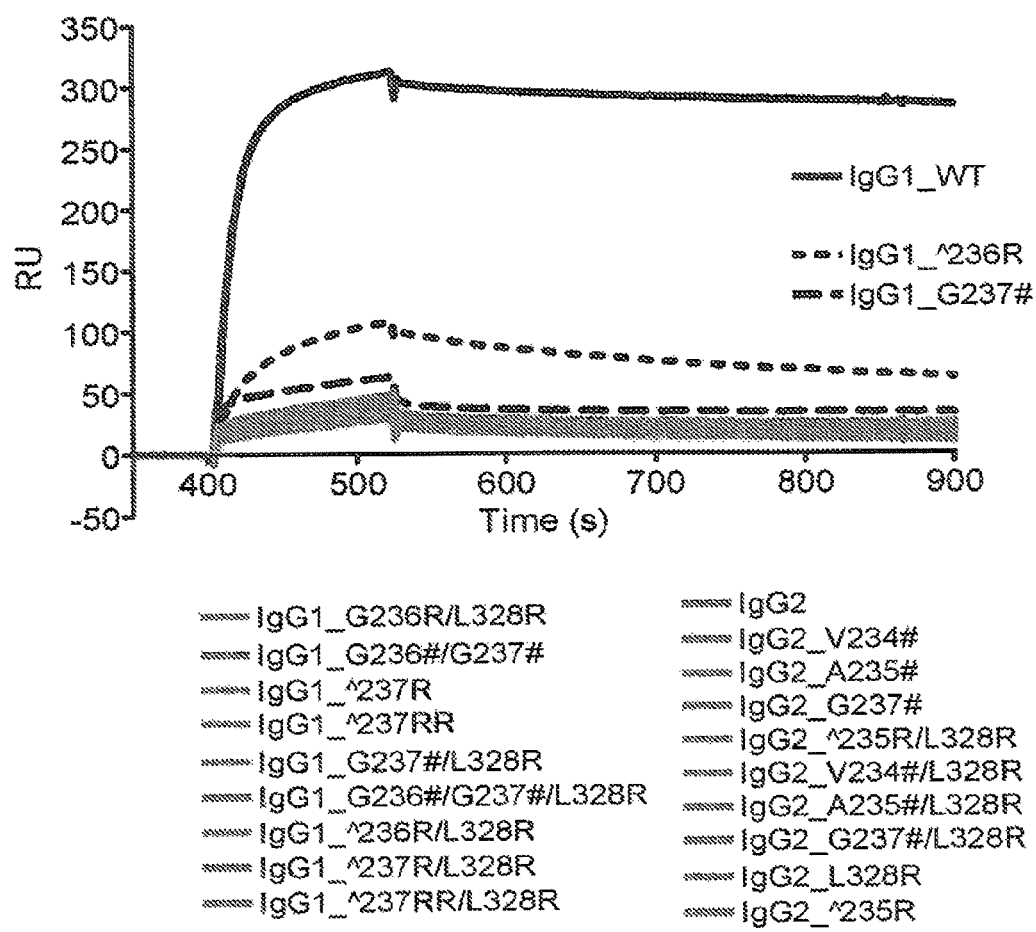
FIG. 8. SPR sensorgrams at the highest receptor concentration for binding of WT and Fc variant antibodies to human FcγRI.
Figure 9:
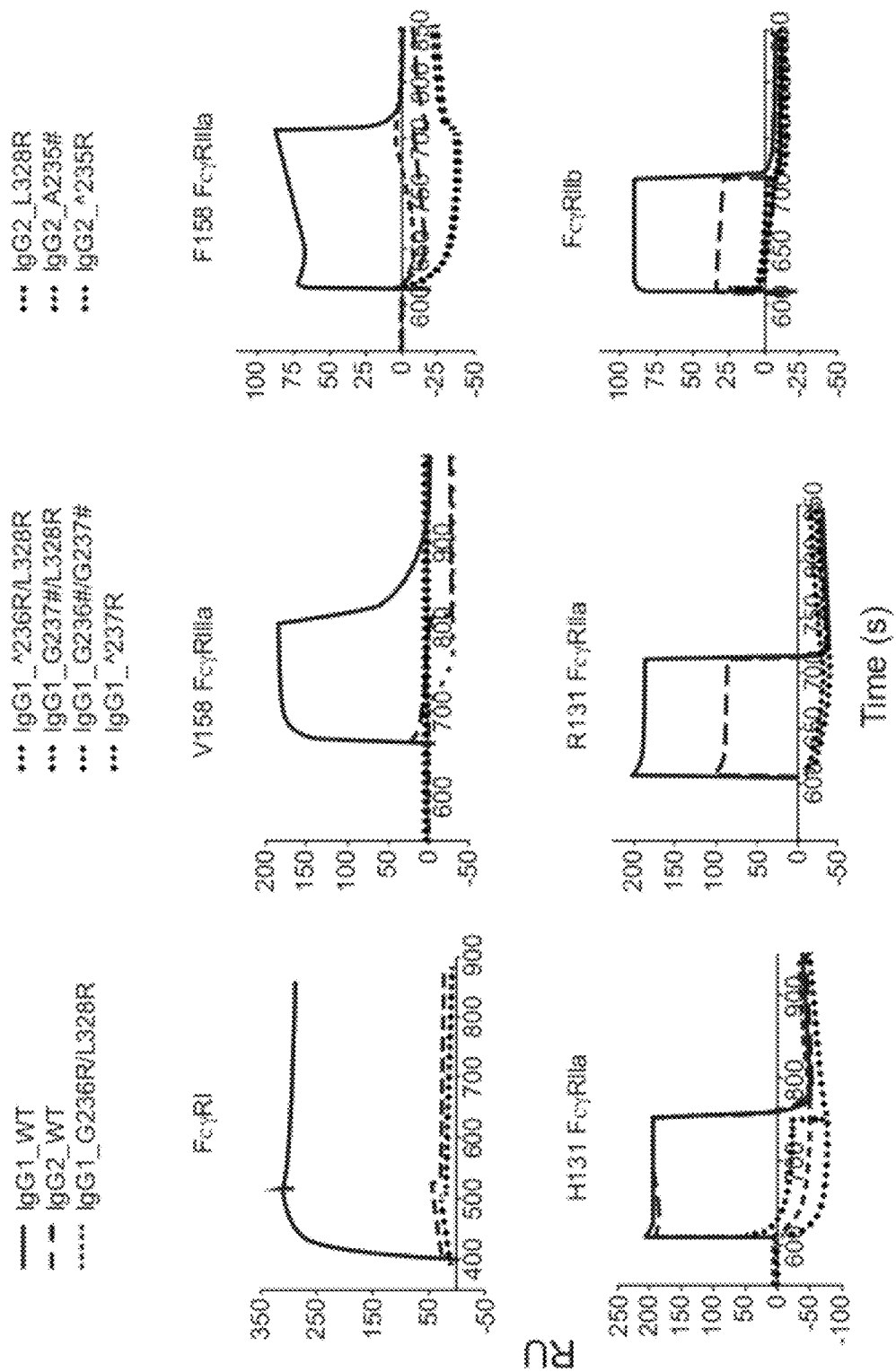
FIG. 9. SPR sensorgrams at the highest receptor concentration for binding of WT and Fc variant antibodies to human FcγRI, H131 FcγRIIa, R131FcγRIIa, FcγRIIb, V158 FcγRIIIa, and F158 FcγRIIIa.

Because binding to FcγRI was the most difficult among the Fc receptors to reduce, this receptor was used as the primary screen for the other variants. Other variants comprising insertions and deletions in the hinge region, as well as in some cases substitutions in the Fc region, were screened for binding to FcγRI using Biacore as described above. FIG. 8 shows the sensorgrams at the highest receptor concentration for all of the variants and WT IgG1. As can be seen, ^236R, which has an arginine insertion after position 236, and G237#, which has a deletion of G237, have reduced but observable binding to FcγRI. In contrast, all other variants, comprising a variety of insertions and deletions in the hinge, as well as substitutions in the Fc region, have completely ablated binding to the high affinity receptor FcγRI. Select variants were tested for binding to all signaling FcγRs by Biacore. FIG. 9 shows sensorgrams at the highest concentration for binding of these variants to human FcγRI, FcγRIIa, FcγRIIb, and FcγRIIIa. As can be seen, these variants show no detectable binding to any of the human FcγRs. The binding data for all of the variants to all of the receptors tested are summarized in FIG. 6.

Figure 10:
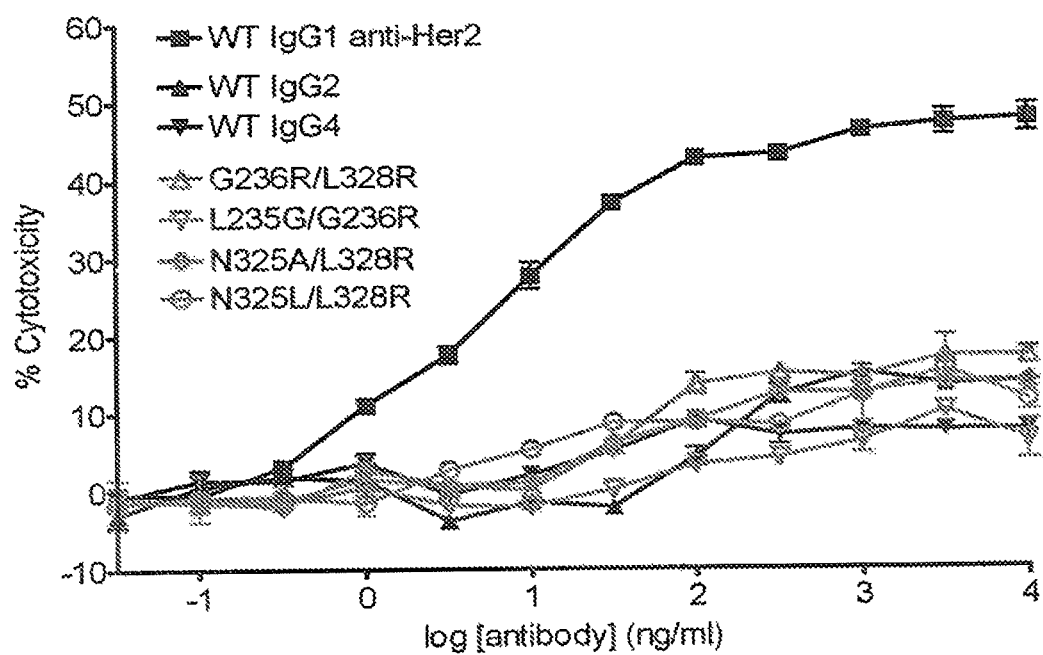
FIG. 10. ADCC assay comparing PBMC ADCC activity of anti-Her2 Fc variant antibodies with that of native IgG isotypes IgG1, IgG2, and IgG4.

To assess the impact of the variants with reduced/ablated FcγR binding, select variants were tested for their capacity to mediate antibody dependent cellular cytotoxicity (ADCC). Human PBMCs were used as effector cells, and the Her2+ cell line Sk-Br-3 was used as target cells. PBMCs were purified from leukopacks using a Ficoll gradient, and ADCC was measured by LDH release. Target cells were seeded into 96-well plates and opsonized using native IgG or Fc variant antibodies at the indicated concentrations. Triton X100 and PBMCs alone were run as controls. Effector cells were added and plates were incubated at 37° C., 5% $CO_2$ for 4 h. Cells were then incubated with LDH reaction mixture for 10 min, and fluorescence was measured using a Wallac Victor2 fluorometer (PerkinElmer). Fluorescence due to spontaneous PBMC and target cell lysis (without antibodies) was subtracted from experimental values (with antibodies), normalized to maximal (Triton) and minimal (no Triton) lysis, and fit to a sigmoidal dose-response model. FIG. 10 shows that variants with reduced FcγR binding do not mediate ADCC, similarly to WT IgG2 and IgG4 and in contrast to WT IgG1 which binds with high affinity to FcγRs, particularly FcγRIIIa. PBMC ADCC is dominatetd by NK cells, which only express FcγRIIIa.

Monocyte-derived effector cells, including for example macrophages, express not only FcγRIIIa, but also FcγRI, FcγRIIa, and the inhibitory receptor FcγRIIb. Macrophages are phagocytes that act as scavengers to engulf dead cells, foreign substances, and other debris. Importantly, macrophages are profefssional antigen presenting cells (APCs), taking up pathogens and foreign structures in peripheral tissues, then migrating to secondary lymphoid organs to initiate adaptive immune responses by activating naive T cells. Unlike NK cells, macrophages express the range of FcγRs, and thus their activation and function may be dependent on engagement of antibody immune complexes with receptors other than only FcγRIIIa. To evaluate the effect of ablation of FcγR affinity, the ^236R/L328R variant was tested for its capacity to mediate macrophage antibody dependent cellular phagocytosis (ADCP). WT IgG1 was also run as a comparator and control.

Figure 11:
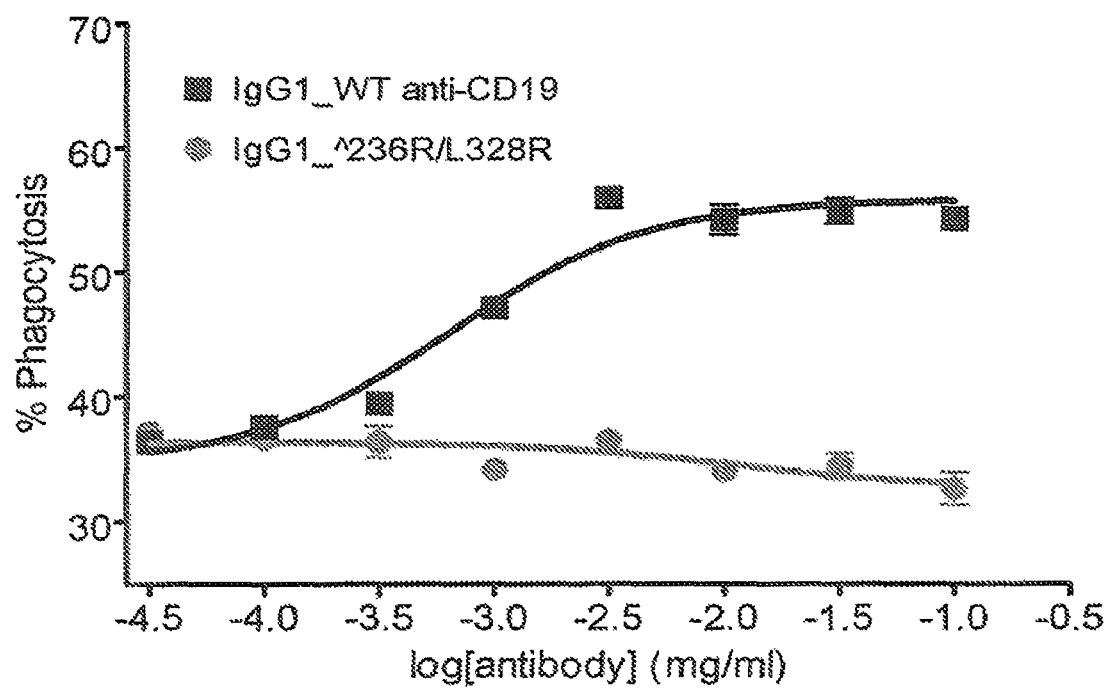
FIG. 11. ADCP assay comparing macrophage phagocytosis of anti-CD19 Fc variant antibody with that of native IgG1.

Phagocytosis carried out using the variable region of an anti-CD19 antibody, a humanized and affinity matured version of the murine 4G7 antibody as described U.S. patent application Ser. No. 11/838,824, titled "Optimized Antibodies that Target CD19," filed Aug. 14, 2007. The heavy chain variable region of this antibody was subcloned into the pcDNA3.1 vector containing the heavy chain constant regions of IgG1 and ^236R/L328R. Antibodies were expressed and purified as described above. CD14$^+$ macrophages were purified from PBMCs by EasySep® Human Monocyte Enrichment Kit without CD16 depletion (Stemcell Technologies). Purified CD14$^+$ monocytes were cultured in M-CSF (Peprotech) at 50 ng/ml for 5 days in a humidified incubator and differentiated into macrophages. Macrophage ADCP was determined by flow cytometry using CD19+ Ramos cells as target cells. Target cells were labeled with PKH67 (Sigma) and seeded into 96-well plates in the presence of 10% human serum. Fc variant antibodies were diluted serially to half-log concentrations and added to the target cells such that the highest concentration was 1 µg/ml. Monocyte-derived macrophages were then added at an effector to target ratio of 3:1, cells were spun down briefly, and incubated at 37° C. for 4 h. Cells were detached from the plate surface with HyQtase, stained with anti-CD11b APC, anti-CD14 APC, and anti-CD66 PE, washed with PBS, and fixed with 1% paraformaldehyde. Phagocytosis was evaluated on a FACS Canto II flow cytometer (BD Biosciences), and percent phagocytosis was calculated as the number of double positive cells divided by the total number of tumor cells. The intensity of CD66 staining was used to determine the degree to which tumor cells were internalized. FIG. 11 shows the results of the experiment. As can be seen, in contrast to WT IgG1, the variant, which contains an insertion in the hinge and a substitution in the Fc region, does not mediate ADCP.

Figure 12:
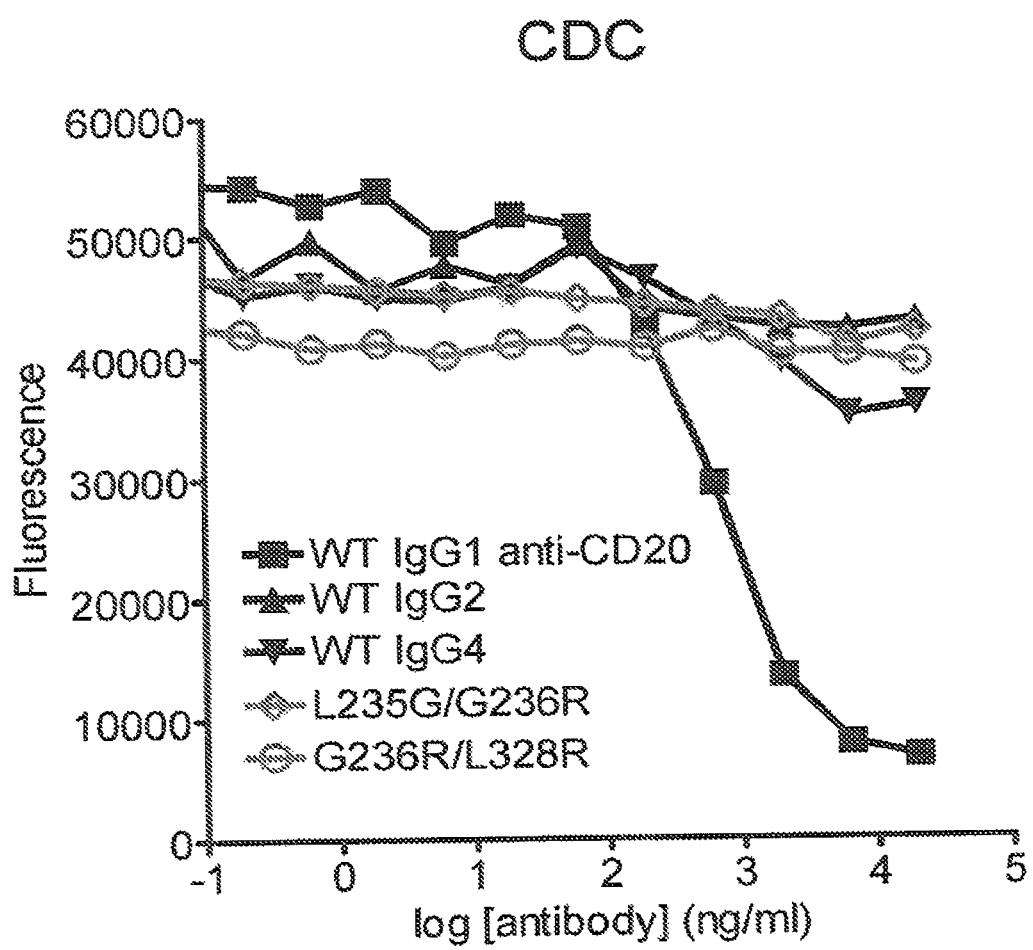
FIG. 12. CDC assay comparing complement activity of anti-CD20 Fc variant antibodies with that of native IgG isotypes IgG1, IgG2, and IgG4.
Figure 16:
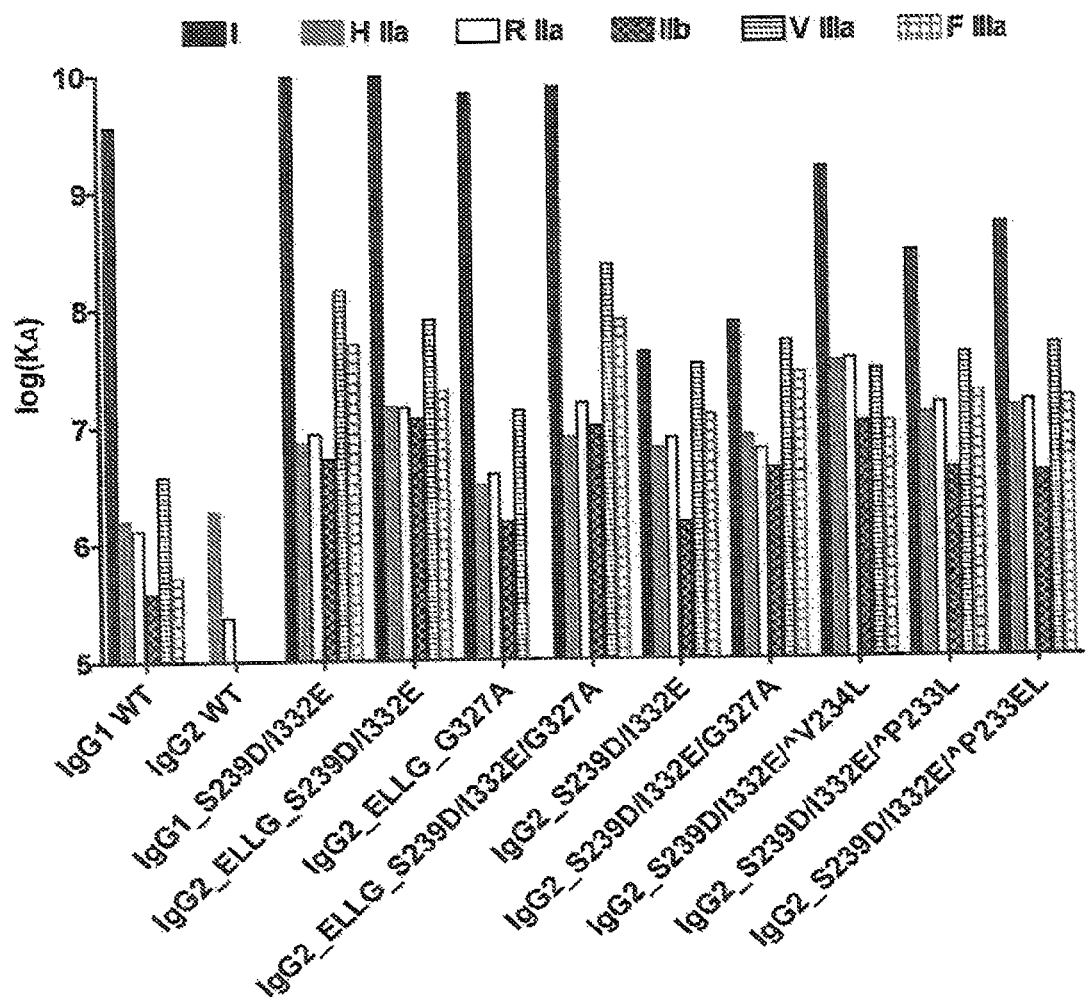
FIG. 16. Affinities for binding of WT and Fc variant antibodies to human FcγRs obtained from SPR data provided in FIG. 15. The graph is a plot of the log of the $K_A$ ($K_A=1/K_D$ as provided in FIG. 15) for binding of each variant to each of the Fc receptors. I=FcγRI, H IIa=H131 FcγRIIa, R IIa=R131FcγRIIa, IIb=FcγRIIb, V IIIa=V158 FcγRIIIa, and F IIIa=F158 FcγRIIIa. ELLG=P233E/V234L/A235L/^235G.
Figure 17:
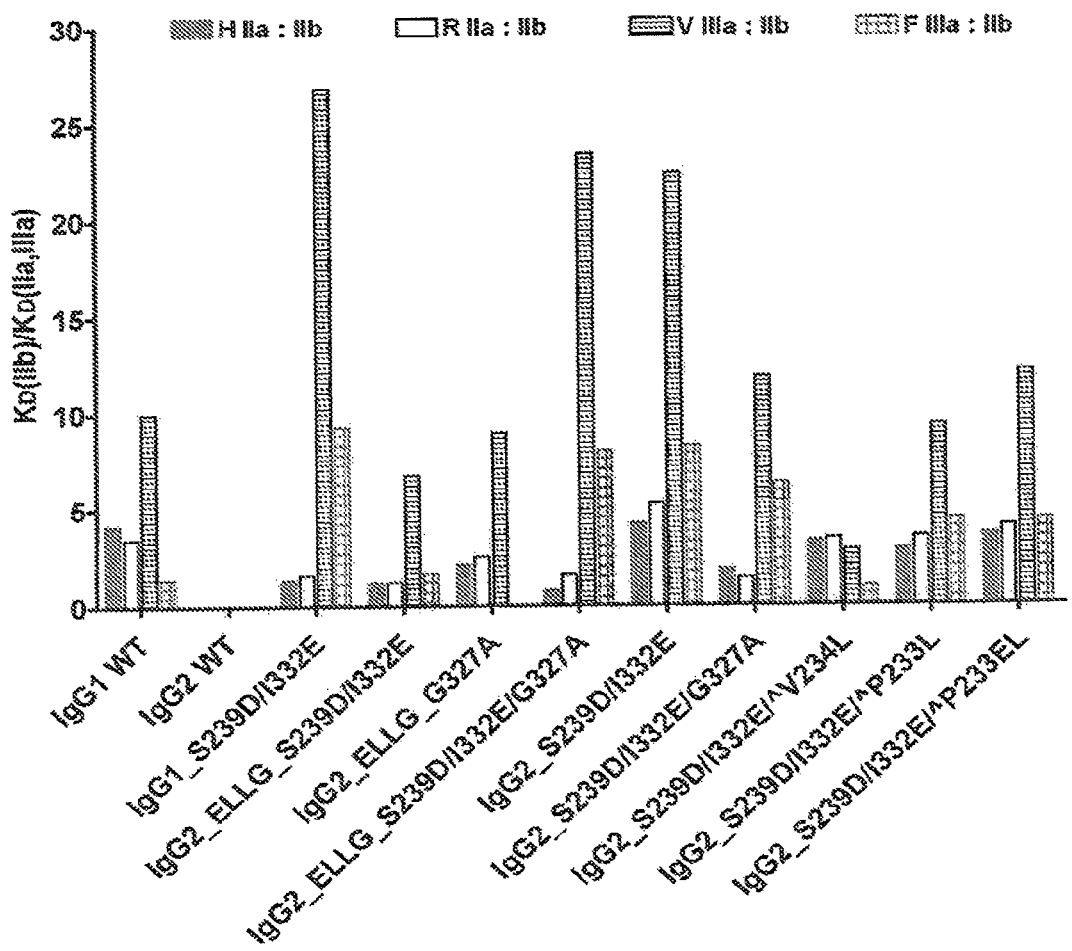
FIG. 17. Affinity ratios of WT and Fc variant antibodies for the human FcγRs. Data are provided in FIG. 15b. ELLG=P233E/V234L/A235L/^235G.

Finally, select variants with reduced FcγR binding were further tested for their capacity to mediate complement mediated cytotoxicity (CDC). The binding site for complement on the Fc region is separate from but overlapping with the site for binding to FcγRs. CDC activity was tested in the context of antibodies targeting CD20. The variants were constructed in the context of the anti-CD20 antibody PRO70769 (PCT/US2003/040426, hereby entirely incorporated by reference), which is known to mediate measurable CDC and ADCC in cell-based assays. The genes for the variable regions of PRO70769 were constructed using recursive PCR, and subcloned into the mammalian expression vector pcDNA3.1Zeo (Invitrogen) comprising the full length light kappa (Cκ) for the light chain, and either variant or WT IgG heavy chain constant regions. Antibodies were expressed and purified as described above. A cell-based assay was used to measure the capacity of the Fc variants to mediate CDC. Lysis was measured using release of Alamar Blue to monitor lysis of Fc variant and WT anti-CD20-opsonized WIL2-S lymphoma cells by human serum complement. Target cells were washed 3× in 10% FBS medium by centrifugation and resuspension, and WT or variant rituximab antibody was added at the indicated final concentrations. Human serum complement (Quidel) was diluted 50% with medium and added to antibody-opsonized target cells. Final complement concentration was 1/6$^{th}$ original stock. Plates were incubated for 2 hrs at 37° C., Alamar Blue was added, cells were cultured for two days, and fluorescence was measured. Data from this assay are shown in FIG. 12. As can be seen, the variants with modifications at positions 235, 236, and 328, do not mediate CDC activity, similarly to WT IgG2 and IgG4 and in contrast to IgG1 anti-CD20.

The results show that insertions and deletions in the hinge region, particularly at or after positions 233-237, provide the capability to reduce and even ablate FcγR- and complement-mediated effector functions. In addition, the data show that combination of insertions and deletions with substitutions in the Fc region are good. In particular, insertions and deletions in the hinge region may be combined preferably with substitutions at positions 235, 236, 237, 325, and 328. For example, substitutions 235G, 236R, 237K, 325L, 325A, and 328R may be combined with insertions after positions 233, 234, 235, 236, and 237, and/or with deletions at positions 233, 234, 235, 236, and 237. Preferred embodiments of the invention for reducing or ablating FcγR- and/or complement-mediated effector function are provided in FIG. 13.

This list of preferred Fc variants is not meant to constrain the present invention. Because combinations of Fc variants of the present invention have typically resulted in additive or synergistic binding modulations, and accordingly additive or synergistic modulations in effector function, it is anticipated that as yet unexplored combinations of the Fc variants provided in the present invention, or with other previously disclosed modifications, will also provide favorable results. Indeed all combinations of the any of the insertions, deletions, and/or substitutions provided are embodiments of the present invention. Furthermore, combinations of any of the Fc variants of the present invention with other discovered or undiscovered Fc variants may also provide favorable properties, and these combinations are also contemplated as embodiments of the present invention. Further, insertions, deletions, and substitutions at all positions disclosed herein are contemplated.

As discussed above, reduced FcγR affinity and/or effector function may be optimal for Fc polypeptides for which Fc ligand binding or effector function leads to toxicity and/or reduced efficacy. For example, antibodies that target CTLA-4 block inhibition of T-cell activation and are effective at promoting anti-tumor immune response, but destruction of T cells via antibody mediated effector functions may be counterproductive to mechanism of action and/or potentially toxic. Indeed toxicity has been observed with clinical use of the anti-CTLA-4 antibody ipilimumab (Maker et al., 2005, Ann Surg Oncol 12:1005-16, hereby entirely incorporated by reference). The sequences for the anti-CTLA-4 antibody ipilimumab (Mab 10D.1, MDX010) (U.S. Pat. No. 6,984,720, hereby entirely incorporated by reference) are provided in FIG. 19. The use of an anti-CTLA-4 here is solely an example, and is not meant to constrain application of the Fc variants to this antibody or any other particular Fc polypeptide. Other exemplary applications for reduced Fc ligand binding and/or effector function include but are not limited to anti-TNFα antibodies, including for example infliximab and adalimumab, anti-VEGF antibodies, including for example bevacizumab, anti-α4-integrin antibodies, including for example natalizumab, and anti-CD32b antibodies, including for example those described in U.S. Ser. No. 10/643,857, hereby entirely incorporated by reference.

Example 2

Fc Variants with Selective FcγR Affinity

Improvement in affinity for FcγRs is a goal for enhancing the therapeutic activity of antibodies that are used to treat cancers and infectious diseases. A potentially important parameter in this approach is the selectivity of an antibody variant for activating versus inhibiting receptors. Whereas NK cells only express the activating receptor FcγRIIIa, other potentially important immune cell types, including neutrophils, macrophages, and dendritic cells, express the inhibitory receptor FcγRIIb, as well the other activating receptors FcγRI and FcγRIIa. For these cell types optimal effector function may result from an antibody variant that has enhanced affinity for activation receptors, for example FcγRI, FcγRIIa, and FcγRIIIa, yet reduced or unaltered affinity for the inhibitory receptor FcγRIIb. Notably, these other cells types can utilize FcγRs to mediate not only innate effector functions that directly lyse cells, for example ADCC, but can also phagocytose targeted cells and process antigen for presentation to other immune cells, events that can ultimately lead to the generation of adaptive immune response. Yet because all FcγRs interact with the same binding site on Fc, and because of the high homology among the FcγRs, obtaining variants that selectively enhance or reduce FcγR affinity is a major challenge.

The data provided in FIG. 7 indicate that WT IgG2 has a favorable FcγRIIa:FcγRIIb profile, that is greater affinity for the activating receptor H131 and R131FcγRIIa relative to the activating receptor FcγRIIb. However WT IgG2 has poor binding to FcγRI and FcγRIIIa. Amino acid modifications were designed in an effort to engineer IgG2 such that it maintains its favorable FcγRIIa:FcγRIIb profile, but binds the other activating receptors FcγRI and FcγRIIIa with enhanced affinity. These variants, listed in FIG. 14, comprise insertions, deletions, and substitutions in the context of IgG2.

Variants were constructed in the context of the anti-Her2 antibody trastuzumab, expressed, and purified as described above. Binding affinity to the human FcγRs was determined by Biacore as described above. Global langmuir fits of the data provided the equilibrium dissociation constants ($K_D$s) (FIG. 15a). The fold affinities of the activating receptors FcγRIIa and FcγRIIIa (both isoforms of each) relative to the inhibitory receptor FcγRIIb are plotted in FIG. 15b. The log of the affinities and the ratio of activating to inhibitory receptors are plotted in FIG. 16 and FIG. 17 respectively. As can be seen, the insertions and deletions in the hinge region, as well as substitutions in the Fc region, can be used to control the affinities and selectivities of the different FcγRs Taken together, the data provided in the present invention indicate that insertions and deletions in the hinge region may be used to modulate FcγR affinity and selectivity. In particular, insertions after positions 233, 234, 235, 236, and 237, and deletions at positions 233, 234, 235, 236, and 237 may provide optimal effector function properties. The current invention also demonstrates that combination of said amino acid modifications with other Fc substitutions may further provide optimal effector function properties. For example, substitutions that may be combined with the modifications of the invention are described in U.S. Ser. Nos. 10/672,280; 10/822,231; 11/396,495; 11/124,620; 11/538,406; U.S. Pat. No. 6,737,056; Shields et al, Journal of Biological Chemistry, 2001, 276(9):6591-6604; U.S. Pat. No. 6,528,624; Idusogie et al., 2001, J. Immunology 166:2571-2572; U.S. Ser. Nos. 10/754,922; 10/902,588; 10/370,749; Stavenhagen et al., 2007, Cancer Research 67(18):8882-90; all of which are herein expressly incorporated by reference. In a most preferred embodiment, the insertions and deletions of the invention are combined with one or more amino acid substutitions at a position selected from the group consisting of 234, 235, 236, 239, 243, 247, 255, 267, 268, 270, 280, 292, 293, 295, 298, 300, 305, 324, 326, 327, 328, 330, 332, 333, 334, 392, 396, and 421. For example, preferred substitutions that may be combined with the insertions and deletions of the invention include but are not limited to 234G, 234I, 235D, 235E, 235I, 235Y, 236A, 236S, 239D, 239E, 243L, 247L, 255L, 267D, 267E, 267Q, 268D, 268E, 270E, 280H, 280Q, 280Y, 292P, 293R, 295E, 298A, 298T, 298N, 300L, 305I, 324G, 324I, 326A, 326D, 326E, 326W, 326Y, 327H, 328A, 328F, 328I, 330I, 330L, 330Y, A330V, 332D, 332E, 333A, 333S, 334A, 334L, 392T, 396L, and 421K. Preferred combinations of insertions, deletions, and substitutions are described in FIG. 18.

This list of preferred Fc variants is not meant to constrain the present invention. Indeed all combinations of the any of the insertions, deletions, and/or substitutions provided are embodiments of the present invention. Furthermore, combinations of any of the Fc variants of the present invention with other discovered or undiscovered Fc variants may also provide favorable properties, and these combinations are also contemplated as embodiments of the present invention. Further, insertions, deletions, and substitutions at all positions disclosed herein are contemplated.

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

We claim:

1. A protein comprising a variant Fc region of a parent Fc polypeptide, wherein said variant Fc region comprises a first substitution at position 328 and a second substitution at or an insertion after position 236, wherein said first substitution is arginine, said second substitution is arginine, and said insertion is arginine, wherein said protein exhibits ablated binding affinity to more than one FcγR as compared to said parent polypeptide and numbering is according to the EU index as in Kabat.

2. The protein of claim 1, wherein said protein is an antibody.

3. The protein of claim 2, wherein said antibody is selected from the group consisting of a human antibody, a humanized antibody, and a monoclonal antibody.

4. The protein of claim 3, wherein said antibody is a humanized.

5. The protein of claim 1, wherein said protein exhibits ablated binding affinity to FcγRI and FcγRIIb.

6. The protein of claim 1, wherein said protein exhibits ablated binding affinity to FcγRIIa and FcγRIIb.

7. The protein of claim 1, wherein said protein exhibits ablated binding affinity to FcγRIIb and FcγRIIIa.

8. The protein of claim 2, wherein said antibody further comprises an engineered glycoform.

9. The protein of claim 2, wherein said antibody has specificity for a target antigen selected from the group consisting of A33, BAFF-R, CA 125, CD5, CD19, CD20, CD30, CD33, CD38, CD40, CD44, CD52, CD123, CD138, CEA, EGFR (ErbB-1), EpCAM, GD2, GD3, Her2/neu (ErbB-2), HM1.24, IGF-1R, IL-5R, IL-6R, integrin alpha5, integrin alpha5/beta1, integrin alpha5/beta3, Lewis Y related carbohydrate, MCAM (melanoma cell adhesion molecule), PSCA (prostate stem cell antigen), PSMA (protage specific membrane antigen), STEAP (six-transmembrane epithelial antigen of the prostate), and TAG-72 (tumor-associated glycoprotein-72).

* * * * *